United States Patent
Quesnelle et al.

(10) Patent No.: US 10,683,290 B2
(45) Date of Patent: Jun. 16, 2020

(54) TRICYCLIC COMPOUNDS AS ANTICANCER AGENTS

(71) Applicant: BRISTOL-MYERS SQUIBB COMPANY, Princeton, NJ (US)

(72) Inventors: Claude A. Quesnelle, Skillman, NJ (US); Lalgudi S. Harikrishnan, Skillman, NJ (US); Matthew D. Hill, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 57 days.

(21) Appl. No.: 15/573,141

(22) PCT Filed: May 11, 2016

(86) PCT No.: PCT/US2016/031701
§ 371 (c)(1),
(2) Date: Nov. 10, 2017

(87) PCT Pub. No.: WO2016/183114
PCT Pub. Date: Nov. 17, 2016

(65) Prior Publication Data
US 2018/0127413 A1    May 10, 2018

Related U.S. Application Data

(60) Provisional application No. 62/159,497, filed on May 11, 2015.

(51) Int. Cl.
*C07D 471/04* (2006.01)
*A61P 35/02* (2006.01)

(52) U.S. Cl.
CPC ............ *C07D 471/04* (2013.01); *A61P 35/02* (2018.01)

(58) Field of Classification Search
CPC .................................................... C07D 471/04
See application file for complete search history.

(56) References Cited

FOREIGN PATENT DOCUMENTS

| WO | WO 2014/134232 A1 | 9/2014 |
|---|---|---|
| WO | WO 2014/134267 A1 | 9/2014 |
| WO | WO 2014153043 * | 9/2014 |
| WO | WO 2014/164596 A1 | 10/2014 |

OTHER PUBLICATIONS

U.S. Appl. No. 14/770,230, filed Aug. 25, 2015.
U.S. Appl. No. 15/430,883, filed Feb. 13, 2017.
PCT/US2014/018914, Filing Date: Feb. 27, 2014.
U.S. Appl. No. 14/190,477, filed Feb. 26, 2014.
PCT/US2014/018820, Filing Date: Feb. 27, 2014.
U.S. Appl. No. 15/107,652, filed Jun. 23, 2016.
U.S. Appl. No. 14/580,355, filed Dec. 23, 2014.
U.S. Appl. No. 15/219,611, filed Jul. 26, 2016.
U.S. Appl. No. 15/661,373, filed Jul. 27, 2017.
PCT/US2014/072031, Filing Date: Dec. 23, 2014.
U.S. Appl. No. 15/150,492, filed May 10, 2016.
PCT/US2016/031707, Filing Date: May 11, 2016.
U.S. Appl. No. 15/573,151, filed Nov. 10, 2017.
PCT/US2016/031702, Filing Date: May 11, 2016.

* cited by examiner

*Primary Examiner* — Susanna Moore
(74) *Attorney, Agent, or Firm* — Elliott Korsen

(57) ABSTRACT

The present invention is directed to tricyclic compounds, pharmaceutically acceptable compositions comprising compounds of the invention and methods of using said compositions in the treatment of various disorders.

7 Claims, No Drawings
Specification includes a Sequence Listing.

SEQUENCE LISTING

```
<160> NUMBER OF SEQ ID NOS: 3

<210> SEQ ID NO 1
<211> LENGTH: 21
<212> TYPE: PRT
<213> ORGANISM: Tobacco vein mottling virus

<400> SEQUENCE: 1

Met Gly Ser Ser His His His His His His Ser Ser Gly Glu Thr Val
1               5                   10                  15

Arg Phe Gln Ser Met
            20

<210> SEQ ID NO 2
<211> LENGTH: 39
<212> TYPE: PRT
<213> ORGANISM: Tobacco vein mottling virus
```

```
<400> SEQUENCE: 2

Met Gly Ser Ser His His His His His His Ser Gly Glu Thr Val
1               5                   10                  15

Arg Phe Gln Gly Leu Asn Asp Ile Phe Glu Ala Gln Lys Ile Glu Trp
            20                  25                  30

His Glu Asp Thr Gly His Met
            35

<210> SEQ ID NO 3
<211> LENGTH: 21
<212> TYPE: PRT
<213> ORGANISM: Artificial Sequence
<220> FEATURE:
<223> OTHER INFORMATION: Biotinylated histone peptide
<220> FEATURE:
<221> NAME/KEY: MOD_RES
<222> LOCATION: (5)..(5)
<223> OTHER INFORMATION: ACETYLATION
<220> FEATURE:
<221> NAME/KEY: MOD_RES
<222> LOCATION: (8)..(8)
<223> OTHER INFORMATION: ACETYLATION
<220> FEATURE:
<221> NAME/KEY: MOD_RES
<222> LOCATION: (12)..(12)
<223> OTHER INFORMATION: ACETYLATION
<220> FEATURE:
<221> NAME/KEY: MOD_RES
<222> LOCATION: (16)..(16)
<223> OTHER INFORMATION: ACETYLATION

<400> SEQUENCE: 3

Ser Gly Arg Gly Lys Gly Gly Lys Gly Leu Gly Lys Gly Gly Ala Lys
1               5                   10                  15

Arg His Arg Lys Val
            20
```

TRICYCLIC COMPOUNDS AS ANTICANCER AGENTS

CROSS-REFERENCE TO RELATED APPLICATIONS

This application claims priority from U.S. Provisional Application No. 62/159,497 filed May 11, 2015, the disclosures of which are incorporated herein by reference in their entirety.

FIELD OF THE INVENTION

The invention provides novel tricyclic compounds, pharmaceutical compositions comprising the compounds, and methods of using them, for example, for the treatment or prophylaxis of certain cancers and to their use in therapy.

BACKGROUND OF THE INVENTION

The genomes of eukaryotic organisms are highly organized within the nucleus of the cell. The long strands of duplex DNA are wrapped around an octomer of histone proteins to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. There has been appreciation recently that chromatin templates form a fundamentally important set of gene control mechanisms referred to as epigenetic regulation. By conferring a wide range of specific chemical modifications to histones and DNA (such as acetylation, methylation, phosphorylation, ubiquitinylation and SUMOylation) epigenetic regulators modulate the structure, function and accessibility of our genome, thereby exerting a huge impact in gene expression.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine residues commonly but not exclusively in the context of histones. There is a family of around 50 proteins known to contain bromodomains, and they have a range of functions within the cell. The BET family of bromodomain containing proteins comprises 4 proteins (BRD2, BRD3, BRD4 and BRD-T) which contain tandem bromodomains capable of binding to two acetylated lysine residues in close proximity, increasing the specificity of the interaction.

BRD2 and BRD3 are reported to associate with histones along actively transcribed genes and may be involved in facilitating transcriptional elongation (Leroy et al., Mol. Cell. 2008 30(1):51-60), while BRD4 appears to be involved in the recruitment of the pTEF-I3 complex to inducible genes, resulting in phosphorylation of RNA polymerase and increased transcriptional output (Hargreaves et al., Cell, 2009 138(1): 1294145). All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al., Cell, 2004 117(3): 349-60).

Recent articles relating to this target include Prinjha et al., Trends in Pharmacological Sciences, March 2012, Vol. 33, No. 3, pp. 146-153; Conway, ACS Med. Chem. Lett., 2012, 3, 691-694 and Hewings et al., J. Med. Chem., 2012, 55, 9393-9413.

Small molecule BET inhibitors that are reported to be in clinical development include GSK-525762, OTX-015, TEN-010, CPI-0610, BAY-1238097, and ABBV-075.

Hundreds of epigenetic effectors have been identified, many of which are chromatin-binding proteins or chromatin-modifying enzymes. These proteins have been associated with a variety of disorders such as neurodegenerative disorders, metabolic diseases, inflammation and cancer. Thus, these compounds which inhibit the binding of a bromodomain with its cognate acetylated proteins, promise new approaches in the treatment of a range of autoimmune and inflammatory diseases or conditions and in the treatment of various types of cancer.

SUMMARY OF THE INVENTION

There is provided a compound of formula (I)

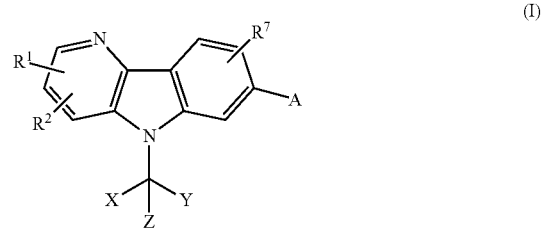

wherein:

A is optionally substituted heteroaryl, wherein the substituents are one or more R;

R is independently one or more hydrogen, $CD_3$, halogen, haloalkyl, hydroxyalkyl, CN, $CF_3$, $CH_2F$, $CHF_2$, optionally substituted $(C_1$-$C_6)$alkyl, optionally substituted $(C_1$-$C_6)$ alkoxy, optionally substituted $(C_3$-$C_6)$cycloalkyl, —$OR^4$, —$NR^3R^4$, $NR^3R^4(C_1$-$C_6)$alkyl-, —$NR^6OCOR^3$, —$NR^6COR^3$, —$NR^6CONR^3R^4$;

X and Y are independently selected from hydrogen, optionally substituted $(C_1$-$C_6)$alkyl, optionally substituted $(C_3$-$C_8)$cycloalkyl, optionally substituted aryl, optionally substituted heteroaryl or optionally substituted heterocyclo;

Z is hydrogen, halogen, —OH, $(C_1$-$C_6)$alkyl or $(C_1$-$C_6)$ alkoxy;

$R^1$ is hydrogen, halogen, —CN, —$OR^4$, —$NR^3R^4$, —$CONR^3R^4$, —COOH, —$OCONR^3R^4$, —$NR^6OCOR^3$, —$NR^6CONR^3R^4$, —$NR^6SO_2NR^3R^4$, —$NR^6SO_2R^4$, optionally substituted $(C_1$-$C_6)$alkyl, optionally substituted $(C_2$-$C_6)$alkenyl, optionally substituted $(C_2$-$C_6)$alkynyl, optionally substituted $(C_1$-$C_6)$alkoxy, optionally substituted $(C_3$-$C_8)$cycloalkyl, optionally substituted $(C_3$-$C_8)$cycloalkyl $(C_1$-$C_6)$alkyl, optionally substituted $(C_3$-$C_8)$cycloalkyl-CO—, optionally substituted $(C_3$-$C_8)$cycloalkyl-$SO_2$—, optionally substituted aryl $(C_1$-$C_6)$alkoxy-, optionally substituted $(C_3$-$C_8)$cycloalkyl $(C_1$-$C_6)$alkoxy-, optionally substituted heterocyclyl-CO—, optionally substituted $(C_1$-$C_6)$ alkyl-$SO_2$—, —$NR^6SO_2$-optionally substituted $(C_1$-$C_6)$ alkyl, —$NR^6SO_2$-optionally substituted heterocyclo, optionally substituted (C$_1$-C$_6$)alkyl-NR$^6$SO$_2$— or optionally substituted heterocyclo-NR$^6$SO$_2$—;

R$^2$ is hydrogen, halogen, —CN, OH, —CONR$^3$R$^4$, —NR$^6$COOR$^4$, —NR$^6$CONR$^3$R$^4$, —NR$^6$COR$^4$, —NR$^6$SO$_2$R$^5$, —SO$_2$NR$^3$R$^4$, —NR$^6$SO$_2$NR$^3$R$^4$, optionally substituted (C$_1$-C$_6$)alkyl, optionally substituted (C$_3$-C$_8$)cycloalkyl, optionally substituted (C$_1$-C$_6$) alkoxy, optionally substituted (C$_1$-C$_6$)alkyl-SO$_2$—, or optionally substituted aryl-SO$_2$—;

R$^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl;

R$^4$ is hydrogen, optionally substituted (C$_1$-C$_6$)alkyl or optionally substituted (C$_3$-C$_8$)cycloalkyl;

R$^5$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl;

R$^6$ is hydrogen or optionally substituted (C$_1$-C$_6$)alkyl;

R$^7$ is hydrogen, optionally substituted (C$_1$-C$_6$)alkyl, haloalkyl, —OR$^4$, CN, —CONH$_2$ or halogen;

or a pharmaceutically acceptable salt, tautomer or stereoisomer thereof.

In another aspect, there is provided a pharmaceutical composition comprising a compound of the invention or a pharmaceutically acceptable salt thereof and one or more pharmaceutically acceptable carriers, diluents or excipients.

In another aspect, there is provided a compound of the invention or a pharmaceutically acceptable salt thereof for use in therapy. In particular, for use in the treatment of a disease or condition for which a bromodomain inhibitor is indicated.

In another aspect, there is provided a method of treating autoimmune and inflammatory diseases or conditions which comprises administering to a subject in need thereof a therapeutically effective amount of a bromodomain inhibitor.

In another aspect, there is provided a method of treating cancer which comprises administering to a subject in need thereof a therapeutically effective amount of a bromodomain inhibitor.

In another aspect of the present invention, there is provided a method for treating a bromodomain-containing protein mediated disorder in a patient in need thereof, comprising the step of administering to said patient a compound of the invention.

DETAILED DESCRIPTION OF THE INVENTION

In a first aspect of the present invention, there is provided a compound of formula (I)

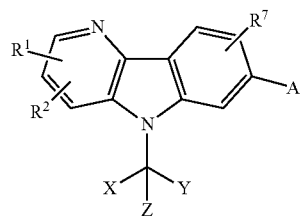

wherein:

A is optionally substituted heteroaryl, wherein the substituents are one or more R;

R is independently one or more hydrogen, CD$_3$, halogen, haloalkyl, hydroxyalkyl, CN, CF$_3$, CH$_2$F, CHF$_2$, optionally substituted (C$_1$-C$_6$)alkyl, optionally substituted (C$_1$-C$_6$) alkoxy, optionally substituted (C$_3$-C$_6$)cycloalkyl, —OR$^4$, —NR$^3$R$^4$, NR$^3$R$^4$(C$_1$-C$_6$)alkyl-, —NR$^6$OCOR$^3$, —NR$^6$COR$^3$, —NR$^6$CONR$^3$R$^4$;

X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo;

Z is hydrogen, halogen, —OH, (C$_1$-C$_6$)alkyl or (C$_1$-C$_6$) alkoxy;

R$^1$ is hydrogen, halogen, —CN, —OR$^4$, —NR$^3$R$^4$, —CONR$^3$R$^4$, —COOH, —OCONR$^3$R$^4$, —NR$^6$OCOR$^3$, —NR$^6$CONR$^3$R$^4$, —NR$^6$SO$_2$NR$^3$R$^4$, —NR$^6$SO$_2$R$^4$, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkoxy, optionally substituted (C$_3$-C$_8$)cycloalkyl, optionally substituted (C$_3$-C$_8$)cycloalkyl (C$_1$-C$_6$)alkyl, optionally substituted (C$_3$-C$_8$)cycloalkyl-CO—, optionally substituted (C$_3$-C$_8$)cycloalkyl-SO$_2$—, optionally substituted aryl (C$_1$-C$_6$)alkoxy-, optionally substituted (C$_3$-C$_8$)cycloalkyl (C$_1$-C$_6$)alkoxy-, optionally substituted heterocyclyl-CO—, optionally substituted (C$_1$-C$_6$) alkyl-SO$_2$—, —NR$^6$SO$_2$-optionally substituted (C$_1$-C$_6$) alkyl, —NR$^6$SO$_2$-optionally substituted heterocyclo, optionally substituted (C$_1$-C$_6$)alkyl-NR$^6$SO$_2$— or optionally substituted heterocyclo-NR$^6$SO$_2$—;

R$^2$ is hydrogen, halogen, —CN, OH, —CONR$^3$R$^4$, —NR$^6$COOR$^4$, —NR$^6$CONR$^3$R$^4$, —NR$^6$COR$^4$, —NR$^6$SO$_2$R$^5$, —SO$_2$NR$^3$R$^4$, —NR$^6$SO$_2$NR$^3$R$^4$, optionally substituted (C$_1$-C$_6$)alkyl, optionally substituted (C$_3$-C$_8$)cycloalkyl, optionally substituted (C$_1$-C$_6$) alkoxy, optionally substituted (C$_1$-C$_6$)alkyl-SO$_2$—, or optionally substituted aryl-SO$_2$—;

R$^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl;

R$^4$ is hydrogen, optionally substituted (C$_1$-C$_6$)alkyl or optionally substituted (C$_3$-C$_8$)cycloalkyl;

R$^5$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl;

$R^6$ is hydrogen or optionally substituted ($C_1$-$C_6$)alkyl;

$R^7$ is hydrogen, optionally substituted ($C_1$-$C_6$)alkyl, haloalkyl, —$OR^4$, CN, —$CONH_2$ or halogen;

or a pharmaceutically acceptable salt, tautomer or stereoisomer thereof.

In a second aspect of the invention, there is provided a compound according to the first aspect of the formula

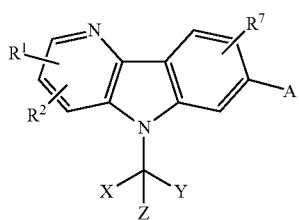

(II)

wherein:
A is

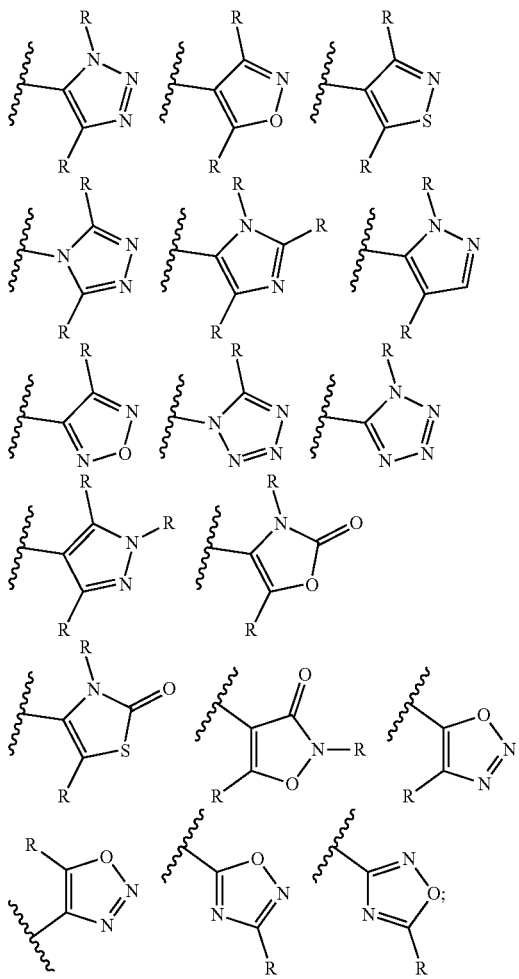

R is independently one or more hydrogen, $CD_3$, halogen, haloalkyl, hydroxyalkyl, CN, $CF_3$, $CH_2F$, $CHF_2$, optionally substituted ($C_1$-$C_6$)alkyl, optionally substituted ($C_1$-$C_6$) alkoxy, optionally substituted ($C_3$-$C_6$)cycloalkyl, —$OR^4$, —$NR^3R^4$, $NR^3R^4$($C_1$-$C_6$)alkyl-, —$NR^6OCOR^3$, —$NR^6COR^3$, —$NR^6CONR^3R^4$;

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl or ($C_1$-$C_6$) alkoxy;

$R^1$ is hydrogen, halogen, —CN, —$OR^4$, —$NR^3R^4$, —$CONR^3R^4$, —COOH, —$OCONR^3R^4$, —$NR^6OCOR^3$, —$NR^6CONR^3R^4$, —$NR^6SO_2NR^3R^4$, —$NR^6SO_2R^4$, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl ($C_1$-$C_6$)alkyl, optionally substituted ($C_3$-$C_8$)cycloalkyl-CO—, optionally substituted ($C_3$-$C_8$)cycloalkyl-$SO_2$—, optionally substituted aryl ($C_1$-$C_6$)alkoxy-, optionally substituted ($C_3$-$C_8$)cycloalkyl ($C_1$-$C_6$)alkoxy-, optionally substituted heterocyclyl-CO—, optionally substituted ($C_1$-$C_6$) alkyl-$SO_2$—, —$NR^6SO_2$-optionally substituted ($C_1$-$C_6$) alkyl, —$NR^6SO_2$-optionally substituted heterocyclo, optionally substituted ($C_1$-$C_6$)alkyl-$NR^6SO_2$— or optionally substituted heterocyclo-$NR^6SO_2$—;

$R^2$ is hydrogen, halogen, —CN, OH, —$CONR^3R^4$, —$NR^6COOR^4$, —$NR^6CONR^3R^4$, —$NR^6COR^4$, —$NR^6SO_2R^5$, —$SO_2NR^3R^4$, —$NR^6SO_2NR^3R^4$, optionally substituted ($C_1$-$C_6$)alkyl, optionally substituted ($C_3$-$C_8$)cycloalkyl, optionally substituted ($C_1$-$C_6$) alkoxy, optionally substituted ($C_1$-$C_6$)alkyl-$SO_2$—, or optionally substituted aryl-$SO_2$—;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl;

$R^4$ is hydrogen, optionally substituted ($C_1$-$C_6$)alkyl or optionally substituted ($C_3$-$C_8$)cycloalkyl;

$R^5$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl;

$R^6$ is hydrogen or optionally substituted ($C_1$-$C_6$)alkyl;

$R^7$ is hydrogen, optionally substituted ($C_1$-$C_6$)alkyl, haloalkyl, —$OR^4$, CN, —$CONH_2$ or halogen;

or a pharmaceutically acceptable salt, tautomer or stereoisomer thereof.

In a third aspect of the invention within the scope of the first two aspects, there is provided a compound of formula (I)

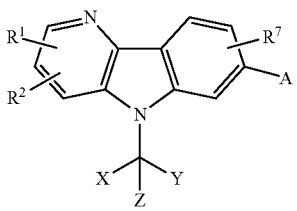

wherein;
A is

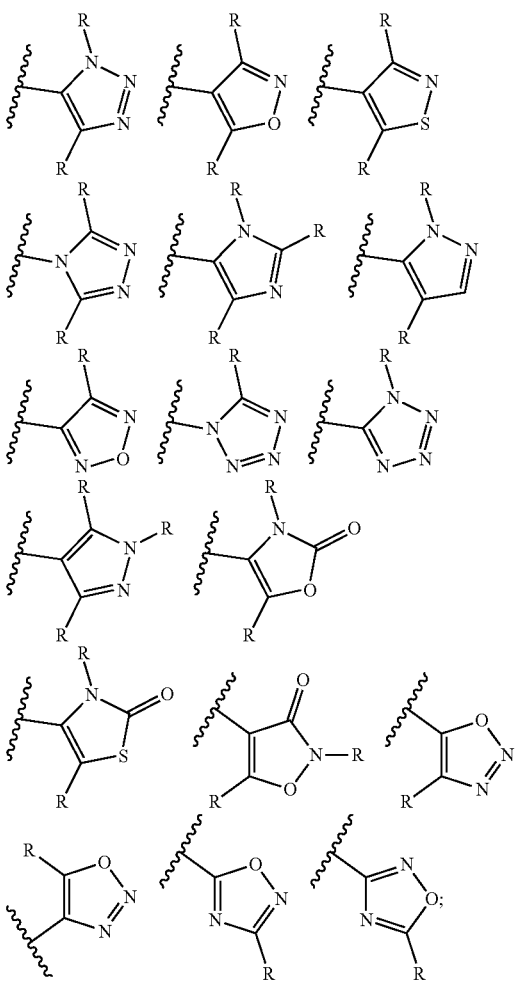

R is independently one or more hydrogen, $CD_3$, halogen, haloalkyl, hydroxyalkyl, CN, $CF_3$, $CH_2F$, $CHF_2$, optionally substituted $(C_1-C_6)$alkyl, optionally substituted $(C_1-C_6)$alkoxy, optionally substituted $(C_3-C_6)$cycloalkyl, $-OR^4$, $-NR^3R^4$, $NR^3R^4(C_1-C_6)$alkyl-, $-NR^6OCOR^3$, $-NR^6COR^3$, $-NR^6CONR^3R^4$;

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo;

Z is hydrogen, halogen, —OH, $(C_1-C_6)$alkyl or $(C_1-C_6)$alkoxy;

$R^1$ is hydrogen, halogen, —CN, $-OR^4$, $-NR^3R^4$, $-CONR^3R^4$, —COOH, $-OCONR^3R^4$, $-NR^6OCOR^3$, $-NR^6CONR^3R^4$, $-NR^6SO_2NR^3R^4$, $-NR^6SO_2R^4$, optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_3-C_8)$cycloalkyl, optionally substituted $(C_3-C_8)$cycloalkyl $(C_1-C_6)$alkyl, optionally substituted $(C_3-C_8)$cycloalkyl-CO—, optionally substituted $(C_3-C_8)$cycloalkyl-$SO_2$—, optionally substituted aryl $(C_1-C_6)$alkoxy-, optionally substituted $(C_3-C_8)$cycloalkyl $(C_1-C_6)$alkoxy-, optionally substituted heterocyclyl-CO—, optionally substituted $(C_1-C_6)$alkyl-$SO_2$—, $-NR^6SO_2$-optionally substituted $(C_1-C_6)$alkyl, $-NR^6SO_2$-optionally substituted heterocyclo, optionally substituted $(C_1-C_6)$alkyl-$NR^6SO_2$— or optionally substituted heterocyclo-$NR^6SO_2$—;

$R^2$ is hydrogen, halogen, —CN, OH, optionally substituted $(C_1-C_6)$alkyl, optionally substituted $(C_3-C_8)$cycloalkyl, optionally substituted $(C_1-C_6)$ alkoxy, optionally substituted $(C_1-C_6)$alkyl-$SO_2$—, or optionally substituted aryl-$SO_2$—;

$R^3$ is hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-$SO_2$—, optionally substituted heterocyclyl, optionally substituted heterocyclyl$(C_1-C_6)$alkyl, optionally substituted heteroaryl or optionally substituted heteroaryl $(C_1-C_6)$alkyl;

$R^4$ is hydrogen, optionally substituted $(C_1-C_6)$alkyl or optionally substituted $(C_3-C_8)$cycloalkyl;

$R^6$ is hydrogen or optionally substituted $(C_1-C_6)$alkyl;

$R^7$ is hydrogen, optionally substituted $(C_1-C_6)$alkyl, haloalkyl, $-OR^4$, CN, $-CONH_2$ or halogen;

or a pharmaceutically acceptable salt, tautomer or stereoisomer thereof.

In a 4$^{th}$ aspect within the scope of the prior aspects, there is provided a compound of the formula

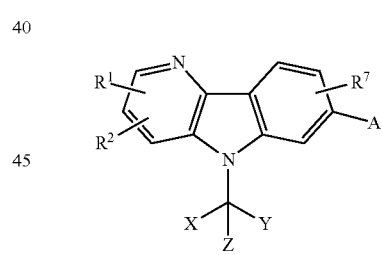

wherein
A is

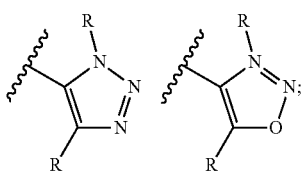

R is independently one or more hydrogen, $CD_3$, halogen, haloalkyl, hydroxyalkyl, CN, $CF_3$, $CH_2F$, $CHF_2$, optionally substituted $(C_1-C_6)$alkyl, optionally substituted $(C_1-C_6)$ alkoxy, optionally substituted $(C_3-C_6)$cycloalkyl, $-OR^4$, $-NR^3R^4$, $NR^3R^4(C_1-C_6)$alkyl-, $-NR^6OCOR^3$, $-NR^6COR^3$, $-NR^6CONR^3R^4$;

X and Y are independently selected from hydrogen, optionally substituted (C₁-C₆)alkyl, optionally substituted (C₃-C₈)cycloalkyl, optionally substituted aryl, optionally substituted heteroaryl or optionally substituted heterocyclo;

Z is hydrogen, halogen, —OH, (C₁-C₆)alkyl or (C₁-C₆) alkoxy;

R¹ is hydrogen, halogen, —CN, —OR⁴, —NR³R⁴, —CONR³R⁴, —COOH, —OCONR³R⁴, —NR⁶OCOR³, —NR⁶CONR³R⁴, —NR⁶SO₂NR³R⁴, —NR⁶SO₂R⁴, optionally substituted (C₁-C₆)alkyl, optionally substituted (C₂-C₆)alkenyl, optionally substituted (C₂-C₆)alkynyl, optionally substituted (C₁-C₆)alkoxy, optionally substituted (C₃-C₈)cycloalkyl, optionally substituted (C₃-C₈)cycloalkyl (C₁-C₆)alkyl, optionally substituted (C₃-C₈)cycloalkyl-CO—, optionally substituted (C₃-C₈)cycloalkyl-SO₂—, optionally substituted aryl (C₁-C₆)alkoxy-, optionally substituted (C₃-C₈)cycloalkyl (C₁-C₆)alkoxy-, optionally substituted heterocyclyl-CO—, optionally substituted (C₁-C₆) alkyl-SO₂—, —NR⁶SO₂-optionally substituted (C₁-C₆) alkyl, —NR⁶SO₂-optionally substituted heterocyclo, optionally substituted (C₁-C₆)alkyl-NR⁶SO₂— or optionally substituted heterocyclo-NR⁶SO₂—;

R² is hydrogen, halogen, —CN, OH, optionally substituted (C₁-C₆)alkyl, optionally substituted (C₃-C₈)cycloalkyl, optionally substituted (C₁-C₆) alkoxy, optionally substituted (C₁-C₆)alkyl-SO₂—, or optionally substituted aryl-SO₂—;

R³ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl (C₁-C₆)alkyl;

R⁴ is hydrogen, optionally substituted (C₁-C₆)alkyl or optionally substituted (C₃-C₈)cycloalkyl;

R⁶ is hydrogen or optionally substituted (C₁-C₆)alkyl;

R⁷ is hydrogen, optionally substituted (C₁-C₆)alkyl, haloalkyl, —OR⁴, CN, —CONH₂ or halogen;

or a pharmaceutically acceptable salt, tautomer or stereoisomer thereof.

In a 5ᵗʰ aspect of the invention within the scope of the prior aspects, there is provided a compound of the formula

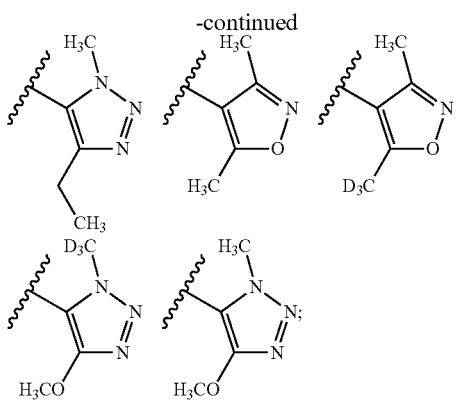

(I)

wherein:
A is

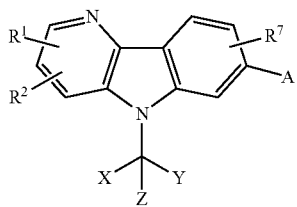

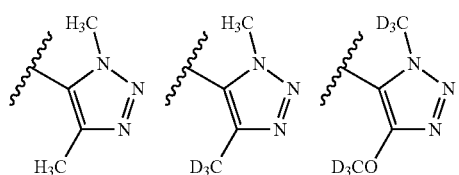

-continued

X and Y are independently selected from hydrogen, optionally substituted (C₁-C₆)alkyl, optionally substituted (C₃-C₈)cycloalkyl, optionally substituted aryl, optionally substituted heteroaryl or optionally substituted heterocyclo;

Z is hydrogen, halogen, —OH, (C₁-C₆)alkyl or (C₁-C₆) alkoxy;

R¹ is, independently at each occurrence, one or more hydrogen, halogen, —CN, —OR⁴, —NR³R⁴, —CONR³R⁴, —COOH, —OCONR³R⁴, —NR⁶OCOR³, —NR⁶CONR³R⁴, —NR⁶SO₂NR³R⁴, —NR⁶SO₂R⁴, optionally substituted (C₁-C₆)alkyl, optionally substituted (C₂-C₆)alkenyl, optionally substituted (C₂-C₆)alkynyl, optionally substituted (C₁-C₆)alkoxy, optionally substituted (C₃-C₈)cycloalkyl, optionally substituted (C₃-C₈)cycloalkyl (C₁-C₆)alkyl, optionally substituted (C₃-C₈)cycloalkyl-CO—, optionally substituted (C₃-C₈)cycloalkyl-SO₂—, optionally substituted aryl (C₁-C₆)alkoxy-, optionally substituted (C₃-C₈)cycloalkyl (C₁-C₆)alkoxy-, optionally substituted heterocyclyl-CO—, optionally substituted (C₁-C₆) alkyl-SO₂—, —NR⁶SO₂-optionally substituted (C₁-C₆) alkyl, —NR⁶SO₂-optionally substituted heterocyclo, optionally substituted (C₁-C₆)alkyl-NR⁶SO₂— or optionally substituted heterocyclo-NR⁶SO₂—;

R² is hydrogen, halogen, —CN, OH, optionally substituted (C₁-C₆)alkyl, optionally substituted (C₃-C₈)cycloalkyl, optionally substituted (C₁-C₆) alkoxy, optionally substituted (C₁-C₆)alkyl-SO₂—, or optionally substituted aryl-SO₂—;

R³ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl (C₁-C₆)alkyl;

R⁴ is hydrogen, optionally substituted (C₁-C₆)alkyl or optionally substituted (C₃-C₈)cycloalkyl;

R⁶ is hydrogen or optionally substituted (C₁-C₆)alkyl;

R⁷ is hydrogen, optionally substituted (C₁-C₆)alkyl, haloalkyl, —OR⁴, CN, —CONH₂ or halogen;

or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another aspect, there is provided a compound selected from the following 5-benzyl-7-(dimethyl-1,2-oxazol-4-yl)-2-methyl-5H-pyrido[3,2-b]indole-9-carboxamide, 4-{5-benzyl-2-methyl-5H-pyrido[3,2-b]indol-7-yl}-3,5-dimethyl-1,2-oxazole, 2-[7-(dimethyl-1H-1,2,3-triazol-5-yl)-5-[(S)-(4-fluorophenyl)(oxan-4-yl)methyl]-5H-pyrido[3,2-b]indol-3-yl]propan-2-ol, 2-[7-(dimethyl-1H-1,2,3-triazol-5-yl)-5-(1,1,1,7,7,7-hexafluoroheptan-4-yl)-5H-pyrido[3,2-b]indol-3-yl]propan-2-ol, 2-[7-(dimethyl-1H-1,2,3-triazol-5-yl)-5-(heptan-4-yl)-5H-pyrido[3,2-b]indol-3-yl]propan-2-ol, 2-[7-(dimethyl-1H-1,2,3-triazol-5-yl)-5-[4,4,4-trifluoro-1-(pyridin-2-yl)butyl]-5H-pyrido[3,2-b]indol-3-yl]propan-2-ol, Entantiomer A, 2-[7-(dimethyl-1H-1,2,3-triazol-5-yl)-5-[4,4,4-trifluoro-1-(pyridin-2-yl)butyl]-5H-pyrido[3,2-b]indol-3-yl]propan-2-ol, Entantiomer B, 2-[7-(dimethyl-1H-1,2,3-triazol-5-yl)-5-[(S)-oxan-4-yl(phenyl)methyl]-5H-pyrido[3,2-b]indol-3-yl]propan-2-ol, 2-[7-(dimethyl-1H-1,2,3-triazol-5-yl)-5-[(S)-(2-fluorophenyl)(oxan-4-yl)methyl]-5H-pyrido[3,2-b]indol-3-yl]propan-2-ol, 2-[7-(dimethyl-1H-1,2,3-triazol-5-yl)-9-fluoro-5-(1,1,1,7,7,7-hexafluoroheptan-4-yl)-5H-pyrido[3,2-b]indol-3-yl]propan-2-ol, 2-[7-(dimethyl-1H-1,2,3-triazol-5-yl)-9-fluoro-5-[(S)-oxan-4-yl(phenyl)methyl]-5H-pyrido[3,2-b]indol-3-yl]propan-2-ol, 2-[9-chloro-7-(dimethyl-1H-1,2,3-triazol-5-yl)-5-(1,1,1,7,7,7-hexafluoroheptan-4-yl)-5H-pyrido[3,2-b]indol-3-yl]propan-2-ol, 2-[9-chloro-7-(dimethyl-1H-1,2,3-triazol-5-yl)-5-[(S)-oxan-4-yl(phenyl)methyl]-5H-pyrido[3,2-b]indol-3-yl]propan-2-ol, 2-[7-(dimethyl-1,2-oxazol-4-yl)-5-[(S)-oxan-4-yl(phenyl)methyl]-5H-pyrido[3,2-b]indol-3-yl]propan-2-ol, 2-[7-(dimethyl-1,2-oxazol-4-yl)-5-[(S)-(2-fluorophenyl)(oxan-4-yl)methyl]-5H-pyrido[3,2-b]indol-3-yl]propan-2-ol, 2-{7-[4-($^2$H$_3$)methyl-1-methyl-1H-1,2,3-triazol-5-yl]-5-[(S)-oxan-4-yl(phenyl)methyl]-5H-pyrido[3,2-b]indol-3-yl}propan-2-ol, 2-[7-(dimethyl-1,2-oxazol-4-yl)-6-fluoro-5-[(S)-oxan-4-yl(phenyl)methyl]-5H-pyrido[3,2-b]indol-3-yl]propan-2-ol, 2-[7-(dimethyl-1,2-oxazol-4-yl)-8-fluoro-5-[(S)-oxan-4-yl(phenyl)methyl]-5H-pyrido[3,2-b]indol-3-yl]propan-2-ol, 2-[7-(dimethyl-1H-1,2,3-triazol-5-yl)-8-fluoro-5-[(S)-oxan-4-yl(phenyl)methyl]-5H-pyrido[3,2-b]indol-3-yl]propan-2-ol, 2-[7-(dimethyl-1H-1,2,3-triazol-5-yl)-6-fluoro-5-[(S)-oxan-4-yl(phenyl)methyl]-5H-pyrido[3,2-b]indol-3-yl]propan-2-ol, 2-[7-(dimethyl-1H-1,2,3-triazol-5-yl)-8-fluoro-5-[(S)-(2-fluorophenyl)(oxan-4-yl)methyl]-5H-pyrido[3,2-b]indol-3-yl]propan-2-ol, 2-{8-fluoro-5-[(S)-(2-fluorophenyl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, 1-cyclopropyl-1-[7-(dimethyl-1H-1,2,3-triazol-5-yl)-8-fluoro-5-[(S)-(2-fluorophenyl)(oxan-4-yl)methyl]-5H-pyrido[3,2-b]indol-3-yl]ethan-1-ol, Diastereomer 1, 1-cyclopropyl-1-[7-(dimethyl-1H-1,2,3-triazol-5-yl)-8-fluoro-5-[(S)-(2-fluorophenyl)(oxan-4-yl)methyl]-5H-pyrido[3,2-b]indol-3-yl]ethan-1-ol, Diastereomer 2, 5-{8-fluoro-5-[(S)-(2-fluorophenyl)(oxan-4-yl)methyl]-3-methanesulfonyl-5H-pyrido[3,2-b]indol-7-yl}-1,4-dimethyl-1H-1,2,3-triazole, 5-{3-methanesulfonyl-5-[(S)-oxan-4-yl(phenyl)methyl]-5H-pyrido[3,2-b]indol-7-yl}-1,4-dimethyl-1H-1,2,3-triazole, 5-{3-methanesulfonyl-5-[(S)-oxan-4-yl(phenyl)methyl]-5H-pyrido[3,2-b]indol-7-yl}-4-($^2$H$_3$)methyl-1-methyl-1H-1,2,3-triazole, 5-{8-fluoro-5-[(S)-(2-fluorophenyl)(oxan-4-yl)methyl]-3-methanesulfonyl-5H-pyrido[3,2-b]indol-7-yl}-4-($^2$H$_3$)methyl-1-methyl-1H-1,2,3-triazole, 7-(dimethyl-1H-1,2,3-triazol-5-yl)-5-[(S)-(2-fluorophenyl)(oxan-4-yl)methyl]-5H-pyrido[3,2-b]indole-3-carboxylic acid, 2-{8-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer A, 2-{8-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer B, 2-{8-fluoro-7-[4-($^2$H$_3$)methyl-1-methyl-1H-1,2,3-triazol-5-yl]-5-[(S)-oxan-4-yl(phenyl)methyl]-5H-pyrido[3,2-b]indol-3-yl}propan-2-ol, 2-{8-fluoro-7-[5-($^2$H$_3$)methyl-3-methyl-1,2-oxazol-4-yl]-5-[(S)-oxan-4-yl(phenyl)methyl]-5H-pyrido[3,2-b]indol-3-yl}propan-2-ol, 2-{8-fluoro-5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer A, 2-{8-fluoro-5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer B, 2-{8-fluoro-7-[4-($^2$H$_3$)methyl-1-methyl-1H-1,2,3-triazol-5-yl]-5-[oxan-4-yl(pyridin-2-yl)methyl]-5H-pyrido[3,2-b]indol-3-yl}propan-2-ol, Entantiomer A, 2-{8-fluoro-7-[4-($^2$H$_3$)methyl-1-methyl-1H-1,2,3-triazol-5-yl]-5-[oxan-4-yl(pyridin-2-yl)methyl]-5H-pyrido[3,2-b]indol-3-yl}propan-2-ol, Entantiomer B, 2-{8-fluoro-5-[1-(3-fluoropyridin-2-yl)butyl]-7-[4-($^2$H$_3$)methyl-1-methyl-1H-1,2,3-triazol-5-yl]-5H-pyrido[3,2-b]indol-3-yl}propan-2-ol, Entantiomer A, 2-{8-fluoro-5-[1-(3-fluoropyridin-2-yl)butyl]-7-[4-($^2$H$_3$)methyl-1-methyl-1H-1,2,3-triazol-5-yl]-5H-pyrido[3,2-b]indol-3-yl}propan-2-ol, Entantiomer B, 2-{8-fluoro-5-[(3-methoxypyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer A, 2-{8-fluoro-5-[(3-methoxypyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer B, 2-{8-fluoro-7-[4-($^2$H$_3$)methyl-1-methyl-1H-1,2,3-triazol-5-yl]-5-[(3-methylpyridin-2-yl)(oxan-4-yl)methyl}-5H-pyrido[3,2-b]indol-3-yl}propan-2-ol, Entantiomer A, 2-{8-fluoro-7-[4-($^2$H$_3$)methyl-1-methyl-1H-1,2,3-triazol-5-yl]-5-[(3-methylpyridin-2-yl)(oxan-4-yl)methyl}-5H-pyrido[3,2-b]indol-3-yl}propan-2-ol, Entantiomer B, 2-{8-fluoro-5-[(5-fluoropyridin-2-yl)(oxan-4-yl)methyl}-7-[4-($^2$H$_3$)methyl-1-methyl-1H-1,2,3-triazol-5-yl]-5H-pyrido[3,2-b]indol-3-yl]propan-2-ol, Entantiomer A, 2-{8-fluoro-5-[(5-fluoropyridin-2-yl)(oxan-4-yl)methyl}-7-[4-($^2$H$_3$)methyl-1-methyl-1H-1,2,3-triazol-5-yl]-5H-pyrido[3,2-b]indol-3-yl]propan-2-ol, Entantiomer B, 2-{8-fluoro-7-[4-($^2$H$_3$)methyl-1-methyl-1H-1,2,3-triazol-5-yl}-5-[oxan-4-yl)pyrimidin-2-yl)methyl]-5H-pyrido[3,2-b]indol-3-yl]propan-2-ol, Entantiomer A, 2-{8-fluoro-7-[4-($^2$H$_3$)methyl-1-methyl-1H-1,2,3-triazol-5-yl]-5-[oxan-4-yl(pyrimidin-2-yl)methyl]-5H-pyrido[3,2-b]indol-3-yl}propan-2-ol, Entantiomer B, 2-{8-fluoro-7-[4-($^2$H$_3$)methyl-1-methyl-1H-1,2,3-triazol-5-yl]-5-[1-(pyridin-2-yl)butyl]-5H-pyrido[3,2-b]indol-3-yl}propan-2-ol, Entantiomer A, 2-{8-fluoro-7-[4-($^2$H$_3$)methyl-1-methyl-1H-1,2,3-triazol-5-yl]-5-[1-(pyridin-2-yl)butyl]-5H-pyrido[3,2-b]indol-3-yl}propan-2-ol, Entantiomer B, 2-{8-fluoro-5-[(4-methoxypyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer A, 2-{8-fluoro-5-[(4-methoxypyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer B, 2-{8-fluoro-7-[4-($^2$H$_3$)methyl-1-methyl-1H-1,2,3-triazol-5-yl]-5-[(4-methylpyridin-2-yl)(oxan-4-yl)methyl]-5H-pyrido[3,2-b]indol-3-yl}propan-2-ol, Entantiomer A, 2-{8-fluoro-7-[4-($^2$H$_3$)methyl-1-methyl-1H-1,2,3-triazol-5-yl]-5-[(4-methylpyridin-2-yl)(oxan-4-yl)methyl]-5H-pyrido[3,2-b]indol-3-yl}propan-2-ol, Entantiomer B, 2-[7-(dimethyl-1H-1,2,3-triazol-5-yl)-8-fluoro-5-[oxan-4-yl)pyrimidin-2-yl)methyl]-5H-pyrido[3,2-b]indol-3-yl]propan-2-ol, Entantiomer A, 2-[7-(dimethyl-1H-1,2,3-triazol-5-yl)-8-fluoro-5-[oxan-4-yl)pyrimidin-2-yl)methyl]-5H-pyrido[3,2-b]indol-3-yl]propan-2-ol, Entantiomer B, 2-{8-fluoro-7-[4-($^2$H$_3$)methyl-1-methyl-1H-1,2,3-triazol-5-yl]-5-[(5-methylpyridin-2-yl)(oxan-4-yl)methyl]-5H-pyrido[3,2-b]indol-3-yl}propan-2-ol, Entantiomer A, 2-{8-fluoro-7-[4-($^2$H$_3$)methyl-1-methyl-1H-1,2,3-triazol-5-yl]-5-[(5-methylpyridin-2-yl)(oxan-4-yl)methyl]-5H-pyrido[3,2-b]indol-3-yl}propan-2-ol, Entantiomer B, 2-{8-fluoro-5-[1-(5-fluoropyridin-2-yl)butyl]-7-[4-($^2$H$_3$)methyl-1-methyl-1H-1,2,3-triazol-5-yl]-5H-pyrido[3,2-b]indol-3-yl}propan-2-ol, Entantiomer A, 2-{8-fluoro-5-[1-(5-fluoropyridin-2-yl)butyl]-7-[4-($^2$H$_3$)methyl-1-methyl-1H-1,2,3-triazol-5-yl]-5H-pyrido[3,2-b]indol-3-yl}propan-2-ol, Entantiomer B, 2-{8-fluoro-5-[(4-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, 2-{5-[5,6-dihydro-2H-pyran-3-yl(phenyl)methyl]-8-fluoro-7-[4-($^2$H$_3$)methyl-1-methyl-1H-1,2,3-triazol-5-yl]-5H-pyrido[3,2-b]indol-3-yl}propan-2-ol, 2-[8-fluoro-5-(3-methoxy-1-phenylpropyl)-7-[4-($^2$H$_3$)methyl-1-methyl-1H-1,2,3-triazol-5-yl]-5H-pyrido[3,2-b]indol-3-yl]propan-2-ol, Entantiomer A, 2-[8-fluoro-5-(3-methoxy-1-phenylpropyl)-7-[4-($^2$H$_3$)methyl-1-methyl-1H-1,2,3-triazol-5-yl]-5H-pyrido[3,2-b]indol-3-yl]propan-2-ol, Entantiomer A, 2-{8-fluoro-7-[4-($^2$H$_3$)methyl-1-methyl-1H-1,2,3-triazol-5-yl]-5-[(3-methyloxetan-3-yl)(phenyl)methyl]-5H-pyrido[3,2-b]indol-3-yl}propan-2-ol, Entantiomer A, 2-{8-fluoro-7-[4-($^2$H$_3$)methyl-1-methyl-1H-1,2,3-triazol-5-yl]-5-[(3-methyloxetan-3-yl)(phenyl)methyl]-5H-pyrido[3,2-b]indol-3-yl}propan-2-ol, Entantiomer A, 2-{8-fluoro-7-[4-($^2$H$_3$)methyl-1-methyl-1H-1,2,3-triazol-5-yl]-5-[2-(oxetan-3-yl)-1-phenylethyl]-5H-pyrido[3,2-b]indol-3-yl}propan-2-ol, 2-{8-fluoro-7-[4-($^2$H$_3$)methyl-1-methyl-1H-1,2,3-triazol-5-yl]-5-[oxetan-3-yl(phenyl)methyl]-5H-pyrido[3,2-b]indol-3-yl}propan-2-ol, Entantiomer A, 2-{8-fluoro-7-[4-($^2$H$_3$)methyl-1-methyl-1H-1,2,3-triazol-5-yl]-5-[oxetan-3-yl(phenyl)methyl]-5H-pyrido[3,2-b]indol-3-yl}propan-2-ol, Entantiomer A, 2-[7-(dimethyl-1H-1,2,3-triazol-5-yl)-8-fluoro-5-[(5-fluoropyridin-2-yl)(oxan-4-yl)methyl]-5H-pyrido[3,2-b]indol-3-yl]propan-2-ol, Entantiomer A, 2-[7-(dimethyl-1H-1,2,3-triazol-5-yl)-8-fluoro-5-[(5-fluoropyridin-2-yl)(oxan-4-yl)methyl]-5H-pyrido[3,2-b]indol-3-yl]propan-2-ol, Entantiomer B, 2-{5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer A, 2-{5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer B, 2-{5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer A, 2-{5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer B, 2-{8-chloro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer A, 2-{8-chloro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer B, 2-{8-chloro-7-[4-($^2$H$_3$)methyl-1-methyl-1H-1,2,3-triazol-5-yl]-5-[(S)-oxan-4-yl(phenyl)methyl]-5H-pyrido[3,2-b]indol-3-yl}propan-2-ol, 2-{8-chloro-5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer A, 2-{8-chloro-5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer B, 2-{8-chloro-7-[4-($^2$H$_3$)methyl-1-methyl-1H-1,2,3-triazol-5-yl]-5-[oxan-4-yl(pyridin-2-yl)methyl]-5H-pyrido[3,2-b]indol-3-yl}propan-2-ol, Entantiomer A, 2-{8-chloro-7-[4-($^2$H$_3$)methyl-1-methyl-1H-1,2,3-triazol-5-yl]-5-[oxan-4-yl(pyridin-2-yl)methyl]-5H-pyrido[3,2-b]indol-3-yl}propan-2-ol, Entantiomer B, 2-{8-chloro-5-[1-(3-fluoropyridin-2-yl)butyl]-7-[4-($^2$H$_3$)methyl-1-methyl-1H-1,2,3-triazol-5-yl]-5H-pyrido[3,2-b]indol-3-yl}propan-2-ol, Entantiomer A, 2-{8-chloro-5-[1-(3-fluoropyridin-2-yl)butyl]-7-[4-($^2$H$_3$)methyl-1-methyl-1H-1,2,3-triazol-5-yl]-5H-pyrido[3,2-b]indol-3-yl}propan-2-ol, Entantiomer B, 2-{6-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer A, 2-{6-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, Entantiomer B, or a pharmaceutically acceptable salt, tautomer or stereoisomer thereof.

One embodiment of the invention provides compounds wherein A is

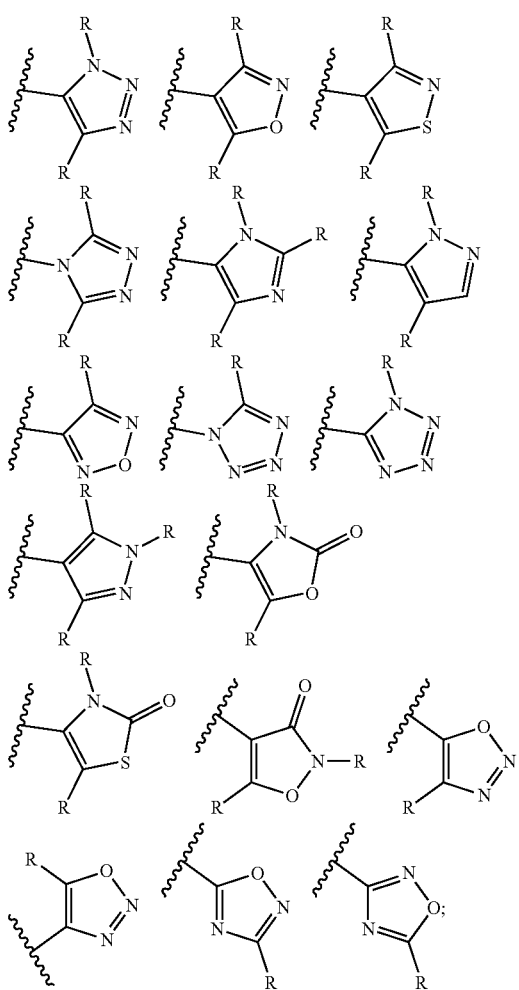

and R is independently one or more hydrogen, CD$_3$, OCD$_3$, CF$_3$, CHF$_2$ or (C$_1$-C$_3$)alkyl.

Another embodiment of the invention provides compounds wherein A is

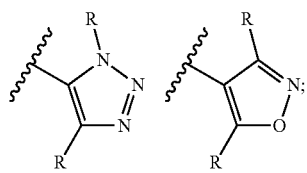

and R is independently one or more hydrogen, CD$_3$, OCD$_3$, CF$_3$, CHF$_2$ or (C$_1$-C$_3$)alkyl.

Another embodiment of the invention provides compounds wherein A is

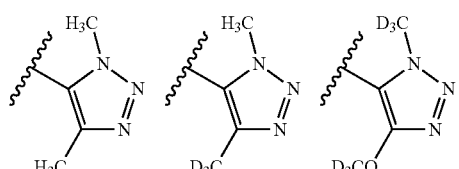

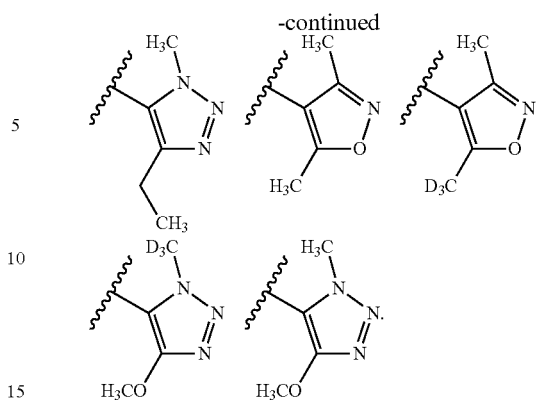

Other Embodiments of the Invention

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for inhibiting activity of a bromodomain-containing protein mediated disorder in a patient in need thereof comprising the step of administering to said patient at least one compound of the invention.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including without limitation, small cell lung cancer, non-small cell lung cancer, colorectal cancer, multiple myeloma, acute myeloid leukemia (AML), acute lymphoblastic leukemia (ALL), pancreatic cancer, liver cancer, hepatocellular cancer, neuroblastoma, other solid tumors or other hematological cancers.

In another embodiment, the invention provides a method for the treatment and/or prophylaxis of various types of cancer, including without limitation, small cell lung cancer, non-small cell lung cancer, colorectal cancer, multiple myeloma or AML.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a method of inhibiting a bromodomain-containing protein comprising contacting said protein with any exemplified compound or a pharmaceutically acceptable salt or composition thereof.

Therapeutic Applications

The compounds of formula (I) of the invention are bromodomain inhibitors and have potential utility in the treatment of diseases and conditions for which a bromodomain inhibitor is indicated.

In one embodiment there is provided a method for the treatment of a disease or condition, for which a bromodomain inhibitor is indicated, in a subject in need thereof which comprises administering a therapeutically effective amount of compound of formula (I) or a pharmaceutically acceptable salt thereof.

In another embodiment there is provided a method for treatment of a chronic autoimmune and/or inflammatory condition, in a subject in need thereof which comprises administering a therapeutically effective amount of one or more compounds of formula (I) or a pharmaceutically acceptable salt thereof.

In a further embodiment there is provided a method for treatment of cancer in a subject in need thereof which comprises administering a therapeutically effective amount of one or more compounds of formula (I) or a pharmaceutically acceptable salt thereof.

In one embodiment the subject in need thereof is a mammal, particularly a human.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebrovascular ischaemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma and cardiac fibrosis.

Bromodomain inhibitors may be useful in the prevention and treatment of viral infections such as herpes virus, human papilloma virus, adenovirus, poxvirus and other DNA viruses.

Bromodomain inhibitors may also be useful in the treatment of cancer, including hematological, epithelial including lung, breast and colon carcinomas, midline carcinomas, mesenchymal, hepatic, renal and neurological tumours.

In one embodiment the disease or condition for which a bromodomain inhibitor is indicated is selected from diseases associated with systemic inflammatory response syndrome, such as sepsis, burns, pancreatitis, major trauma, hemorrhage and ischemia. In this embodiment, the bromodomain inhibitor would be administered at the point of diagnosis to reduce the incidence of SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, hemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxemia. In another embodiment, the bromodomain inhibitor is indicated for the treatment of acute or acute on chronic pancreatitis. In another embodiment the bromodomain inhibitor is indicated for the treatment of burns.

In one embodiment the disease or condition for which bromodomain inhibitor is indicated is selected from herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus.

The term "diseases or conditions for which a bromodomain inhibitor is indicated" is intended to include any of or all of the above disease states.

In one embodiment, there is provided a method for inhibiting a bromodomain which comprises contacting the bromodomain with a compound of formula (I) or a pharmaceutically acceptable salt thereof.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjogren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-ß, VEGF, and other immunosuppressive cytokines) or a cytokine that stimulates T cell activation, for stimulating an immune response.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO₂NH₂, substituted sulfonamido, nitro, cyano, carboxy, carbamyl, e.g. —CONH₂, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (—) that is not between two letters or symbols; this is used to indicate a point of attachment for a substituent. For example, —CONH₂ is attached through the carbon atom.

Additionally, for purposes of clarity, when there is no substituent shown at the end of a solid line, this indicates that there is a methyl (CH₃) group connected to the bond.

As used herein, the term "alkyl" or "alkylene" is intended to include both branched and straight-chain saturated aliphatic hydrocarbon groups having the specified number of carbon atoms. For example, "C₁-C₆ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C₂-C₈ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "C₂-C₈ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an O-alkyl group. "C₁₋₆ alkoxy" (or alkyloxy), is intended to include C₁, C₂, C₃, C₄, C₅, and C₆ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

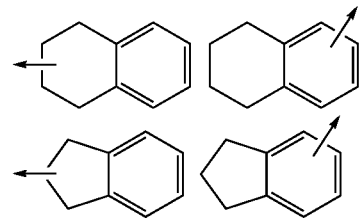

Arrowed lines drawn from the ring system indicate that the bond may be attached to any of the suitable ring atoms.

The term "cycloalkyl" refers to cyclized alkyl groups. C₃₋₆ cycloalkyl is intended to include C₃, C₄, C₅, and C₆ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$ wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the core of the compound.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl$)_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as [1]H (hydrogen), [2]H (deuterium) and [3]H (tritium). They are also commonly denoted as D for deuterium and T for tritium. In the application, $CD_3$ denotes a methyl group wherein all of the hydrogen atoms are deuterium. Isotopes of carbon include $^{13}$C and [14]C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988);
e) Kakeya, N. et al., *Chem. Pharm. Bull.*, 32:692 (1984); and
f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated by reference in their entirety.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein, the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

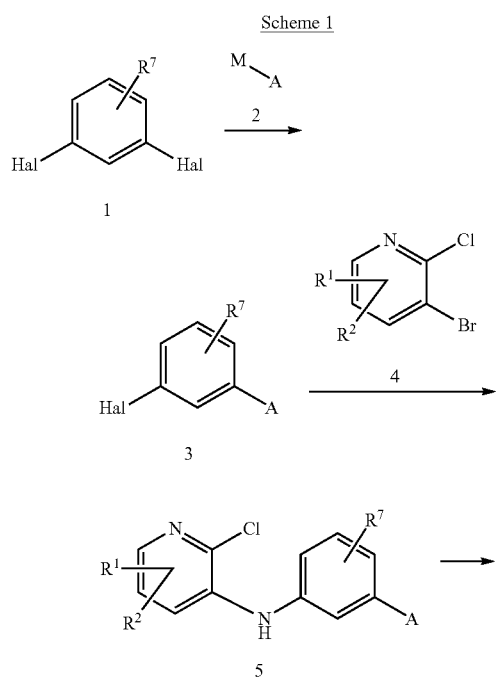

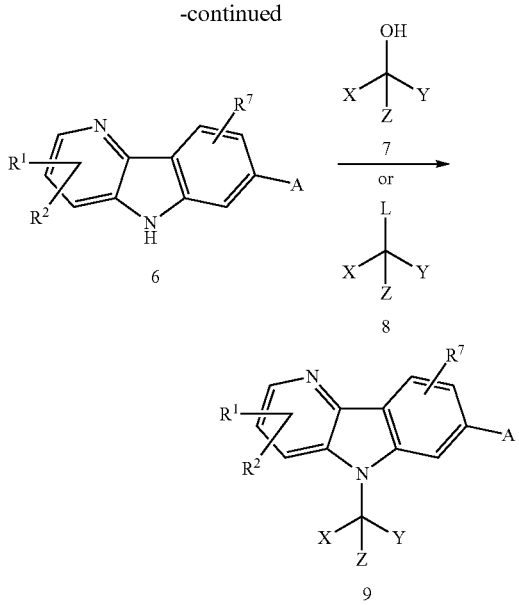

General routes to compounds described in the invention are illustrated in Schemes 1-8, where the $R^1$, $R^2$, X, Y, Z and A substituents are defined previously in the text or a functional group that can be converted to the desired final substituent. The substituent Hal is a halide. L is a leaving group such as a halide or OH that can be easily converted to a leaving group such as a triflate. As shown in Scheme 1, a general procedure for the preparation of compounds of the invention involves starting with the substituted aniline 1. Coupling of 1 with the aromatic heterocycle A (2, where M is a suitable coupling partner, such as boronic acid, boronic ester, or stannane) using a suitable catalyst can yield functionalized anilines 3. For example, 3 could arise from a Suzuki coupling reaction between 5-bromo-3-aminobenzonitrile or 3-bromo-aniline and a heteroaromatic boronic acid using $PdCl_2$(dppf) as a catalyst. Subsequent coupling to give the diaryl amine 5 can be achieved using a Buchwald N-arylation reaction with pyridine 4. Subsequent cyclization to give the functionalized carboline 6 can be achieved using a variety of conditions known in the literature. For example, chloropyridine 5 can undergo a palladium-catalyzed cyclization employing a catalyst such as $PdCl_2(PPh_3)_2$ and a base such as NaOAc in a suitable solvent such as DMA at an elevated temperature, such as 180° C. In the final step, the carboline nitrogen can be substituted under Mitsunobu conditions using triphenylphosphine and diisopropyl azodicarboxylate (DIAD) with alcohol 7. Alternatively, functionalized carboline 9 can be generated from a displacement reaction between the carboline 6 and an alkylating agent 8, where L is a leaving group such as a halide, mesylate or triflate, in the presence of a base, such as potassium carbonate. In cases where 9 is a racemate, chiral separation can provide enantiomerically pure products. Further derivatization of $R^1$ and $R^2$ can provide additional compounds of the invention. For example, when $R^1$ is an ester, addition of a Grignard reagent or an alkyl lithium can generate tertiary alcohols. The same $R^1$ ester could instead be hydrolyzed using, for example, sodium hydroxide to give a carboxylic acid ($R^1$=$CO_2H$) as the final substituent.

Scheme 2

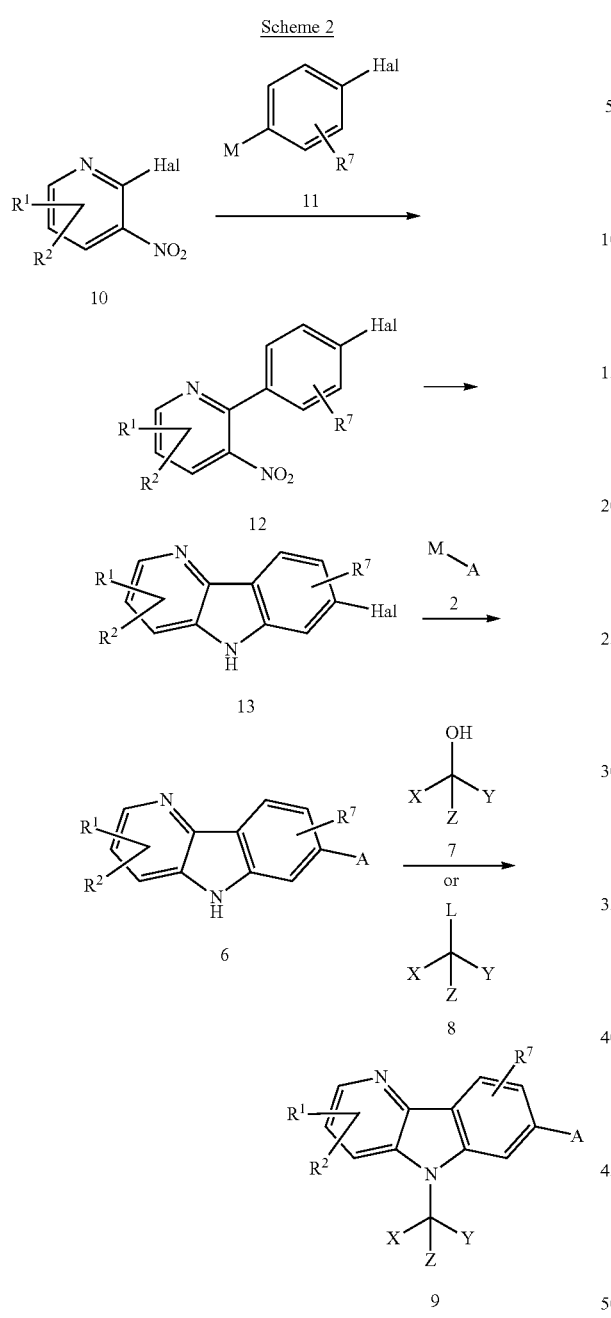

5,5-tetramethyl-1,3,2-dioxaborolan-2-yl)phenyl)carbamate under typical Suzuki coupling conditions as discussed above to afford compound 12 where Hal is a NHBoc moiety. After further manipulations, this NHBoc can be deprotected under standard conditions known to one skilled in the art, such as with TFA in DCM, then converted through a diazotization reaction to the required halogen, such as a bromine.

Scheme 3

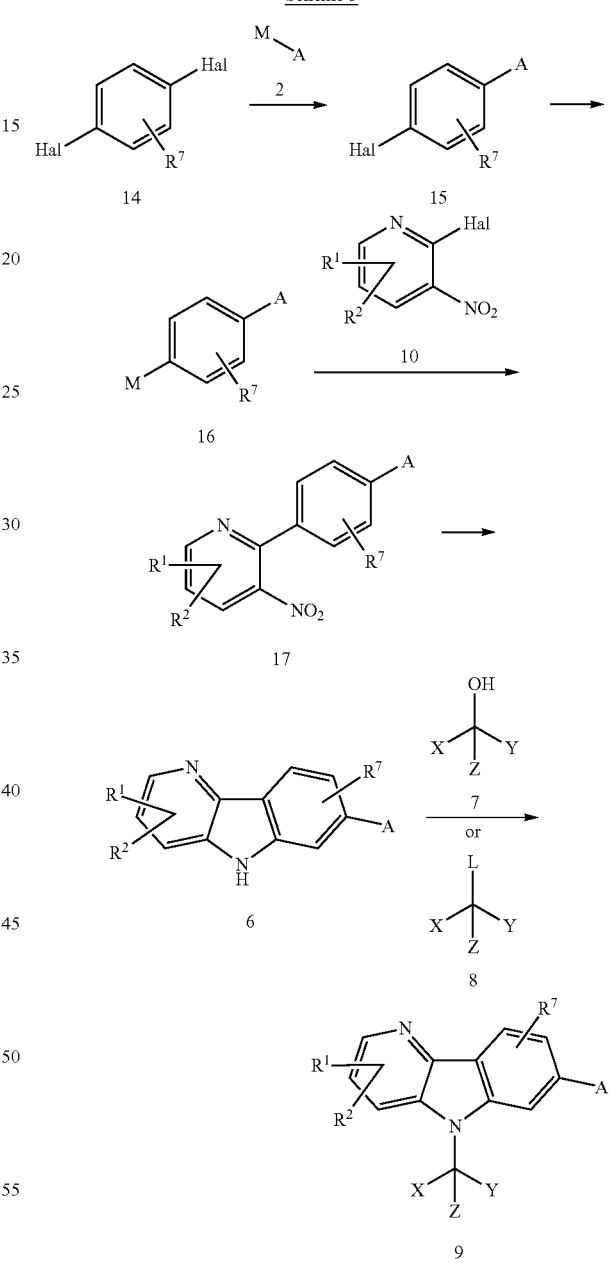

Examples of the invention can also be prepared as outlined in Scheme 2. Compound 12 can be prepared using coupling methods known to one skilled in the art. For example, a compound such as 2-chloro-3-nitropyridine can be coupled to a suitably derivatized aryl 11 where M is a boronic acid under standard Suzuki coupling conditions. Subsequent cyclization can be effected under conditions such as with triphenyl phosphine or DPPE in a solvent such as 1,2-dichlorobenzene at elevated temperatures to give carboline 13. The remainder of the synthesis employs conditions as discussed in Scheme 1.

In a similar approach, compound 11 could contain a functional group that could eventually be converted to a halogen. For example, if compound 10 were 2,5-dibromo-3-nitropyridine, it could be coupled with tert-butyl (4-(4,4, Compounds of the invention can also be prepared by altering the steps of the synthesis. For example, the aromatic heterocycle A could be installed earlier in the sequence, as shown in the transformation of 14 to 15. Using methods previously discussed, compound 15 can be prepared and functional groups modified to set up for further elaboration. For example, a compound such as 4-bromo-2-fluoro-iodobenzene can be coupled with 2 to afford compound 15.

Conversion of the bromine of 15 to a boronic acid can be effected in several ways known to one skilled in the art, for example treating compound 15 with n-BuLi at low temperatures such as −78° C. in a suitable solvent such as THF, then treating that mixture with trimethylborate followed by standard workup. The conversion from Hal (in 15) to M (in 16) can also be accomplished using palladium catalysis in the presence of a diboronate to increase functional group compatibility. The resulting compound 16 can then be further elaborated as shown in Scheme 3 using methodologies previously discussed in Schemes 1 and 2.

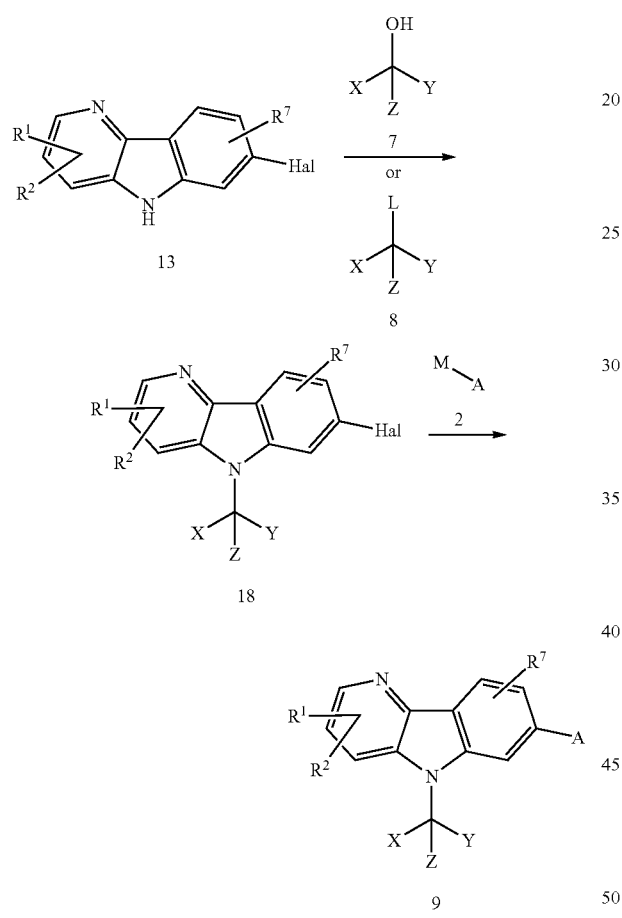

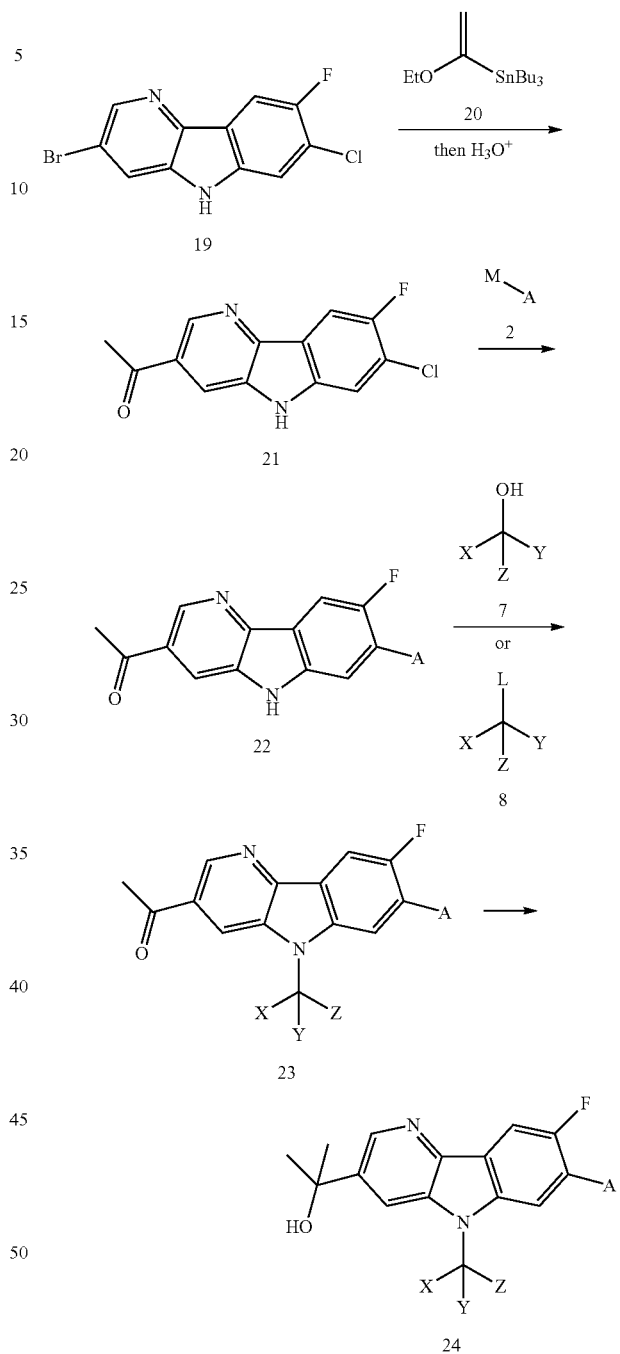

A fourth exemplary method is shown in Scheme 4. Alternately, the nitrogen of intermediate 13 can be first substituted under Mitsunobu conditions with alcohol 7 or with alkylating agent 8, where L is a leaving group such as a halide, mesylate or triflate, in the presence of a base, such as potassium carbonate to give intermediate 18. Then coupling of 18 with the aromatic heterocycle A (2, where M is a suitable coupling partner, such as boronic acid, boronic ester or stannane) using a suitable catalyst then generates the final tricyclic 9. Intermediate 18 can also be directly coupled with a suitable aromatic heterocycle A (2, where M is H), via palladium-mediated C—H activation to afford compounds 9.

Compound 19 is a specific embodiment of compound 13 and is shown in Scheme 5. The bromide of 19 can be selectively functionalized in a Stille reaction with stannane 20 which upon hydrolysis gives ketone 21. The chloride can then be elaborated as outlined previously to afford 22. Carboline 22 can be functionalized as outlined in Scheme 1 to afford 23. The ketone of 23 can be functionalized in a number of ways using methods known to one skilled in the art to give additional Formula (I) compounds. For instance, ketone 23 can be treated with methyllithium or methylmagnesium bromide to give carbinol 24.

Scheme 6

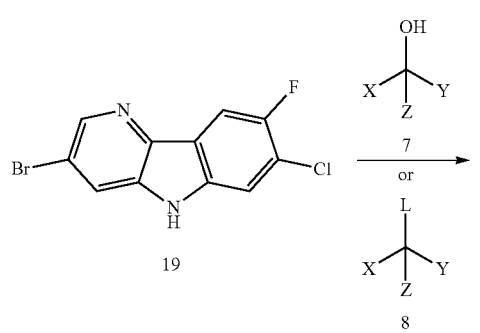

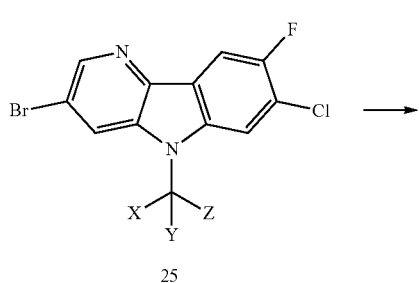

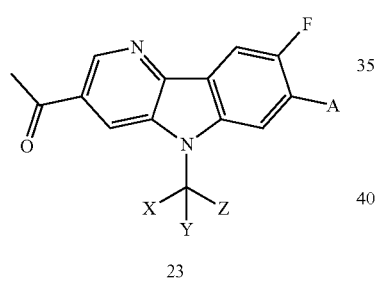

In certain instances, it may be preferable to first alkylate compound 19 as described in Scheme 1 to afford compound 25. As described in Scheme 5, the bromide can be selectively elaborated in a Stille reaction, followed by a palladium-mediated cross-coupling reaction of the chloride to afford compound 23. The ketone of 23 can be functionalized in a number of ways using methods known to one skilled in the art to give additional Formula (I) compounds.

Scheme 7

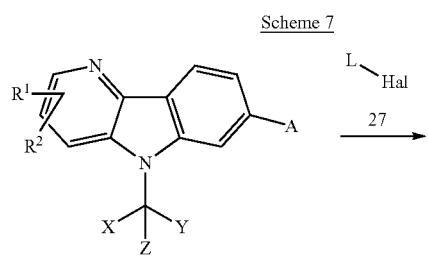

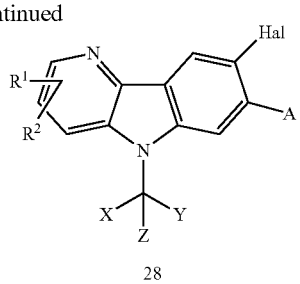

Compound 26 is a specific embodiment of compound 9 and is shown in Scheme 7. In some instances, it is possible to halogenate at C-8 of the carboline, using electrophilic halogenating reagents such as N-halosuccinimides or Select-fluor® to afford compound 28. The halide of compound 28 can be further elaborated using methods known to one skilled in the art to give additional Formula (I) compounds.

Scheme 8

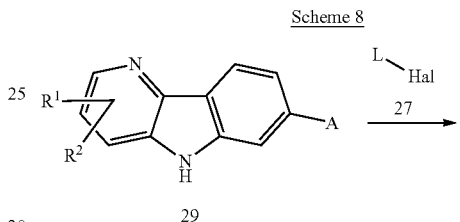

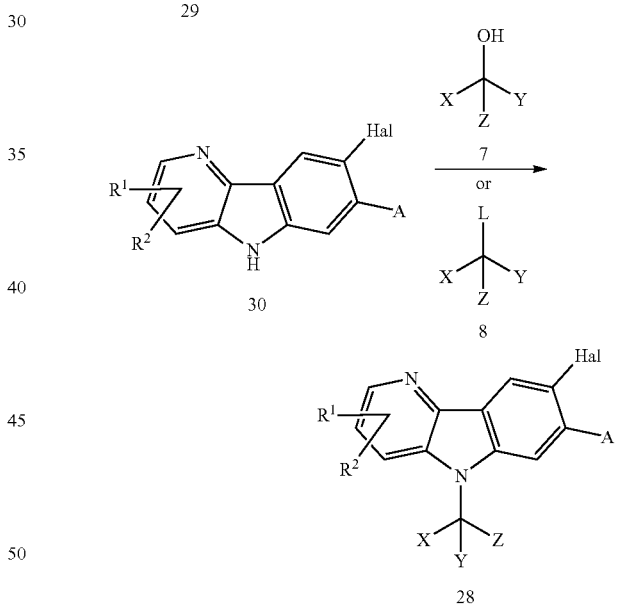

Compound 29 is a specific embodiment of compound 6 and is shown in Scheme 8. In some instances, it is possible to halogenate at C-8 of the carboline, using electrophilic halogenating reagents such as N-halosuccinimides or Select-fluor® to afford compound 30. Carboline 30 can be functionalized as outlined in Scheme 1 to afford 28. The halide of compound 28 can be further elaborated using methods known to one skilled in the art to give additional Formula (I) compounds.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

Abbreviations

| | |
|---|---|
| MeCN | Acetonitrile |
| AcOH | acetic acid |
| AlMe$_3$ | trimethyl aluminum |
| aq | Aqueous |
| Bn | Benzyl |
| Boc | tert-butoxycarbonyl |
| Boc$_2$O | di-tert-butyl dicarbonate |
| CBz | benzyloxycarbonyl |
| DCC | 1,3-dicyclohexylcarbodiimide |
| DCM | dichloromethane |
| DDQ | 2,3-dichloro-5,6-dicyano-1,4-benzoquinone |
| DIAD | diisopropyl azodicarboxylate |
| DIEA | diisopropylethylamine |
| DMAP | 4-dimethylaminopyridine |
| DMA | dimethylacetamide |
| DME | dimethoxyethane |
| DMF | dimethylformamide |
| DMSO | dimethyl sulfoxide |
| EDC | 1-(3-dimethylaminopropyl)-3-ethylcarbodiimide hydrochloride |
| Et$_2$AlCl | diethyl aluminum chloride |
| Et$_3$N | triethyl amine |
| Et$_2$O | diethyl ether |
| EtOH | Ethanol |
| EtOAc | ethyl acetate |
| equiv. | equivalent(s) |
| g | gram(s) |
| h or hr | hour(s) |
| HOBt | hydroxybenzotriazole |
| HPLC | high pressure liquid chromatography |
| iPrOH | isopropyl alcohol |
| KOtBu | potassium tert-butoxide |
| LCMS | Liquid Chromatography-Mass Spectroscopy |
| LDA | lithium diisopropylamide |
| LiHMDS | lithium bis(trimethylsilyl)amide |
| Me | Methyl |
| MeI | methyl iodide |
| MeOH | Methanol |
| min | minute(s) |
| mL | milliliter(s) |
| mmol | millimole |
| MTBE | methyl t-butyl ether |
| NaHMDS | sodium bis(trimethylsilyl)amide |
| n-BuLi | n-butyl lithium |
| NH$_4$OAc | ammonium acetate |
| NMP | N-methylpyrrolidinone |
| Pd(OAc)$_2$ | palladium acetate |
| Pd(dppf)Cl$_2$ | [1,1'-bis(diphenylphosphino)ferrocene]dichloropalladium(II) |
| RT or Rt or T$_R$ | retention time |
| sat | Saturated |
| SFC | Supercritical fluid chromatography |
| t-Bu | tertiary butyl |
| t-BuLi | t-butyl lithium |
| t-BuOH | tertiary butyl alcohol |
| t-BuOMe | tert-butyl methyl ether |
| TBTU | O-(1H-benzotriazol-1-yl)-N,N,N',N'-tetramethyluronium tetrafluoroborate |
| TCTU | O-(1H-6-chlorobenzotriazol-1-yl)-N,N,N',N'-tetramethyluronium tetrafluoroborate |
| TEA | Triethylamine |
| TFA | trifluoroacetic acid |
| Tf$_2$O | trifluoromethylsulfonic anhydride |
| THF | Tetrahydrofuran |

Example 1

5-Benzyl-7-(dimethyl-1,2-oxazol-4-yl)-2-methyl-5H-pyrido[3,2-b]indole-9-carboxamide

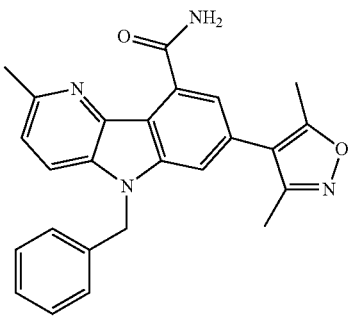 [SMILES: Cc1ccc2c(n1)c1c(C(N)=O)cc(-c3c(C)noc3C)cc1n2Cc1ccccc1]

Step 1: 3-Amino-5-bromobenzonitrile

A flask containing 3-bromo-5-nitrobenzonitrile (3 g, 13.2 mmol) in MeOH (100 mL) was cooled in an ice-water bath. To the solution was added zinc (3.46 g, 52.9 mmol) and acetic acid (6.05 mL, 106 mmol). After a minute, an exotherm was observed. After 2 h, the reaction mixture was filtered through celite and the filtrate concentrated. The resulting residue was purified by silica gel chromatography using 0 to 50% ethyl acetate in hexanes. The product containing fractions were combined and evaporated to give 3-amino-5-bromobenzonitrile (2.1 g, 81%): HPLC: RT=0.80 min (Waters Acquity UPLC BEH C18 1.7 um 2.0×50 mm, CH$_3$CN/H$_2$O/0.05% TFA, 1 min gradient, wavelength=254 nm); MS (ES): m/z=196.9/198.9 $^{79}$Br/$^{81}$Br [M+1]$^+$; $^1$H NMR (DMSO-d$_6$) δ: 7.06-7.09 (m, 1H), 7.04 (t, J=2.0 Hz, 1H), 6.87 (dd, J=2.1, 1.4 Hz, 1H), 5.91 (s, 2H).

Step 2:
3-Amino-5-(3,5-dimethylisoxazol-4-yl)benzonitrile

To a 40 mL vial was added (3,5-dimethylisoxazol-4-yl) boronic acid (1 g, 7.10 mmol), 3-amino-5-bromobenzonitrile (1.165 g, 5.91 mmol), PdCl$_2$(dppf) CH$_2$Cl$_2$ adduct (0.097 g, 0.118 mmol), tetrahydrofuran (6 mL), 3 M aqueous potassium phosphate (5.91 mL, 17.7 mmol) and degassed with argon. The vial was capped and heated at 65° C. for 3 h. The reaction mixture was cooled to room temperature and partitioned between water and ethyl acetate. The organic layer was washed with brine, dried over sodium sulfate and concentrated. The crude product was purified by silica gel chromatography using 0-100% ethyl acetate in hexanes, to obtain 3-amino-5-(3,5-dimethylisoxazol-4-yl)benzonitrile (0.327 g, 26%) and recovered 3-amino-5-bromobenzonitrile (0.6 g): HPLC: RT=0.74 min (Waters Acquity UPLC BEH C18 1.7 um 2.0×50 mm, CH$_3$CN/H$_2$O/0.05% TFA, 1 min gradient, wavelength=254 nm); MS (ES): m/z=214.0 [M+1]$^+$.

Step 3: 3-((2-Chloro-6-methylpyridin-3-yl)amino)-5-(3,5-dimethylisoxazol-4-yl)benzonitrile To a vial containing 3-amino-5-(3,5-dimethylisoxazol-4-yl)benzonitrile (80 mg, 0.375 mmol) was added toluene (2 mL), 3-bromo-2-chloro-6-methylpyridine (85 mg, 0.413 mmol), cesium carbonate (244 mg, 0.750 mmol) and chloro (2-dicyclohexylphosphino-2',4',6'-triisopropyl-1,1'-biphenyl)[2-(2'-amino-1,1'-biphenyl)]palladium(II) (CAS #1310584-14-5, 7.4 mg, 9.38 µmol). The reaction mixture was degassed by bubbling argon through the reaction mixture. The vial was capped with a pressure safe septum screw-cap and heated at 100° C. After 5 h, the reaction mixture was cooled, diluted with dichloromethane, and filtered through celite. The filtrate was concentrated and purified by silica gel chromatography to give 3-((2-chloro-6-methylpyridin-3-yl)amino)-5-(3,5-dimethylisoxazol-4-yl) benzonitrile (29 mg, 23%): HPLC: RT=0.93 min (Waters Acquity UPLC BEH C18 1.7 um 2.0×50 mm, CH$_3$CN/H$_2$O/ 0.05% TFA, 1 min gradient, wavelength=254 nm); MS (ES): m/z=339.1/340.9 $^{35}$Cl/$^{37}$Cl [M+1]$^+$.

Step 4: 7-(3,5-Dimethylisoxazol-4-yl)-2-methyl-5H-pyrido[3,2-b]indole-9-carbonitrile To a microwave vial was added sodium acetate trihydrate (29.1 mg, 0.214 mmol), bis(triphenylphosphine)palladium (II) chloride (12.0 mg, 0.017 mmol), followed by a solution of 3-((2-chloro-6-methylpyridin-3-yl)amino)-5-(3,5-dimethylisoxazol-4-yl)benzonitrile (29 mg, 0.086 mmol) in dimethylacetamide (1 mL). The reaction mixture was degassed by bubbling argon through the reaction mixture. The vial was heated in a microwave at 180° C. for 1 h. The reaction mixture was concentrated and the residue was purified by silical gel chromatography using ethyl acetate in dichloromethane. The product fractions were combined and concentrated to give 7-(3,5-dimethylisoxazol-4-yl)-2-methyl-5H-pyrido[3,2-b]indole-9-carbonitrile (7 mg, 27%): HPLC: RT=0.75 min (Waters Acquity UPLC BEH C18 1.7 um 2.0×50 mm, CH$_3$CN/H$_2$O/0.05% TFA, 1 min gradient, wavelength=254 nm); MS (ES): m/z=303.1 [M+1]$^+$.

Step 5: 5-Benzyl-7-(3,5-dimethylisoxazol-4-yl)-2-methyl-5H-pyrido[3,2-b]indole-9-carbonitrile To 7-(3,5-dimethylisoxazol-4-yl)-2-methyl-5H-pyrido[3,2-b]indole-9-carbonitrile (7 mg, 0.023 mmol), was added anhydrous dimethylformamide (1 mL), cesium carbonate (22.6 mg, 0.069 mmol) and benzyl bromide (6 µl, 0.046 mmol). The vial was capped and stirred at room temperature for 1 h. The reaction mixture was treated with water and extracted with ethyl acetate (2×). The combined ethyl acetate layer was washed with brine, dried over sodium sulfate, and evaporated to give the crude N-benzylated product that was chromatographed over silica gel using 0 to 100% ethyl acetate in hexanes. The product containing fractions were combined and concentrated to give 5-benzyl-7-(3,5-dimethylisoxazol-4-yl)-2-methyl-5H-pyrido[3,2-b]indole-9-carbonitrile (4.1 mg, 45%): HPLC: RT=1.03 min (Waters Acquity UPLC BEH C18 1.7 um 2.0×50 mm, CH$_3$CN/H$_2$O/0.05% TFA, 1 min gradient, wavelength=254 nm); MS (ES): m/z=393.2 [M+1]$^+$; $^1$H NMR (400 MHz, Chloroform-d) δ 7.67 (d, J=8.4 Hz, 1H), 7.48 (d, J=1.3 Hz, 1H), 7.39-7.32 (m, 2H), 7.32-7.26 (m, 3H), 7.08 (dd, J=7.3, 2.4 Hz, 2H), 5.53 (s, 2H), 2.82 (s, 3H), 2.35 (s, 3H), 2.19 (s, 3H).

Step 6: 5-Benzyl-7-(dimethyl-1,2-oxazol-4-yl)-2-methyl-5H-pyrido[3,2-b]indole-9-carboxamide To 5-benzyl-7-(3,5-dimethylisoxazol-4-yl)-2-methyl-5H-pyrido[3,2-b]indole-9-carbonitrile (4.1 mg, 10.5 µmol) in DMSO (0.6 mL) was added potassium carbonate (4.3 mg, 0.031 mmol) and 35% hydrogen peroxide (0.027 mL, 0.313 mmol). After 2 h, additional potassium carbonate (4.3 mg, 0.031 mmol) and hydrogen peroxide (0.027 mL, 0.313 mmol) were added and the reaction warmed to 37° C. for 1 h. The reaction mixture was cooled to room temperature and treated with water followed by aqueous sodium bisulfite. The resulting white suspension was filtered to obtain a white residue and a cloudy filtrate. The filtrate was extracted with ethyl acetate and the organic layer was combined with the original residue and concentrated to give 4 mg of crude product. This product was dissolved in minimal ethyl acetate and purified by silica gel flash column chromatography using 0 to 100% ethyl acetate in hexanes. The product containing fraction was concentrated to give 5-benzyl-7-(3, 5-dimethylisoxazol-4-yl)-2-methyl-5H-pyrido[3,2-b]indole-9-carboxamide (2.4 mg, 53%) as a colorless solid: HPLC: RT=0.76 min (Waters Acquity UPLC BEH C18 1.7 um 2.0×50 mm, CH$_3$CN/H$_2$O/0.05% TFA, 1 min gradient, wavelength=254 nm); MS (ES): m/z=411.3 [M+1]$^+$; $^1$H NMR (400 MHz, Chloroform-d) δ 12.88 (br. s., 1H), 8.34 (d, J=1.5 Hz, 1H), 7.75 (d, J=8.4 Hz, 1H), 7.38 (d, J=1.5 Hz, 1H), 7.34 (d, J=8.4 Hz, 1H), 7.32-7.27 (m, 3H), 7.09 (dd, J=7.4, 2.1 Hz, 2H), 6.18 (br. s., 1H), 5.58 (s, 2H), 2.77 (s, 3H), 2.36 (s, 3H), 2.21 (s, 3H).

Example 2

4-{5-Benzyl-2-methyl-5H-pyrido[3,2-b]indol-7-yl}-3,5-dimethyl-1,2-oxazole

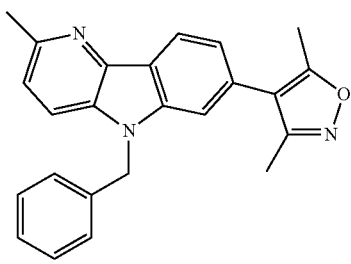 [SMILES: Cc1ccc2c(n1)c1ccc(-c3c(C)noc3C)cc1n2Cc1ccccc1]

Step 1: 2-Chloro-N-(3-(3,5-dimethylisoxazol-4-yl) phenyl)-6-methylpyridin-3-amine To a vial containing 3-(3,5-dimethylisoxazol-4-yl)aniline (96 mg, 0.510 mmol) was added 3-bromo-2-chloro-6-methylpyridine (211 mg, 1.02 mmol), cesium carbonate (332 mg, 1.02 mmol), chloro(2-dicyclohexylphosphino-2',4',6'-triisopropyl-1,1'-biphenyl)[2-(2'-amino-1,1'-biphenyl)]palladium (II) (CAS #1310584-14-5, 10.0 mg, 0.013 mmol), and toluene (2 mL). The resulting suspension was degassed by bubbling argon through the reaction mixture. The vial was capped with a pressure-safe septum cap and heated to 100° C. for 3 h. The reaction mixture was cooled to room temperature and filtered through a pad of silica gel. The filter pad was washed with ethyl acetate. The filtrate was concentrated and purified by silica gel chromatography with 0-100% ethyl acetate in hexanes. The product containing fractions were evaporated to give 2-chloro-N-(3-(3,5-dimethylisoxazol-4-yl)phenyl)-6-methylpyridin-3-amine (49 mg, 31%) as a pale brown solid: HPLC: RT=0.97 min (Waters Acquity UPLC BEH C18 1.7 um 2.0×50 mm, CH$_3$CN/H$_2$O/0.05% TFA, 1 min gradient, wavelength=254 nm); MS (ES): m/z=314.2/315.9 $^{35}$Cl/$^{37}$Cl [M+1]$^+$.

Step 2: 3,5-Dimethyl-4-(2-methyl-5H-pyrido[3,2-b]indol-7-yl)isoxazole

To a degassed solution of 2-chloro-N-(3-(3,5-dimethylisoxazol-4-yl)phenyl)-6-methylpyridin-3-amine (49 mg, 0.156 mmol) in dioxane (2 mL) was added palladium acetate (5.6 mg, 0.025 mmol), tri(tert-butylphosphonium)tetrafluoroborate (9.1 mg, 0.031 mmol) and solid potassium t-butoxide (88 mg, 0.781 mmol). The vial was capped with a pressure-safe teflon lined cap and heated to 100° C. for 14 h. The reaction mixture was cooled to room temperature and concentrated. To the residue was added ethyl acetate and filtered through a pad of silica. The filtrate was concentrated and the crude product was purified by silica gel chromatography using 0-100% ethyl acetate in hexanes. The product containing fractions were combined and evaporated to give 3,5-dimethyl-4-(2-methyl-5H-pyrido[3,2-b]indol-7-yl)isoxazole (29 mg, 67%): HPLC: RT=0.61 min (Waters Acquity UPLC BEH C18 1.7 um 2.0×50 mm, CH$_3$CN/H$_2$O/0.05% TFA, 1 min gradient, wavelength=254 nm); MS (ES): m/z=278.1 [M+1]$^+$.

Step 3: 4-{5-Benzyl-2-methyl-5H-pyrido[3,2-b]indol-7-yl}-3,5-dimethyl-1,2-oxazole To a 2 dram vial was added a solution of 3,5-dimethyl-4-(2-methyl-5H-pyrido[3,2-b]indol-7-yl)isoxazole (29 mg, 0.105 mmol) in DMF (1 mL), cesium carbonate (102 mg, 0.314 mmol) and benzyl bromide (0.025 mL, 0.209 mmol). The resulting suspension was stirred at room temperature for 1 h. To the reaction mixture was added water. The resulting suspension was extracted with ethyl acetate (×2). The combined ethyl acetate layer was concentrated. The residue was dissolved in DMF, filtered through a syringe filter and purified by reverse phase preparative HPLCMS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-100% B over 25 minutes, then a 5-minute hold at 100% B; Flow: 20 mL/min. Fractions containing the desired product were combined and dried via centrifugal evaporation to obtain 4-(5-benzyl-2-methyl-5H-pyrido[3,2-b]indol-7-yl)-3,5-dimethylisoxazole (22.6 mg, 59%): HPLC: RT=1.48 min (Waters Acquity UPLC BEH C18 1.7 um 2.0×50 mm, CH$_3$CN/H$_2$O/0.05% TFA, 1 min gradient, wavelength=254 nm); MS (ES): m/z=368.2 [M+1]$^+$; $^1$H NMR (500 MHz, DMSO-d$_6$) δ 8.26 (d, J=8.1 Hz, 1H), 8.03 (d, J=8.4 Hz, 1H), 7.66 (s, 1H), 7.34 (d, J=8.4 Hz, 1H), 7.30-7.14 (m, 6H), 5.70 (s, 2H), 2.65 (s, 3H), 2.40 (s, 3H), 2.23 (s, 3H).

Example 3

2-[7-(Dimethyl-1H-1,2,3-triazol-5-yl)-5-[(S)-(4-fluorophenyl)(oxan-4-yl)methyl]-5H-pyrido[3,2-b]indol-3-yl]propan-2-ol

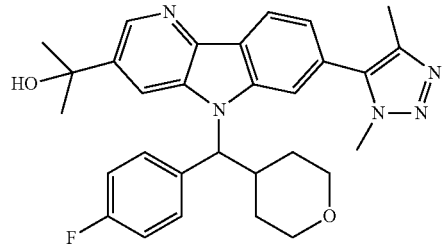 [SMILES: Cc1nnn(C)c1-c1ccc2c3ncc(C(C)(C)O)cc3n(C(c3ccc(F)cc3)C3CCOCC3)c2c1]

Step 1: Methyl 6-chloro-5-nitronicotinate

A 250 mL round-bottomed flask was charged with 6-hydroxy-5-nitronicotinic acid (2.72 g, 14.8 mmol) and thionyl chloride (6.6 mL, 90 mmol), purged with N$_2$, DMF (0.11 mL, 1.42 mmol) was added then heated to reflux with stirring overnight. The reaction was cooled to room temperature and concentrated in vacuo. The residue was dissolved in CH$_2$Cl$_2$ (70 mL), cooled to 0° C., then methanol (10 mL, 247 mmol) was added, allowed to gradually warm to room temperature as bath warmed, and stirred overnight. The reaction mixture was concentrated. The resulting solid was recrystallized from hot EtOH, cooled in ice, the solid collected by filtration, washed with cold EtOH, and air dried to afford the product (methyl 6-chloro-5-nitronicotinate (2.433 g, 76%)) as a tan solid: $^1$H NMR (400 MHz, CDCl$_3$) δ 9.18 (d, J=2.0 Hz, 1H), 8.77 (d, J=2.2 Hz, 1H), 4.03 (s, 3H).

Step 2: Methyl 6-(4-bromophenyl)-5-nitronicotinate and methyl 6-(4'-bromo-[1,1'-biphenyl]-4-yl)-5-nitronicotinate To a stirred solution of methyl 6-chloro-5-nitronicotinate (1.06 g, 4.89 mmol), (4-bromophenyl)boronic acid (1.12 g, 5.58 mmol), and PdCl$_2$(dppf) (0.19 g, 0.260 mmol) in THF (46 mL) was added tripotassium phosphate (3M in H$_2$O, 4.6 mL, 13.8 mmol). After purging with N$_2$ (vacuum/N$_2$×3), the reaction was heated at 75° C. with stirring. After 2.5 h, the reaction was cooled to room temperature and concentrated. The residue was partitioned between EtOAc and H$_2$O, the organic phase was separated, washed with sat. NaCl, dried over sodium sulfate, filtered, and concentrated. The residue was purified by flash chromatography (Teledyne ISCO CombiFlash Rf, gradient of 0% to 100% using solvent A/B=CH$_2$Cl$_2$/EtOAc over 12 column volumes, RediSep SiO$_2$ 80 g, loaded as DCM solution). A 62:26 mixture (by LCMS) of methyl 6-(4-bromophenyl)-5-nitronicotinate and methyl 6-(4'-bromo-[1,1'-biphenyl]-4-yl)-5-nitronicotinate (1.79 g) was obtained as a pale yellow solid, which was used as in the next step: Methyl 6-(4-bromophenyl)-5-nitronicotinate: HPLC: RT=1.31 min (Waters Acquity UPLC BEH C18 1.7 um 2.0×50 mm, CH$_3$CN/H$_2$O/0.1% TFA, 1 min gradient, wavelength=254 nm); MS (ES): m/z=337/339 $^{79}$Br/$^{81}$Br [M+1]$^+$; methyl 6-(4'-bromo-[1,1'-biphenyl]-4-yl)-5-nitronicotinate: HPLC: RT=1.53 min (Waters Acquity UPLC BEH C18 1.7 um 2.0×50 mm, CH$_3$CN/H$_2$O/0.1%

TFA, 1 min gradient, wavelength=254 nm); MS (ES): m/z=413/415 $^{79}$Br/$^{81}$Br [M+1]$^+$.

Step 3: Methyl 7-bromo-5H-pyrido[3,2-b]indole-3-carboxylate and methyl 7-(4-bromophenyl)-5H-pyrido[3,2-b]indole-3-carboxylate In a 100 mL RB flask was added a mixture of methyl 6-(4-bromophenyl)-5-nitronicotinate and methyl 6-(4'-bromo-[1,1'-biphenyl]-4-yl)-5-nitronicotinate (1.79 g) and 1,2-bis(diphenylphosphino)ethane (2.54 g, 6.38 mmol) in 1,2-dichlorobenzene (22 mL). The flask was placed in a pre-heated heating block at 170° C. After 1 h, the mixture was cooled to room temperature, then concentrated in vacuo under high vacuum. The residue was dissolved in THF and a small amount of MeOH, SiO$_2$ (20 g) was added, concentrated in vacuo then dried under vacuum overnight. The material was then purified by flash chromatography (Teledyne ISCO CombiFlash Rf, gradient of 0% to 60% using solvent A/B=CH$_2$Cl$_2$/EtOAc over 12 column volumes, RediSep SiO$_2$ 120 g). A 3:1 mixture of methyl 7-bromo-5H-pyrido[3,2-b]indole-3-carboxylate and methyl 7-(4-bromophenyl)-5H-pyrido[3,2-b]indole-3-carboxylate (0.95 g) was obtained as a yellow solid: HPLC for methyl 7-bromo-5H-pyrido[3,2-b]indole-3-carboxylate: RT=0.82 min (Waters Acquity UPLC BEH C18 1.7 um 2.0×50 mm, CH$_3$CN/H$_2$O/0.05% TFA, 1 min gradient, wavelength=254 nm); MS (ES): m/z=305/307 $^{79}$Br/$^{81}$Br [M+1]$^+$.

Step 4: Methyl 7-(1,4-dimethyl-1H-1,2,3-triazol-5-yl)-5H-pyrido[3,2-b]indole-3-carboxylate In a 250 mL RB flask was added a mixture of methyl 7-bromo-5H-pyrido[3,2-b]indole-3-carboxylate and methyl 7-(4-bromophenyl)-5H-pyrido[3,2-b]indole-3-carboxylate (1.05 g, 3.44 mmol), 1,4-dimethyl-5-(tributylstannyl)-1H-1,2,3-triazole (1.50 g, 3.88 mmol), and TEA (0.96 mL, 6.89 mmol) in DMF (49 mL), and the clear, orange solution was purged by bubbling a nitrogen stream through the solution for 5 min. While purging, copper(i) iodide (107.6 mg, 0.565 mmol) and Pd(Ph$_3$P)$_4$ (262.5 mg, 0.227 mmol) were added, then the flask was fitted with a septum, and heated in a heating block at 95° C. After 3.5 h, the reaction cooled to room temperature, concentrated in vacuo, then dried under vacuum overnight. The residue was purified by flash chromatography (Teledyne ISCO CombiFlash Rf, gradient of 0% to 75% using solvent A/B=CH$_2$Cl$_2$/acetone over 15 column volumes, RediSep SiO$_2$ 120 g, loaded as DCM solution). Fractions containing pure product were combined and set aside, fractions containing impure product were combined, SiO$_2$ (10 g) was added, and concentrated. The material was then repurified by flash chromatography (Teledyne ISCO CombiFlash Rf, gradient of 0% to 70% using solvent A/B=CH$_2$Cl$_2$/acetone over 15 column volumes, RediSep SiO$_2$ 220 g). Once again, pure product was combined with product above and set aside. Impure product fractions were combined, 2 g SiO$_2$ was added, concentrated, dried under vacuum overnight. Repurified by flash chromatography (Teledyne ISCO CombiFlash Rf, gradient of 0% to 70% using solvent A/B=CH$_2$Cl$_2$/acetone over 20 column volumes, RediSep SiO$_2$ 40 g). Fractions containing pure product were combined with above product fractions and concentrated. The product, methyl 7-(1,4-dimethyl-1H-1,2,3-triazol-5-yl)-5H-pyrido[3,2-b]indole-3-carboxylate (431.1 mg, 39%) was obtained as a yellow solid: HPLC: RT=0.916 min (Waters Acquity UPLC BEH C18 1.7 um 2.0×50 mm, CH$_3$CN/H$_2$O/0.1% TFA, 1.5 min gradient, wavelength=254 nm); MS (ES): m/z=322 [M+1]$^+$.

Step 5: (S)-Methyl 7-(1,4-dimethyl-1H-1,2,3-triazol-5-yl)-5-((4-fluorophenyl)(tetrahydro-2H-pyran-4-yl)methyl)-5H-pyrido[3,2-b]indole-3-carboxylate To a cool (0° C.), stirred solution of methyl 7-(1,4-dimethyl-1H-1,2,3-triazol-5-yl)-5H-pyrido[3,2-b]indole-3-carboxylate (36.5 mg, 0.114 mmol), (R)-(4-fluorophenyl)(tetrahydro-2H-pyran-4-yl)methanol (49.9 mg, 0.237 mmol), and triphenylphosphine (63.2 mg, 0.241 mmol) in toluene (2.4 mL) under N$_2$ was added dropwise over 5 min via syringe DIAD (0.05 mL, 0.257 mmol), the solution stirred for 5 min, then removed from ice bath, and stirred at room temperature. After 3 h, the mixture was concentrated in vacuo, dried under vacuum. The residue was purified by flash chromatography (Teledyne ISCO CombiFlash Rf, gradient of 0% to 100% using solvent A/B=CH$_2$Cl$_2$/EtOAc over 15 column volumes followed by 0-30% MeOH/DCM over 15 CV, RediSep SiO$_2$ 12 g, loaded as DCM solution). The product (S)-methyl 7-(1,4-dimethyl-1H-1,2,3-triazol-5-yl)-5-((4-fluorophenyl)(tetrahydro-2H-pyran-4-yl)methyl)-5H-pyrido[3,2-b]indole-3-carboxylate (24.6 mg, 42%) was obtained as a pale yellow solid: HPLC: RT=1.179 min (Waters Acquity UPLC BEH C18 1.7 um 2.0×50 mm, CH$_3$CN/H$_2$O/0.1% TFA, 1.5 min gradient, wavelength=254 nm); MS (ES): m/z=514 [M+1]$^+$.

Step 6: 2-[7-(Dimethyl-1H-1,2,3-triazol-5-yl)-5-[(S)-(4-fluorophenyl)(oxan-4-yl)methyl]-5H-pyrido[3,2-b]indol-3-yl]propan-2-ol To a cold (−15° C.), stirred solution of (S)-methyl 7-(1,4-dimethyl-1H-1,2,3-triazol-5-yl)-5-((4-fluorophenyl)(tetrahydro-2H-pyran-4-yl)methyl)-5H-pyrido[3,2-b]indole-3-carboxylate (24.6 mg, 0.048 mmol) in THF (1.0 mL) under N$_2$ was added methylmagnesium bromide (3M in Et$_2$O, 0.26 mL, 0.780 mmol). After 20 min, the mixture had warmed to ∼−6° C., placed in an ice-water bath for 30 min. The reaction was quenched with sat. NH$_4$Cl (5 mL), diluted with EtOAc, the organic phase was separated, washed with sat. NaCl then dried over sodium sulfate, filtered, and concentrated. The residue was purified by flash chromatography (Teledyne ISCO CombiFlash Rf, gradient of 0% to 30% using solvent A/B=CH$_2$Cl$_2$/MeOH over 30 column volumes, RediSep SiO$_2$ 4 g, loaded as DCM solution), then further purified by SFC (Berger SFC MGII; Chiralcel OD-H, 25 cm×3 cm ID, 5 μm, 85.0 mL/min at 100 bar, Mobile Phase: 77/23 CO$_2$/MeOH; Detector Wavelength: 220 nm). The product (S)-2-(7-(1,4-dimethyl-1H-1,2,3-triazol-5-yl)-5-((4-fluorophenyl)(tetrahydro-2H-pyran-4-yl)methyl)-5H-pyrido[3,2-b]indol-3-yl)propan-2-ol (8.7 mg, 34%) was obtained as a colourless solid: HPLC: RT=0.971 min (Waters Acquity UPLC BEH C18 1.7 um 2.0×50 mm, CH$_3$CN/H$_2$O/0.1% TFA, 1.5 min gradient, wavelength=254 nm); MS (ES): m/z=514 [M+1]$^+$; $^1$H NMR (400 MHz, DMSO-d$_6$) δ 8.68 (s, 1H), 8.37 (br. s., 1H), 8.29 (d, J=7.9 Hz, 1H), 8.04 (br. s., 1H), 7.69 (dd, J=8.6, 5.5 Hz, 2H), 7.33 (d, J=7.9 Hz, 1H), 7.16 (t, J=8.8 Hz, 2H), 5.85 (d, J=11.2 Hz, 1H), 5.34 (s, 1H), 4.00 (s, 3H), 3.89 (d, J=9.2 Hz, 1H), 3.73 (d, J=9.2 Hz, 1H), 3.48 (t, J=10.9 Hz, 1H), 3.36 (d, J=9.0 Hz, 1H), 3.17-3.29 (m, 1H), 2.29 (s, 3H), 1.64-1.76 (m, 1H), 1.61 (s, 6H), 1.50-1.58 (m, 1H), 1.21-1.39 (m, 2H), 0.97 (d, J=12.5 Hz, 1H).

Examples 4-9

The compounds in Table 1 were prepared according to the procedures described for Example 1:

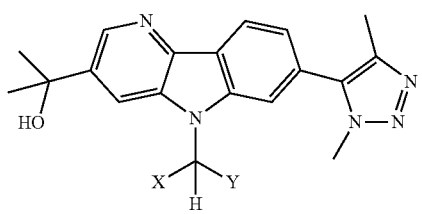

TABLE 1

| Example | X | Y | HPLC RT (min) | LCMS (M + H) | HPLC Method |
|---|---|---|---|---|---|
| 4 | F₃C~~~ | ~~~CF₃ | 1.711 | 528 | A |
| 5 | ~~~ (propyl) | ~~~ (propyl) | 1.728 | 420 | A |
| 6 Enantioner A | F₃C~~~ | 2-pyridyl | 1.44 | 509 | A |
| 7 Enantiomer B | F₃C~~~ | 2-pyridyl | 1.45 | 509 | A |
| 8 | tetrahydropyran-4-yl | phenyl | 1.22 | 496 | A |
| 9 | tetrahydropyran-4-yl | 2-fluorophenyl | 1.44 | 514 | A |

HPLC methods for Table 1: A: Waters Acquity UPLC BEH C18 1.7 um 2.1×50 mm, CH₃CN/H₂O/10 mM NH₄OAc, 1.5 min gradient, wavelength=220 nm.

Example 10

2-[7-(Dimethyl-1H-1,2,3-triazol-5-yl)-9-fluoro-5-(1,1,1,7,7,7-hexafluoroheptan-4-yl)-5H-pyrido[3,2-b]indol-3-yl]propan-2-ol

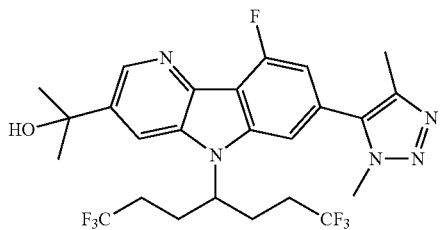 [SMILES: Cc1nnn(C)c1-c1cc(F)c2c3ncc(C(C)(C)O)cc3n(C(CCC(F)(F)F)CCC(F)(F)F)c2c1]

Step 1: Methyl 6-(4-bromo-2-fluorophenyl)-5-nitronicotinate and methyl 6-(4'-bromo-2',3-difluoro-[1,1'-biphenyl]-4-yl)-5-nitronicotinate To a stirred solution of methyl 6-chloro-5-nitronicotinate (297.7 mg, 1.38 mmol), (4-bromo-2-fluorophenyl)boronic acid (326.5 mg, 1.49 mmol), and PdCl₂(dppf) (48.7 mg, 0.067 mmol) in THF (14 mL) was added tripotassium phosphate (3M in H₂O, 1.4 mL, 4.20 mmol). The reaction was purged with N₂ (vacuum/N₂×3) and heated at 75° C. with stirring for 2 h. The reaction was cooled to room temperature and concentrated. The residue was partitioned between EtOAc and H₂O, the organic phase was separated, washed with sat. NaCl, dried over sodium sulfate, filtered, and concentrated. The residue was purified by flash chromatography (Teledyne ISCO CombiFlash Rf, gradient of 0% to 50% using solvent A/B=hexanes/EtOAc over 12 column volumes, RediSep SiO₂ 40 g, loaded as DCM solution). A 3.7:1 mixture (by LCMS) of methyl 6-(4-bromo-2-fluorophenyl)-5-nitronicotinate and methyl 6-(4'-bromo-2',3-difluoro-[1,1'-biphenyl]-4-yl)-5-nitronicotinate (456.6 mg) was obtained: HPLC for methyl 6-(4-bromo-2-fluorophenyl)-5-nitronicotinate: RT=1.352 min (Waters Acquity UPLC BEH C18 1.7 um 2.0×50 mm, CH₃CN/H₂O/ 0.1% TFA, 1.5 min gradient, wavelength=254 nm); MS (ES): m/z=355/357 $^{79}$Br/$^{81}$Br [M+1]⁺.

Step 2: Methyl 7-bromo-9-fluoro-5H-pyrido[3,2-b]indole-3-carboxylate

In a 50 mL RB flask was added a mixture of methyl 6-(4-bromo-2-fluorophenyl)-5-nitronicotinate (456.6 mg, 1.29 mmol) and 1,2-bis(diphenylphosphino)ethane (615.3 mg, 1.54 mmol) in 1,2-dichlorobenzene (5.2 mL) and the flask placed in a pre-heated heating block at 170° C. for 30 min, then cooled to room temperature and concentrated in vacuo. The residue was dissolved in MeOH, $SiO_2$ (5 g) was added, concentrated in vacuo then dried under vacuum overnight. The material was then purified by flash chromatography (Teledyne ISCO CombiFlash Rf, gradient of 0% to 100% using solvent A/B=$CH_2Cl_2$/acetone over 15 column volumes, RediSep $SiO_2$ 40 g). The product methyl 7-bromo-9-fluoro-5H-pyrido[3,2-b]indole-3-carboxylate (220.8 mg, 53%) was obtained as a black solid: HPLC: RT=1.117 min (Waters Acquity UPLC BEH C18 1.7 um 2.0×50 mm, $CH_3CN/H_2O$/0.1% TFA, 1.5 min gradient, wavelength=254 nm); MS (ES): m/z=323/325 $^{79}Br/^{81}Br$ [M+1]$^+$.

Step 3: Methyl 7-(1,4-dimethyl-1H-1,2,3-triazol-5-yl)-9-fluoro-5H-pyrido[3,2-b]indole-3-carboxylate In a 50 mL RB flask was added a mixture of methyl 7-bromo-9-fluoro-5H-pyrido[3,2-b]indole-3-carboxylate (220.8 mg, 0.683 mmol), 1,4-dimethyl-5-(tributylstannyl)-1H-1,2,3-triazole (342.8 mg, 0.888 mmol), and TEA (0.19 mL, 1.36 mmol) in DMF (14 mL) and the mixture was purged by bubbling nitrogen through the solution. While purging, copper(I) iodide (30.3 mg, 0.159 mmol) and $Pd(Ph_3P)_4$ (49.8 mg, 0.043 mmol) were added, the flask fitted with a septum then heated in a heating block at 95° C. with stirring overnight. The mixture was cooled to room temperature, $N_2$ was bubbled through the reaction solution, then CuI (84.6 mg) and $Pd(Ph_3P)_4$ (98.5 mg) followed by a solution of stannane (436.0 mg) in DMF (2 mL) were added, the septum refitted then reheated overnight. The reaction was cooled to room temperature, $SiO_2$ (5 g) was added, concentrated in vacuo then dried under vacuum overnight. The material was purified by flash chromatography (Teledyne ISCO CombiFlash Rf, gradient of 0% to 100% using solvent A/B=$CH_2Cl_2$/acetone over 20 column volumes, RediSep $SiO_2$ 40 g). The product, methyl 7-(1,4-dimethyl-1H-1,2,3-triazol-5-yl)-9-fluoro-5H-pyrido[3,2-b]indole-3-carboxylate (85.6 mg, 37%) was obtained as a pale yellow solid: HPLC:
RT=0.956 min (Waters Acquity UPLC BEH C18 1.7 um 2.0×50 mm, $CH_3CN/H_2O$/0.1% TFA, 1.5 min gradient, wavelength=254 nm); MS (ES): m/z=340 [M+1]$^+$.

Step 4: Methyl 7-(1,4-dimethyl-1H-1,2,3-triazol-5-yl)-9-fluoro-5-(1,1,1,7,7,7-hexafluoroheptan-4-yl)-5H-pyrido[3,2-b]indole-3-carboxylate To a 40 mL I-Chem vial equipped with a stir bar under ambient atmosphere, was added methyl 7-(1,4-dimethyl-1H-1,2,3-triazol-5-yl)-9-fluoro-5H-pyrido[3,2-b]indole-3-carboxylate (42.4 mg, 0.125 mmol), 1,1,1,7,7,7-hexafluoroheptan-4-yl 4-methylbenzenesulfonate (70.1 mg, 0.185 mmol), and $Cs_2CO_3$ (126.0 mg, 0.387 mmol). The vial was sealed with a PTFE-lined septum screw-cap, DMF (2.4 mL) was added, then purged with $N_2$ (vacuum/$N_2$×3). The reaction was then heated to 80° C. with stirring overnight. The reaction was cooled to room temperature, additional tosylate and $Cs_2CO_3$ were added, and the reaction heated for 5 h. The reaction was cooled to room temperature, diluted with EtOAc, washed with 10% LiCl (×3), sat. NaCl then dried ($Na_2SO_4$), filtered, and concentrated. The residue was purified by flash chromatography (Teledyne ISCO CombiFlash Rf, gradient of 0% to 7% using solvent A/B=$CH_2Cl_2$/MeOH over 30 column volumes, RediSep $SiO_2$ 24 g, loaded as DCM solution). The product, methyl 7-(1,4-dimethyl-1H-1,2,3-triazol-5-yl)-9-fluoro-5-(1,1,1,7,7,7-hexafluoroheptan-4-yl)-5H-pyrido[3,2-b]indole-3-carboxylate (38.5 mg, 57%) was obtained as a pale yellow solid: HPLC: RT=1.278 min (Waters Acquity UPLC BEH C18 1.7 um 2.0×50 mm, $CH_3CN/H_2O$/0.1% TFA, 1.5 min gradient, wavelength=254 nm); MS (ES): m/z=546 [M+1]$^+$.

Step 5: 2-[7-(Dimethyl-1H-1,2,3-triazol-5-yl)-9-fluoro-5-(1,1,1,7,7,7-hexafluoroheptan-4-yl)-5H-pyrido[3,2-b]indol-3-yl]propan-2-ol To a cold (−78° C.), stirred solution of methyl 7-(1,4-dimethyl-1H-1,2,3-triazol-5-yl)-9-fluoro-5-(1,1,1,7,7,7-hexafluoroheptan-4-yl)-5H-pyrido[3,2-b]indole-3-carboxylate (38.5 mg, 0.071 mmol) in THF (1.4 mL) under $N_2$ was added methylmagnesium bromide (3M in $Et_2O$, 376 μl, 1.13 mmol), stirred for 15 min, placed in an ice-water bath, stirred for 30 min. The reaction was quenched with sat. $NH_4Cl$ (5 mL), diluted with EtOAc, the organic phase was separated, concentrated, the residue dissolved in DMF (2 mL), and filtered thru a 41.1 membrane filter. The material was purified via preparative LC/MS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-100% B over 20 minutes, then a 0-minute hold at 100% B; Flow: 20 mL/min. Fractions containing the desired product were combined and dried via centrifugal evaporation. Obtained the product (19.1 mg, 50%): HPLC: RT=1.764 min (Waters Acquity UPLC BEH C18, 2.1×50 mm, 1.7-nm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm; MS (ES): m/z=546 [M+1]$^+$; $^1H$ NMR (500 MHz, DMSO-$d_6$) δ 8.75 (br s, 1H), 8.21 (br d, J=7.07 Hz, 1H), 7.82-8.00 (m, 1H), 7.76 (s, 1H), 7.26 (br dd, J=6.06, 10.43 Hz, 1H), 5.07 (br s, 1H), 4.03 (br d, J=15.48 Hz, 3H), 2.52-2.66 (m, 2H), 2.17-2.41 (m, 7H), 1.73 (br d, J=12.12 Hz, 2H), 1.59 (br d, J=5.39 Hz, 6H).

Example 11

2-[7-(Dimethyl-1H-1,2,3-triazol-5-yl)-9-fluoro-5-[(S)-oxan-4-yl(phenyl)methyl]-5H-pyrido[3,2-b]indol-3-yl]propan-2-ol

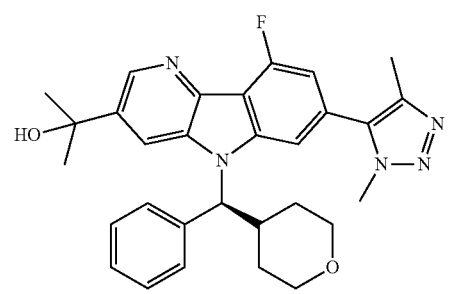 [SMILES: Cc1nnn(C)c1-c1cc(F)c2c3ncc(C(C)(C)O)cc3n([C@H](c3ccccc3)C3CCOCC3)c2c1]

Step 1: (S)-Methyl 7-(1,4-dimethyl-1H-1,2,3-tri-azol-5-yl)-9-fluoro-5-(phenyl(tetrahydro-2H-pyran-4-yl)methyl)-5H-pyrido[3,2-b]indole-3-carboxylate To a cool (0° C.), stirred suspension of methyl 7-(1,4-dimethyl-1H-1,2,3-triazol-5-yl)-9-fluoro-5H-pyrido[3,2-b]indole-3-carboxylate (38.6 mg, 0.114 mmol), (R)-phenyl (tetrahydro-2H-pyran-4-yl)methanol (45.4 mg, 0.236 mmol), and triphenylphosphine (62.0 mg, 0.236 mmol) in THF (2.4 mL) under $N_2$ was added dropwise over 1 min via syringe DIAD (0.05 mL, 0.257 mmol). The suspension dissolved quickly, and the dark solution was allowed to warm to room temperature and stirred overnight. The reaction was concentrated, dried under vacuum overnight. The residue was purified by flash chromatography (Teledyne ISCO CombiFlash Rf, gradient of 0% to 20% using solvent A/B=$CH_2Cl_2$/MeOH over 30 column volumes, RediSep $SiO_2$ 12 g, loaded as DCM solution). Fractions containing product were collected and concentrated, then repurified: Teledyne ISCO CombiFlash Rf, gradient of 0% to 5% using solvent A/B=$CH_2Cl_2$/MeOH over 30 column volumes, RediSep $SiO_2$ 24 g, loaded as DCM solution. The product, (S)-methyl 7-(1,4-dimethyl-1H-1,2,3-triazol-5-yl)-9-fluoro-5-(phenyl(tetrahydro-2H-pyran-4-yl)methyl)-5H-pyrido[3,2-b]indole-3-carboxylate (33.1 mg, 57%) was obtained as a pale yellow film: HPLC: RT=1.179 min (Waters Acquity UPLC BEH C18 1.7 um 2.0×50 mm, $CH_3CN/H_2O$/0.1% TFA, 1.5 min gradient, wavelength=254 nm); MS (ES): m/z=514 $[M+1]^+$.

Step 2: 2-[7-(Dimethyl-1H-1,2,3-triazol-5-yl)-9-fluoro-5-[(S)-oxan-4-yl(phenyl)methyl]-5H-pyrido[3,2-b]indol-3-yl]propan-2-ol To a cold (−78° C.), stirred solution of (S)-methyl 7-(1,4-dimethyl-1H-1,2,3-triazol-5-yl)-9-fluoro-5-(phenyl(tetrahydro-2H-pyran-4-yl)methyl)-5H-pyrido[3,2-b]indole-3-carboxylate (33.1 mg, 0.064 mmol) in THF (1.3 mL) under $N_2$ was added methylmagnesium bromide (3M in $Et_2O$, 344 μl, 1.03 mmol), stirred for 15 min, placed in an ice-water bath and stirred an additional 35 min. The reaction was quenched with sat. $NH_4Cl$ (5 mL), diluted with EtOAc, the organic phase was separated, concentrated, the residue dissolved in DMF (2 mL), filtered thru a 4μ membrane filter. The crude material was purified via preparative LC/MS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-100% B over 20 minutes, then a 0-minute hold at 100% B; Flow: 20 mL/min. Fractions containing the desired product were combined and dried via centrifugal evaporation. Obtained the product (8.8 mg, 26%): HPLC: RT=1.563 min (Waters Acquity UPLC BEH C18, 2.1×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm; MS (ES): m/z=514 $[M+1]^+$; $^1H$ NMR (500 MHz, DMSO-$d_6$) δ 8.71 (br s, 1H), 7.63 (br d, J=7.41 Hz, 2H), 7.29-7.39 (m, 2H), 7.16-7.28 (m, 2H), 5.87 (br d, J=11.11 Hz, 1H), 4.00 (br s, 2H), 3.88 (br d, J=11.44 Hz, 1H), 3.72 (br d, J=9.42 Hz, 1H), 3.24 (br t, J=11.44 Hz, 1H), 2.28 (br s, 3H), 1.59 (br s, 7H).

Example 12

2-[9-Chloro-7-(dimethyl-1H-1,2,3-triazol-5-yl)-5-(1,1,1,7,7,7-hexafluoroheptan-4-yl)-5H-pyrido[3,2-b]indol-3-yl]propan-2-ol

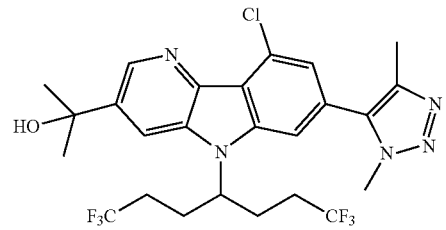 [SMILES: Cc1nnn(C)c1-c1cc(Cl)c2c3ncc(C(C)(C)O)cc3n(C(CCC(F)(F)F)CCC(F)(F)F)c2c1]

Step 1: Methyl 6-(4-bromo-2-chlorophenyl)-5-nitronicotinate and methyl 6-(4'-bromo-2',3-dichloro-[1,1'-biphenyl]-4-yl)-5-nitronicotinate To a stirred solution of methyl 6-chloro-5-nitronicotinate (417.4 mg, 1.93 mmol), (4-bromo-2-chlorophenyl)boronic acid (496.3 mg, 2.11 mmol), and $PdCl_2$(dppf) (76.5 mg, 0.105 mmol) in THF (18 mL) was added tripotassium phosphate (3M in $H_2O$, 1.8 mL, 5.40 mmol), purged with $N_2$ (vacuum/$N_2$×3), and the reaction was heated at 75° C. with stirring for 80 min. The reaction was cooled to room temperature, concentrated. The residue was partitioned between EtOAc and $H_2O$, the organic phase was separated, washed with sat. NaCl, dried over sodium sulfate, filtered, and concentrated. The residue was purified by flash chromatography (Teledyne ISCO CombiFlash Rf, gradient of 0% to 60% using solvent A/B=$CH_2Cl_2$/EtOAc over 12 column volumes, RediSep $SiO_2$ 40 g, loaded as DCM solution). Obtained a 2:1 mixture (by LCMS) of methyl 6-(4-bromo-2-chlorophenyl)-5-nitronicotinate and methyl 6-(4'-bromo-2',3-dichloro-[1,1'-biphenyl]-4-yl)-5-nitronicotinate (656.2 mg): HPLC (for methyl 6-(4-bromo-2-chlorophenyl)-5-nitronicotinate): RT=1.391 min (Waters Acquity UPLC BEH C18 1.7 um 2.0×50 mm, $CH_3CN/H_2O$/0.1% TFA, 1.5 min gradient, wavelength=254 nm); MS (ES): m/z=371 $[M+1]^+$.

Step 2: Methyl 7-bromo-9-chloro-5H-pyrido[3,2-b]indole-3-carboxylate

In a 50 mL RB flask was added a mixture of methyl 6-(4-bromo-2-chlorophenyl)-5-nitronicotinate (656.2 mg, 1.77 mmol) and 1,2-bis(diphenylphosphino)ethane (847.3 mg, 2.13 mmol) in 1,2-dichlorobenzene (7.2 mL) and the flask placed in a pre-heated heating block at 170° C. for 30 min, cooled to room temperature, concentrated in vacuo under high vacuum. The residue was dissolved in MeOH, $SiO_2$ (5 g) was added, concentrated then dried under vacuum overnight. The material was then purified by flash chromatography (Teledyne ISCO CombiFlash Rf, gradient of 0% to 100% using solvent A/B=$CH_2Cl_2$/acetone over 15 column volumes, RediSep $SiO_2$ 40 g). The product, methyl 7-bromo-9-chloro-5H-pyrido[3,2-b]indole-3-carboxylate (331.8 mg, 55%) was obtained as a black solid: HPLC: RT=1.201 min (Waters Acquity UPLC BEH C18 1.7 um 2.0×50 mm, $CH_3CN/H_2O$/0.1% TFA, 1.5 min gradient, wavelength=254 nm); MS (ES): m/z=339 $[M+1]^+$.

Step 3: Methyl 9-chloro-7-(1,4-dimethyl-1H-1,2,3-triazol-5-yl)-5H-pyrido[3,2-b]indole-3-carboxylate In a 50 mL RB flask was added a mixture of methyl 7-bromo-9-chloro-5H-pyrido[3,2-b]indole-3-carboxylate (331.8 mg, 0.977 mmol), 1,4-dimethyl-5-(tributylstannyl)-1H-1,2,3-triazole (565.9 mg, 1.47 mmol), and TEA (0.28 mL, 2.01 mmol) in DMF (20 mL) and the mixture was purged by bubbling nitrogen through the solution. While purging, copper(I) iodide (71.6 mg, 0.376 mmol) and Pd(Ph$_3$P)$_4$ (115.2 mg, 0.100 mmol) were added, the flask fitted with a septum then heated in a heating block at 95° C. overnight. The reaction was cooled to room temperature, SiO$_2$ (6 g) was added, concentrated then dried under vacuum. The material was then purified by flash chromatography (Teledyne ISCO CombiFlash Rf, gradient of 0% to 100% using solvent A/B=CH$_2$Cl$_2$/acetone over 20 column volumes, RediSep SiO$_2$ 40 g). The product, methyl 9-chloro-7-(1,4-dimethyl-1H-1,2,3-triazol-5-yl)-5H-pyrido[3,2-b]indole-3-carboxylate (109.8 mg, 32%) was obtained as a pale yellow solid: HPLC: RT=0.997 min (Waters Acquity UPLC BEH C18 1.7 um 2.0×50 mm, CH$_3$CN/H$_2$O/0.1% TFA, 1.5 min gradient, wavelength=254 nm); MS (ES): m/z=357/359 $^{35}$Cl/$^{37}$Cl [M+1]$^+$.

Step 4: Methyl 9-chloro-7-(1,4-dimethyl-1H-1,2,3-triazol-5-yl)-5-(1,1,1,7,7,7-hexafluoroheptan-4-yl)-5H-pyrido[3,2-b]indole-3-carboxylate To a 40 mL I-Chem vial equipped with a stir bar under ambient atmosphere was added methyl 9-chloro-7-(1,4-dimethyl-1H-1,2,3-triazol-5-yl)-5H-pyrido[3,2-b]indole-3-carboxylate (38.8 mg, 0.109 mmol), 1,1,1,7,7,7-hexafluoroheptan-4-yl 4-methylbenzenesulfonate (54.1 mg, 0.143 mmol), and Cs$_2$CO$_3$ (108.6 mg, 0.333 mmol). The vial was sealed with a PTFE-lined septum screw-cap, DMF (2.4 mL) was added, then purged with N$_2$ (vacuum/N$_2$×3). The reaction was then heated to 80° C. with stirring overnight. The reaction was cooled to room temperature, additional tosylate and Cs$_2$CO$_3$ were added, and the reaction heated for 5 h. The reaction was cooled to room temperature, diluted with EtOAc, washed with 10% LiCl (×3), then sat. NaCl, dried (Na$_2$SO$_4$), filtered, and concentrated. The residue was purified by flash chromatography (Teledyne ISCO CombiFlash Rf, gradient of 0% to 7% using solvent A/B=CH$_2$Cl$_2$/MeOH over 30 column volumes, RediSep SiO$_2$ 24 g, loaded as DCM solution). The product, methyl 9-chloro-7-(1,4-dimethyl-1H-1,2,3-triazol-5-yl)-5-(1,1,1,7,7,7-hexafluoroheptan-4-yl)-5H-pyrido[3,2-b]indole-3-carboxylate (41.7 mg, 68%) was obtained as a pale yellow solid: HPLC: RT=1.234 min (Waters Acquity UPLC BEH C18 1.7 um 2.0×50 mm, CH$_3$CN/H$_2$O/0.1% TFA, 1.5 min gradient, wavelength=254 nm); MS (ES): m/z=562 [M+1]$^+$.

Step 5: 2-[9-Chloro-7-(dimethyl-1H-1,2,3-triazol-5-yl)-5-(1,1,1,7,7,7-hexafluoroheptan-4-yl)-5H-pyrido[3,2-b]indol-3-yl]propan-2-ol To a cold (−78° C.), stirred solution of methyl 9-chloro-7-(1,4-dimethyl-1H-1,2,3-triazol-5-yl)-5-(1,1,1,7,7,7-hexafluoroheptan-4-yl)-5H-pyrido[3,2-b]indole-3-carboxylate (41.7 mg, 0.074 mmol) in THF (1.5 mL) under N$_2$ was added methylmagnesium bromide (3M in Et$_2$O, 396 µl, 1.19 mmol), stirred for 15 min, placed in an ice-water bath and stirred an additional 55 min. The reaction was quenched with sat. NH$_4$Cl (5 mL), diluted with EtOAc, the organic phase was separated, concentrated, the residue dissolved in DMF (2 mL) and filtered thru a 41.1 m membrane filter. The crude material was purified via preparative LC/MS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 15-100% B over 20 minutes, then a 0-minute hold at 100% B; Flow: 20 mL/min. Fractions containing the desired product were combined and dried via centrifugal evaporation. Obtained the product (15.7 mg, 38%): HPLC: RT=1.855 min (Waters Acquity UPLC BEH C18, 2.1×50 mm, 1.7-µm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm; MS (ES): m/z=562 [M+1]$^+$; $^1$H NMR (500 MHz, DMSO-d$_6$) δ 8.79 (br d, J=3.70 Hz, 1H), 8.22 (br d, J=7.07 Hz, 1H), 7.90 (s, 1H), 7.45 (br d, J=4.04 Hz, 1H), 5.08 (br s, 1H), 4.02 (br d, J=15.82 Hz, 3H), 2.58 (br d, J=5.39 Hz, 1H), 2.18-2.41 (m, 7H), 1.62-1.80 (m, 2H), 1.59 (br d, J=6.06 Hz, 6H).

Example 13

2-[9-Chloro-7-(dimethyl-1H-1,2,3-triazol-5-yl)-5-[(S)-oxan-4-yl(phenyl)methyl]-5H-pyrido[3,2-b]indol-3-yl]propan-2-ol

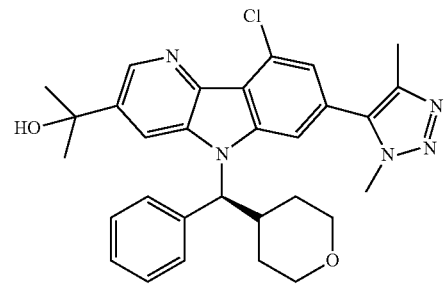 [SMILES: Cc1nnn(C)c1-c1cc(Cl)c2c3ncc(C(C)(C)O)cc3n([C@H](c3ccccc3)C3CCOCC3)c2c1]

Step 1: (S)-Methyl 9-chloro-7-(1,4-dimethyl-1H-1,2,3-triazol-5-yl)-5-(phenyl(tetrahydro-2H-pyran-4-yl)methyl)-5H-pyrido[3,2-b]indole-3-carboxylate To a cool (0° C.), stirred suspension of methyl 9-chloro-7-(1,4-dimethyl-1H-1,2,3-triazol-5-yl)-5H-pyrido[3,2-b]indole-3-carboxylate (40.3 mg, 0.113 mmol), (R)-phenyl(tetrahydro-2H-pyran-4-yl)methanol (43.6 mg, 0.227 mmol), and triphenylphosphine (65.2 mg, 0.249 mmol) in THF (2.4 mL) under N$_2$ was added dropwise over 1 min via syringe DIAD (0.05 mL, 0.257 mmol). The suspension dissolved quickly, and the dark solution was allowed to warm to room temperature and stirred overnight. The reaction was concentrated, dried under vacuum overnight. The residue was purified by flash chromatography (Teledyne ISCO CombiFlash Rf, gradient of 0% to 10% using solvent A/B=CH$_2$Cl$_2$/MeOH over 30 column volumes, RediSep SiO$_2$ 12 g, loaded as DCM solution). Fractions containing product were combined and concentrated. The residue was repurified by flash chromatography (Teledyne ISCO CombiFlash Rf, gradient of 0% to 7% using solvent A/B=CH$_2$Cl$_2$/MeOH over 30 column volumes, RediSep SiO$_2$ 24 g, loaded as DCM solution). The product, (S)-methyl 9-chloro-7-(1,4-dimethyl-1H-1,2,3-triazol-5-yl)-5-(phenyl(tetrahydro-2H-pyran-4-yl)methyl)-5H-pyrido[3,2-b]indole-3-carboxylate (93.3 mg, >100%) was obtained as a yellow oil, the impure material was used as is without further purification in the next step: HPLC: RT=1.240 min (Waters Acquity UPLC BEH C18 1.7 um 2.0×50 mm, $CH_3CN/H_2O/0.1\%$ TFA, 1.5 min gradient, wavelength=254 nm); MS (ES): m/z=530/532 $^{35}Cl/^{37}Cl$ [M+1]$^+$.

Step 2: 2-[9-Chloro-7-(dimethyl-1H-1,2,3-triazol-5-yl)-5-[(S)-oxan-4-yl(phenyl)methyl]-5H-pyrido[3,2-b]indol-3-yl]propan-2-ol To a cold (−78° C.), stirred solution of (S)-methyl 9-chloro-7-(1,4-dimethyl-1H-1,2,3-triazol-5-yl)-5-(phenyl(tetrahydro-2H-pyran-4-yl)methyl)-5H-pyrido[3,2-b]indole-3-carboxylate (59.9 mg, 0.113 mmol) in THF (23 mL) under $N_2$ was added methylmagnesium bromide (3M in $Et_2O$, 603 μl, 1.81 mmol), stirred for 15 min, placed in an ice-water bath and stirred an additional 30 min. The reaction was quenched with sat. $NH_4Cl$ (5 mL), diluted with EtOAc, the organic phase was separated, concentrated, the residue dissolved in DMF (2 mL), filtered thru a 4μ membrane filter. The crude material was purified via preparative LC/MS with the following conditions: Column: Waters XBridge Shield RP18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-85% B over 25 minutes, then a 5-minute hold at 100% B; Flow: 20 mL/min. Fractions containing the desired product were combined and dried via centrifugal evaporation. Obtained the product (10.4 mg, 17%): HPLC: RT=1.656 min (Waters Acquity UPLC BEH C18, 2.1×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm; MS (ES): m/z=530 [M+1]$^+$; $^1$H NMR (500 MHz, DMSO-$d_6$) δ 8.75 (br s, 1H), 7.94 (s, 1H), 7.62 (br d, J=7.74 Hz, 2H), 7.39 (s, 1H), 7.29-7.36 (m, 2H), 7.19-7.28 (m, 1H), 5.89 (br d, J=11.44 Hz, 1H), 5.46 (s, 1H), 3.99 (br s, 2H), 3.88 (br d, J=10.43 Hz, 1H), 3.71 (br d, J=9.76 Hz, 1H), 3.24 (br t, J=11.61 Hz, 1H), 2.27 (br s, 3H), 1.73 (br d, J=11.78 Hz, 1H), 1.60 (br s, 7H), 1.19-1.35 (m, 1H), 0.92 (br d, J=12.12 Hz, 1H).

Example 14

2-[7-(Dimethyl-1,2-oxazol-4-yl)-5-[(S)-oxan-4-yl(phenyl)methyl]-5H-pyrido[3,2-b]indol-3-yl]propan-2-ol

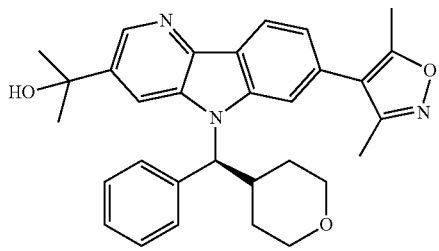 [SMILES: Cc1noc(C)c1-c1ccc2c3ncc(C(C)(C)O)cc3n([C@H](c3ccccc3)C3CCOCC3)c2c1]

Step 1: Methyl 7-(3,5-dimethylisoxazol-4-yl)-5H-pyrido[3,2-b]indole-3-carboxylate and methyl 7-(4-(3,5-dimethylisoxazol-4-yl)phenyl)-5H-pyrido[3,2-b]indole-3-carboxylate To a stirred suspension of methyl 7-bromo-5H-pyrido[3,2-b]indole-3-carboxylate (300.4 mg, 0.985 mmol), (3,5-dimethylisoxazol-4-yl)boronic acid (178.3 mg, 1.265 mmol), and $PdCl_2(dppf)$ (21.1 mg, 0.029 mmol) in THF (10.0 mL) at room temperature was added tripotassium phosphate (1.0 mL, 3.0 mmol), purged with $N_2$ (vacuum/$N_2$×3) and the reaction was heated at 75° C. with stirring for 5 h. The reaction was cooled to room temperature, concentrated in vacuo, and the residue was dissolved in EtOAc, washed with $H_2O$, sat. NaCl then dried over sodium sulfate, filtered, and concentrated in vacuo. The residue was dissolved in a mixture of DCM and THF, $SiO_2$ (6 g) was added, concentrated, dried under vacuum overnight. The material was then purified by flash chromatography (Teledyne ISCO CombiFlash Rf, gradient of 0% to 100% using solvent A/B=$CH_2Cl_2$/EtOAc over 15 column volumes, RediSep $SiO_2$ 40 g). A 77:23 mixture of methyl 7-(3,5-dimethylisoxazol-4-yl)-5H-pyrido[3,2-b]indole-3-carboxylate and methyl 7-(4-(3,5-dimethylisoxazol-4-yl)phenyl)-5H-pyrido[3,2-b]indole-3-carboxylate (247.6 mg) was obtained as a pale yellow solid: HPLC (for methyl 7-(3,5-dimethylisoxazol-4-yl)-5H-pyrido[3,2-b]indole-3-carboxylate): RT=0.76 min (Waters Acquity UPLC BEH C18 1.7 um 2.0×50 mm, $CH_3CN/H_2O/0.05\%$ TFA, 1 min gradient, wavelength=254 nm); MS (ES): m/z=322 [M+1]$^+$.

Step 2: (S)-Methyl 7-(3,5-dimethylisoxazol-4-yl)-5-(phenyl(tetrahydro-2H-pyran-4-yl)methyl)-5H-pyrido[3,2-b]indole-3-carboxylate and (S)-methyl 7-(4-(3,5-dimethylisoxazol-4-yl)phenyl)-5-(phenyl(tetrahydro-2H-pyran-4-yl)methyl)-5H-pyrido[3,2-b]indole-3-carboxylate To a cool (0° C.), stirred solution of methyl 7-(3,5-dimethylisoxazol-4-yl)-5H-pyrido[3,2-b]indole-3-carboxylate (57.2 mg, 0.178 mmol), (R)-phenyl(tetrahydro-2H-pyran-4-yl)methanol (71.0 mg, 0.369 mmol), and triphenylphosphine (96.4 mg, 0.368 mmol) in THF (3.6 mL) under $N_2$ was added DIAD (0.07 mL, 0.360 mmol) dropwise. The reaction was allowed to warm to room temperature as the bath warmed, and stirred overnight. The reaction was concentrated and dried under vacuum. The residue was purified by flash chromatography (Teledyne ISCO CombiFlash Rf, gradient of 0% to 100% using solvent A/B=$CH_2Cl_2$/EtOAc over 20 column volumes, RediSep $SiO_2$ 12 g, loaded as DCM solution). A mixture of (S)-methyl 7-(3,5-dimethylisoxazol-4-yl)-5-(phenyl(tetrahydro-2H-pyran-4-yl)methyl)-5H-pyrido[3,2-b]indole-3-carboxylate and (S)-methyl 7-(4-(3,5-dimethylisoxazol-4-yl)phenyl)-5-(phenyl(tetrahydro-2H-pyran-4-yl)methyl)-5H-pyrido[3,2-b]indole-3-carboxylate (229.8 mg) was obtained as an amber oil: HPLC (for (S)-methyl 7-(3,5-dimethylisoxazol-4-yl)-5-(phenyl(tetrahydro-2H-pyran-4-yl)methyl)-5H-pyrido[3,2-b]indole-3-carboxylate): HPCL: RT=1.00 min (Waters Acquity UPLC BEH C18 1.7 um 2.0×50 mm, $CH_3CN/H_2O/0.05\%$ TFA, 1 min gradient, wavelength=254 nm); MS (ES): m/z=496 [M+1]$^+$.

Step 3: 2-[7-(Dimethyl-1,2-oxazol-4-yl)-5-[(S)-oxan-4-yl(phenyl)methyl]-5H-pyrido[3,2-b]indol-3-yl]propan-2-ol To a cold (−78° C.), stirred solution of (S)-methyl 7-(3,5-dimethylisoxazol-4-yl)-5-(phenyl(tetrahydro-2H-pyran-4- yl)methyl)-5H-pyrido[3,2-b]indole-3-carboxylate (88 mg, 0.178 mmol) in THF (3.6 mL) under $N_2$ was added methyl magnesium bromide (3M in $Et_2O$, 1.2 mL, 3.60 mmol), stirred for 15 min, placed in 0° C. bath, and stirred an additional 50 min. To the reaction was added 4 mL sat. $NH_4Cl$, warmed to room temperature, diluted with EtOAc, the organic phase was separated, concentrated, dissolved in 2 mL DMF, filtered through a 4µ membrane filter. The crude material was purified via preparative LC/MS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-80% B over 20 minutes, then a 5-minute hold at 100% B; Flow: 20 mL/min. Fractions containing the desired product were combined and dried via centrifugal evaporation. Obtained the product (24.5 mg, 28%): HPCL: RT=1.828 min (Waters Acquity UPLC BEH C18, 2.1×50 mm, 1.7-µm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm); MS (ES): m/z=496 [M+1]$^+$; $^1$H NMR (500 MHz, DMSO-$d_6$) δ 8.63 (s, 1H), 8.36 (br s, 1H), 8.22 (d, J=7.74 Hz, 1H), 7.63 (br d, J=7.74 Hz, 2H), 7.28-7.37 (m, 2H), 7.19-7.27 (m, 2H), 5.80 (br d, J=11.11 Hz, 1H), 3.88 (br d, J=10.43 Hz, 1H), 3.72 (br d, J=9.42 Hz, 1H), 3.25 (br t, J=11.44 Hz, 1H), 2.45 (br s, 3H), 2.28 (br s, 3H), 1.72 (br d, J=12.45 Hz, 1H), 1.59 (s, 7H), 1.20-1.36 (m, 1H), 0.95 (br d, J=12.12 Hz, 1H).

Example 15

2-[7-(Dimethyl-1,2-oxazol-4-yl)-5-[(S)-(2-fluorophenyl)(oxan-4-yl)methyl]-5H-pyrido[3,2-b]indol-3-yl]propan-2-ol

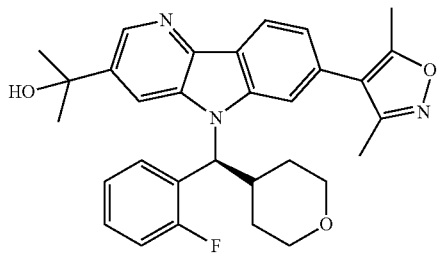 [SMILES: Cc1noc(C)c1-c1ccc2c3ncc(C(C)(C)O)cc3n([C@H](c3ccccc3F)C3CCOCC3)c2c1]

Step 1: (S)-Methyl 7-(3,5-dimethylisoxazol-4-yl)-5-((2-fluorophenyl)(tetrahydro-2H-pyran-4-yl)methyl)-5H-pyrido[3,2-b]indole-3-carboxylate and (S)-methyl 7-(4-(3,5-dimethylisoxazol-4-yl)phenyl)-5-((2-fluorophenyl)(tetrahydro-2H-pyran-4-yl)methyl)-5H-pyrido[3,2-b]indole-3-carboxylate To a cool (0° C.), stirred solution of methyl 7-(3,5-dimethylisoxazol-4-yl)-5H-pyrido[3,2-b]indole-3-carboxylate (58.4 mg, 0.182 mmol), (R)-(2-fluorophenyl)(tetrahydro-2H-pyran-4-yl)methanol (105.9 mg, 0.504 mmol), and triphenylphosphine (101.9 mg, 0.389 mmol) in THF (3.6 mL) under $N_2$ was added DIAD (0.07 mL, 0.360 mmol) dropwise, the reaction was allowed to warm to room temperature as bath warmed, and stirred overnight. The reaction was concentrated and dried under vacuum. The residue was purified by flash chromatography (Teledyne ISCO Combi-Flash Rf, gradient of 0% to 100% using solvent A/B=$CH_2Cl_2$/acetone over 30 column volumes, RediSep $SiO_2$ 12 g, loaded as DCM solution). A mixture of (S)-methyl dimethylisoxazol-4-yl)-5-((2-fluorophenyl)(tetrahydro-2H-pyran-4-yl)methyl)-5H-pyrido[3,2-b]indole-3-carboxylate and (S)-methyl 7-(4-(3,5-dimethylisoxazol-4-yl)phenyl)-5-((2-fluorophenyl)(tetrahydro-2H-pyran-4-yl)methyl)-5H-pyrido[3,2-b]indole-3-carboxylate (134.0 mg) was obtained as an amber oil: HPLC (for (S)-methyl 7-(3,5-dimethylisoxazol-4-yl)-5-((2-fluorophenyl)(tetrahydro-2H-pyran-4-yl)methyl)-5H-pyrido[3,2-b]indole-3-carboxylate): RT=1.00 min (Waters Acquity UPLC BEH C18 1.7 um 2.0×50 mm, $CH_3CN/H_2O$/0.05% TFA, 1 min gradient, wavelength=254 nm); MS (ES): m/z=514 [M+1]$^+$.

Step 2: 2-[7-(Dimethyl-1,2-oxazol-4-yl)-5-[(S)-(2-fluorophenyl)(oxan-4-yl)methyl]-5H-pyrido[3,2-b]indol-3-yl]propan-2-ol To a cold (−78° C.), stirred solution of (S)-methyl 7-(3,5-dimethylisoxazol-4-yl)-5-((2-fluorophenyl)(tetrahydro-2H-pyran-4-yl)methyl)-5H-pyrido[3,2-b]indole-3-carboxylate (93 mg, 0.182 mmol) in THF (3.7 mL) under $N_2$ was added methyl magnesium bromide (3M in $Et_2O$, 1.2 mL, 3.60 mmol), stirred for 15 min, placed in 0° C. bath and stirred an addition al 40 min. To the reaction was added 4 mL sat. $NH_4Cl$, warmed to room temperature, diluted with EtOAc, the organic phase was separated, concentrated, dissolved in 2 mL DMF and filtered through a 4µ membrane filter. The crude material was purified via preparative LC/MS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-95% B over 20 minutes, then a 5-minute hold at 100% B; Flow: 20 mL/min. Fractions containing the desired product were combined and dried via centrifugal evaporation. Obtained the product (22.3 mg, 23%): HPCL: RT=1.814 min (Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm); MS (ES): m/z=514 [M+1]$^+$; $^1$H NMR (500 MHz, DMSO-$d_6$) δ 8.63 (br s, 1H), 8.15-8.25 (m, 2H), 7.27-7.39 (m, 2H), 7.23 (br d, J=7.74 Hz, 1H), 7.10 (br t, J=9.09 Hz, 1H), 5.98 (br d, J=10.77 Hz, 1H), 3.84-3.92 (m, 1H), 3.70 (br d, J=9.42 Hz, 1H), 3.45-3.55 (m, 1H), 3.13-3.25 (m, 1H), 2.44 (br s, 3H), 2.28 (br s, 3H), 1.74 (br d, J=11.78 Hz, 1H), 1.48-1.68 (m, 7H), 1.32 (br d, J=8.75 Hz, 1H), 0.76 (br d, J=12.45 Hz, 1H).

Example 16

2-{7-[4-($^2H_3$)Methyl-1-methyl-1H-1,2,3-triazol-5-yl]-5-[(S)-oxan-4-yl(phenyl)methyl]-5H-pyrido[3,2-b]indol-3-yl}propan-2-ol

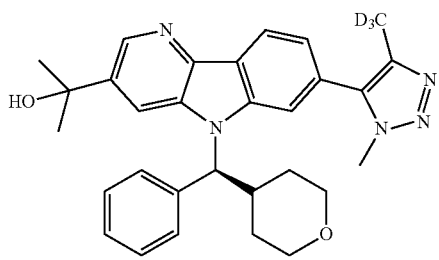 [SMILES: [2H]C([2H])([2H])c1nnn(C)c1-c1ccc2c3ncc(C(C)(C)O)cc3n([C@H](c3ccccc3)C3CCOCC3)c2c1]

Step 1: (S)-Methyl 7-bromo-5-(phenyl(tetrahydro-2H-pyran-4-yl)methyl)-5H-pyrido[3,2-b]indole-3-carboxylate and (S)-methyl 7-(4-bromophenyl)-5-(phenyl(tetrahydro-2H-pyran-4-yl)methyl)-5H-pyrido[3,2-b]indole-3-carboxylate To a 40 mL I-Chem vial equipped with a stir bar under ambient atmosphere, was added methyl 7-bromo-5H-pyrido[3,2-b]indole-3-carboxylate (99.6 mg, 0.326 mmol), (R)-phenyl(tetrahydro-2H-pyran-4-yl)methanol (127.9 mg, 0.665 mmol), and triphenylphosphine (180.2 mg, 0.687 mmol). The vial was sealed with a PTFE-lined septum screw-cap, THF (6.6 mL) was added, then cooled to 0° C. To the reaction was added DIAD (0.13 mL, 0.669 mmol), stirred for 5 min, then the vial was allowed to warm to room temperature and stirred overnight. The reaction was concentrated in vacuo and dried under vacuum. The residue was purified by flash chromatography (Teledyne ISCO CombiFlash Rf, gradient of 0% to 100% using solvent A/B=hexanes/EtOAc over 12 column volumes, RediSep $SiO_2$ 40 g, loaded as DCM solution). Fractions containing product were collected and concentrated. The gummy residue was dissolved in a small amount of MeOH. Water was added and a solid precipitated. It was collected by filtration and air dried overnight. A 83:17 mixture of (S)-methyl 7-bromo-5-(phenyl(tetrahydro-2H-pyran-4-yl)methyl)-5H-pyrido[3,2-b]indole-3-carboxylate and (S)-methyl 7-(4-bromophenyl)-5-(phenyl(tetrahydro-2H-pyran-4-yl)methyl)-5H-pyrido[3,2-b]indole-3-carboxylate (125.8 mg) was obtained as a cream solid: HPLC (for (S)-methyl 7-bromo-5-(phenyl(tetrahydro-2H-pyran-4-yl)methyl)-5H-pyrido[3,2-b]indole-3-carboxylate): RT=1.09 min (Waters Acquity UPLC BEH C18 1.7 um 2.0×50 mm, $CH_3CN/H_2O$/0.05% TFA, 1 min gradient, wavelength=254 nm); MS (ES): m/z=479/481 $^{79}Br/^{81}Br$ [M+1]$^+$.

Step 2: Methyl 7-[4-($^2H_3$)methyl-1-methyl-1H-1,2,3-triazol-5-yl]-5-[(S)-oxan-4-yl(phenyl)methyl]-5H-pyrido[3,2-b]indole-3-carboxylate In a 4 mL vial was a mixture of (S)-methyl 7-bromo-5-(phenyl(tetrahydro-2H-pyran-4-yl)methyl)-5H-pyrido[3,2-b]indole-3-carboxylate and (S)-methyl 7-(4-bromophenyl)-5-(phenyl(tetrahydro-2H-pyran-4-yl)methyl)-5H-pyrido[3,2-b]indole-3-carboxylate (51.7 mg), 4-($^2H_3$)methyl-1-((trimethylsilyl)methyl)-1H-1,2,3-triazole (46.0 mg, 0.267 mmol), and tetrabutylammonium acetate (63.5 mg, 0.211 mmol) in NMP (0.2 mL) to give a white suspension. Tris(dibenzylideneacetone)dipalladium-chloroform adduct (10.6 mg, 10.2 μmol) was added, sealed vial under $N_2$, then heated to 100° C. in a heating block with stirring for 3 h. The reaction removed from the heating block, cooled to room temperature, then to the reaction was added TBAF (1M in THF, 1.0 mL, 1.0 mmol) and stirred for 50 min. The reaction was diluted with EtOAc, washed with 10% LiCl, sat. NaCl then dried over sodium sulfate, filtered, and concentrated in vacuo. The residue was purified by flash chromatography (Teledyne ISCO CombiFlash Rf, gradient of 0% to 100% using solvent A/B=$CH_2Cl_2$/acetone over 50 column volumes, RediSep $SiO_2$ 12 g, loaded as DCM solution). The product (12.2 mg, 23%) was obtained as a cream solid: HPLC: RT=0.91 min (Waters Acquity UPLC BEH C18 1.7 um 2.0×50 mm, $CH_3CN/H_2O$/0.05% TFA, 1 min gradient, wavelength=254 nm); MS (ES): m/z=499 [M+1]$^+$.

Step 3: 2-{7-[4-($^2H_3$)Methyl-1-methyl-1H-1,2,3-triazol-5-yl]-5-[(S)-oxan-4-yl(phenyl)methyl]-5H-pyrido[3,2-b]indol-3-yl}propan-2-ol To a cold (−78° C.), stirred solution of methyl 7-[4-($^2H_3$)methyl-1-methyl-1H-1,2,3-triazol-5-yl]-5-[(S)-oxan-4-yl(phenyl)methyl]-5H-pyrido[3,2-b]indole-3-carboxylate (12.2 mg, 0.024 mmol) in THF (1.0 mL) under $N_2$ was added methyl magnesium bromide (3M in $Et_2O$, 0.17 mL, 0.510 mmol), stirred for 20 min, placed in a 0° C. bath and stirred an additional 20 min. To the reaction was added 4 mL sat. $NH_4Cl$, warmed to room temperature, diluted with EtOAc, the organic phase was separated, concentrated. Dissolved in 2 mL DMF, filtered through a 4 μm membrane filter. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-75% B over 20 minutes, then a 5-minute hold at 100% B; Flow: 20 mL/min. Fractions containing the desired product were combined and dried via centrifugal evaporation. Obtained the product (3.4 mg, 27%): HPLC: RT=2.176 min (Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm); MS (ES): m/z=499 [M+1]$^+$; $^1H$ NMR (500 MHz, DMSO-$d_6$) δ 8.66 (s, 1H), 8.39 (br s, 1H), 8.29 (d, J=8.08 Hz, 1H), 7.64 (br d, J=7.41 Hz, 2H), 7.27-7.36 (m, 3H), 7.19-7.27 (m, 1H), 5.83 (br d, J=11.11 Hz, 1H), 3.99 (br s, 2H), 3.83-3.92 (m, 1H), 3.72 (br d, J=10.10 Hz, 1H), 3.25 (br t, J=11.44 Hz, 1H), 2.54 (s, 1H), 1.71 (br d, J=12.79 Hz, 1H), 1.60 (br s, 6H), 1.21-1.35 (m, 1H), 0.96 (br d, J=11.44 Hz, 1H).

Examples 17 and 18

2-[7-(Dimethyl-1,2-oxazol-4-yl)-6-fluoro-5-[(S)-oxan-4-yl(phenyl)methyl]-5H-pyrido[3,2-b]indol-3-yl]propan-2-ol and 2-[7-(dimethyl-1,2-oxazol-4-yl)-8-fluoro-5-[(S)-oxan-4-yl(phenyl)methyl]-5H-pyrido[3,2-b]indol-3-yl]propan-2-ol

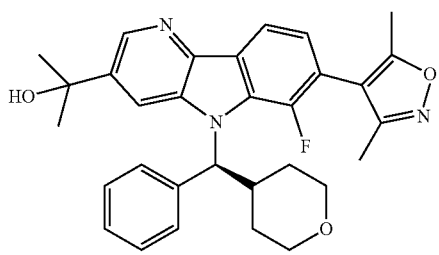

Example 17

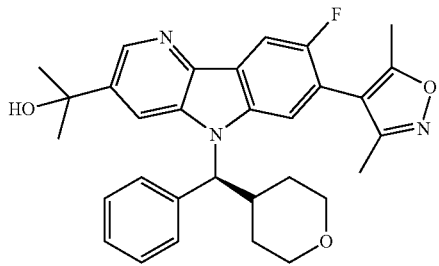

Example 18

Step 1: Methyl 6-(4-bromo-3-fluorophenyl)-5-nitronicotinate and methyl 6-(4'-bromo-2,3'-difluoro-[1,1'-biphenyl]-4-yl)-5-nitronicotinate To a stirred solution of methyl 6-chloro-5-nitronicotinate (759.7 mg, 3.51 mmol), (4-bromo-3-fluorophenyl)boronic acid (879.1 mg, 4.02 mmol), and $PdCl_2$(dppf) (121.1 mg, 0.166 mmol) in THF (33 mL) was added tripotassium phosphate (3M in $H_2O$, 3.3 mL, 9.90 mmol), purged with $N_2$ (vacuum/$N_2 \times 3$), and the reaction was heated at 75° C. with stirring for 50 min. The reaction was cooled to room temperature, concentrated. The residue was dissolved in EtOAc, filtered through Celite, washed with EtOAc, then the filtrate washed with $H_2O$ and sat. NaCl, dried over sodium sulfate, filtered, and concentrated. The residue was purified by flash chromatography (Teledyne ISCO CombiFlash Rf, gradient of 0% to 100% using solvent A/B=$CH_2Cl_2$/EtOAc over 15 column volumes, RediSep $SiO_2$ 80 g, loaded as DCM solution). A 69:25 mixture (by LCMS) of methyl 6-(4-bromo-3-fluorophenyl)-5-nitronicotinate and methyl 6-(4'-bromo-2,3'-difluoro-[1,1'-biphenyl]-4-yl)-5-nitronicotinate (900.9 mg) was obtained as a pale yellow solid: HPLC of methyl 6-(4-bromo-3-fluorophenyl)-5-nitronicotinate: RT=1.04 min (Waters Acquity UPLC BEH C18 1.7 um 2.0×50 mm, $CH_3CN/H_2O$/0.05% TFA, 1 min gradient, wavelength=254 nm); MS (ES): m/z=355/357 $^{79}Br/^{81}Br$ $[M+1]^+$; HPLC of methyl 6-(4'-bromo-2,3'-difluoro-[1,1'-biphenyl]-4-yl)-5-nitronicotinate: RT=1.17 min; MS (ES): m/z=449/451 $^{79}Br/^{81}Br$ $[M+1]^+$;

Step 2: Methyl 7-bromo-6-fluoro-5H-pyrido[3,2-b]indole-3-carboxylate, methyl 7-bromo-8-fluoro-5H-pyrido[3,2-b]indole-3-carboxylate, methyl 7-(4-bromo-3-fluorophenyl)-6-fluoro-5H-pyrido[3,2-b]indole-3-carboxylate and methyl 7-(4-bromo-3-fluorophenyl)-8-fluoro-5H-pyrido[3,2-b]indole-3-carboxylate In a 100 mL RB flask was added a mixture of impure methyl 6-(4-bromo-3-fluorophenyl)-5-nitronicotinate (900.9 mg, 2.54 mmol) and 1,2-bis(diphenylphosphino)ethane (1.21 g, 3.04 mmol) in 1,2-dichlorobenzene (10 mL) and the flask was heated in a pre-heated heating block at 170° C. for 55 min. Cooled to room temperature, then concentrated under high vacuum. The residue was dissolved in THF and a small amount of MeOH, $SiO_2$ (10 g) was added, concentrated then dried under vacuum. The material was then purified by flash chromatography (Teledyne ISCO CombiFlash Rf, gradient of 0% to 70% using solvent A/B=$CH_2Cl_2$/EtOAc over 12 column volumes, RediSep $SiO_2$ 80 g). A 39:41:11:9 mixture of products including both isomeric products, and isomeric homologated biphenyl-containing byproducts (509.6 mg) was obtained as a yellow solid: HPLC of isomer 1: RT=0.88 min (Waters Acquity UPLC BEH C18 1.7 um 2.0×50 mm, $CH_3CN/H_2O$/0.05% TFA, 1 min gradient, wavelength=254 nm); MS (ES): m/z=323/325 $^{79}Br/^{81}Br$ $[M+1]^+$; HPLC of isomer 2: RT=0.90 min (Waters Acquity UPLC BEH C18 1.7 um 2.0×50 mm, $CH_3CN/H_2O$/0.05% TFA, 1 min gradient, wavelength=254 nm); MS (ES): m/z=323/325 $^{79}Br/^{81}Br$ $[M+1]^+$; HPLC of homologated biproducts not given.

Step 3: Methyl 7-(3,5-dimethylisoxazol-4-yl)-6-fluoro-5H-pyrido[3,2-b]indole-3-carboxylate and methyl 7-(3,5-dimethylisoxazol-4-yl)-8-fluoro-5H-pyrido[3,2-b]indole-3-carboxylate To a stirred solution of impure methyl 7-bromo-6-fluoro-5H-pyrido[3,2-b]indole-3-carboxylate (116.7 mg, 0.361 mmol), (3,5-dimethylisoxazol-4-yl)boronic acid (69.8 mg, 0.495 mmol), and $PdCl_2$(dppf) (20.3 mg, 0.028 mmol) in THF (3.6 mL) at room temperature was added tripotassium phosphate (0.36 mL, 1.08 mmol), purged with $N_2$ (vacuum/$N_2 \times 3$), and the reaction was heated at 75° C. with stirring for 2 h. The reaction was cooled to room temperature, diluted with EtOAc, washed with $H_2O$, sat. NaCl then dried over sodium sulfate, filtered, and concentrated in vacuo. The residue was dissolved in a mixture of DCM and THF, $SiO_2$ (6 g) was added, concentrated, dried under vacuum overnight. The material was then purified by flash chromatography (Teledyne ISCO CombiFlash Rf, gradient of 0% to 20% using solvent A/B=$CH_2Cl_2$/MeOH over 15 column volumes, RediSep $SiO_2$ 40 g). A mixture of methyl 7-(3,5-dimethylisoxazol-4-yl)-6-fluoro-5H-pyrido[3,2-b]indole-3-carboxylate and methyl 7-(3,5-dimethylisoxazol-4-yl)-8-fluoro-5H-pyrido[3,2-b]indole-3-carboxylate (108.6 mg, 89% yield)) was obtained as a yellow solid: HPLC (products coelute): RT=0.83 min (Waters Acquity UPLC BEH C18 1.7 um 2.0×50 mm, $CH_3CN/H_2O$/0.05% TFA, 1 min gradient, wavelength=254 nm); MS (ES): m/z=340 $[M+1]^+$.

Step 4: Methyl 7-(3,5-dimethylisoxazol-4-yl)-6-fluoro-5-((S)-phenyl (tetrahydro-2H-pyran-4-yl)methyl)-5H-pyrido[3,2-b]indole-3-carboxylate and methyl 7-(3,5-dimethylisoxazol-4-yl)-8-fluoro-5-((S)-phenyl(tetrahydro-2H-pyran-4-yl)methyl)-5H-pyrido[3,2-b]indole-3-carboxylate To a cool (0° C.), stirred solution of methyl 7-(3,5-dimethylisoxazol-4-yl)-6-fluoro-5H-pyrido[3,2-b]indole-3- carboxylate and methyl 7-(3,5-dimethylisoxazol-4-yl)-8-fluoro-5H-pyrido[3,2-b]indole-3-carboxylate (108 mg, 0.319 mmol), (R)-phenyl(tetrahydro-2H-pyran-4-yl)methanol (128.5 mg, 0.668 mmol), and triphenylphosphine (174.0 mg, 0.663 mmol) in THF (6.4 mL) under $N_2$ was added DIAD (0.13 mL, 0.669 mmol) dropwise, the reaction was allowed to warm to room temperature as bath warmed, and stirred overnight. Reaction concentrated, dried under vacuum. The residue was purified by flash chromatography (Teledyne ISCO CombiFlash Rf, gradient of 0% to 60% using solvent A/B=$CH_2Cl_2$/acetone over 20 column volumes, RediSep $SiO_2$ 24 g, loaded as DCM solution). The mixture of regioisomers (310.9 mg) was obtained as an amber oil: HPLC showed both regioisomers: RT=1.06/1.07 min (Waters Acquity UPLC BEH C18 1.7 um 2.0×50 mm, $CH_3CN/H_2O$/0.05% TFA, 1 min gradient, wavelength=254 nm); MS (ES): m/z=514 [M+1]$^+$.

Step 5: 2-[7-(Dimethyl-1,2-oxazol-4-yl)-6-fluoro-5-[(S)-oxan-4-yl(phenyl)methyl]-5H-pyrido[3,2-b]indol-3-yl]propan-2-ol and 2-[7-(dimethyl-1,2-oxazol-4-yl)-8-fluoro-5-[(S)-oxan-4-yl(phenyl)methyl]-5H-pyrido[3,2-b]indol-3-yl]propan-2-ol

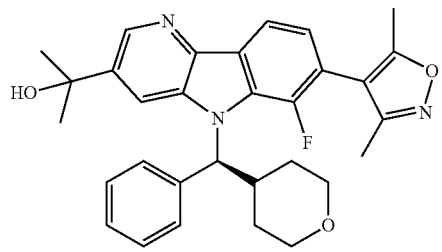

Example 17

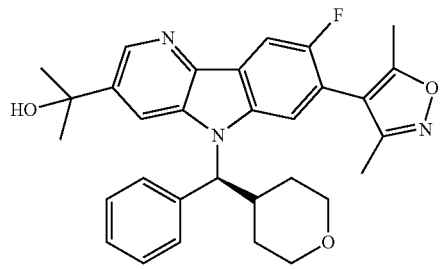

Example 18

To a cold (−78° C.), stirred solution of methyl 7-(3,5-dimethylisoxazol-4-yl)-6-fluoro-5-((S)-phenyl(tetrahydro-2H-pyran-4-yl)methyl)-5H-pyrido[3,2-b]indole-3-carboxylate (164 mg, 0.319 mmol) in THF (6.4 mL) under $N_2$ was added methyl magnesium bromide (3M in $Et_2O$, 2.1 mL, 6.30 mmol), stirred for 15 min, placed in 0° C. bath and stirred an additional 30 min. To the reaction was added 4 mL sat. $NH_4Cl$, warmed to room temperature, diluted with EtOAc, the organic phase was separated, washed with brine, dried over sodium sulfate, filtered, and concentrated. The residue was purified by flash chromatography (Teledyne ISCO CombiFlash Rf, gradient of 0% to 100% using solvent A/B=$CH_2Cl_2$/acetone over 20 column volumes, RediSep $SiO_2$ 40 g, loaded as DCM solution). Fractions containing both isomers were collected and concentrated, and the mixture was further purified by SFC (Berger SFC MGII, Column: Chiral OD-H 25×3 cm ID, 5 μm, Flow rate: 85.0 mL/min, Mobile Phase: 80/20 $CO_2$/MeOH, Detector Wavelength: 220 nm, Sample Prep and Inj. Volume: 3000 μL of 106 mg dissolved in 7 mL MeOH). Obtained 2-(7-(3,5-dimethylisoxazol-4-yl)-6-fluoro-5-((S)-phenyl(tetrahydro-2H-pyran-4-yl)methyl)-5H-pyrido[3,2-b]indol-3-yl)propan-2-ol (23.5 mg, 14%): HPLC: RT=0.89 min (Waters Acquity UPLC BEH C18 1.7 um 2.0×50 mm, $CH_3CN/H_2O$/0.05% TFA, 1 min gradient, wavelength=254 nm); MS (ES): m/z=514 [M+1]$^+$; $^1$H NMR (400 MHz, DMSO-$d_6$) δ 8.69 (br s, 1H), 8.07 (d, J=7.92 Hz, 1H), 7.42-7.68 (m, 2H), 7.29-7.37 (m, 1H), 7.19-7.29 (m, 2H), 5.90 (br d, J=11.00 Hz, 1H), 5.36 (s, 1H), 3.89 (br d, J=10.12 Hz, 1H), 3.76 (br d, J=11.22 Hz, 1H), 3.44-3.57 (m, 1H), 1.81 (br s, 1H), 1.56 (br s, 7H), 1.24-1.40 (m, 1H), 1.04 (br d, J=10.56 Hz, 1H); and 2-(7-(3,5-dimethylisoxazol-4-yl)-8-fluoro-5-((S)-phenyl(tetrahydro-2H-pyran-4-yl)methyl)-5H-pyrido[3,2-b]indol-3-yl)propan-2-ol (21.4 mg, 13%): HPLC: RT=0.87 min (Waters Acquity UPLC BEH C18 1.7 um 2.0×50 mm, $CH_3CN/H_2O$/0.05% TFA, 1 min gradient, wavelength=254 nm); MS (ES): m/z=514 [M+1]$^+$; $^1$H NMR (400 MHz, DMSO-$d_6$) δ 8.66 (d, J=1.54 Hz, 1H), 8.38 (br s, 1H), 8.01 (d, J=9.68 Hz, 1H), 7.96 (br s, 1H), 7.63 (d, J=7.26 Hz, 2H), 7.29-7.35 (m, 2H), 7.19-7.27 (m, 1H), 5.80 (d, J=11.22 Hz, 1H), 3.89 (br d, J=9.24 Hz, 1H), 3.74 (br d, J=9.24 Hz, 1H), 3.42-3.54 (m, 1H), 2.37 (s, 3H), 2.20 (s, 3H), 1.65-1.75 (m, 1H), 1.60 (s, 7H), 1.20-1.36 (m, 1H), 0.98 (br d, J=12.76 Hz, 1H).

Example 19

2-[7-(Dimethyl-1H-1,2,3-triazol-5-yl)-8-fluoro-5-[(S)-oxan-4-yl(phenyl)methyl]-5H-pyrido[3,2-b]indol-3-yl]propan-2-ol

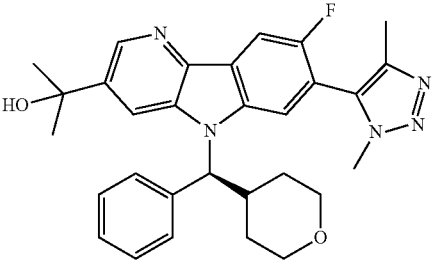 [SMILES: Cc1nnn(C)c1-c1cc2c(cc1F)c1ncc(C(C)(C)O)cc1n2[C@H](c1ccccc1)C1CCOCC1]

Step 1: Methyl 7-(1,4-dimethyl-1H-1,2,3-triazol-5-yl)-6-fluoro-5H-pyrido[3,2-b]indole-3-carboxylate and methyl 7-(1,4-dimethyl-1H-1,2,3-triazol-5-yl)-8-fluoro-5H-pyrido[3,2-b]indole-3-carboxylate A stirred solution of methyl 7-bromo-6-fluoro-5H-pyrido[3,2-b]indole-3-carboxylate, the 8-fluoro regiosomer and the homologs (372.8 mg, 1.15 mmol), 1,4-dimethyl-5-(tributylstannyl)-1H-1,2,3-triazole (593.2 mg, 1.54 mmol), and triethylamine (0.41 mL, 2.94 mmol) in DMF (23 mL) at room temperature was bubbled with $N_2$ for 5 min. During the bubbling, copper(I) iodide (65.4 mg, 0.343 mmol) and Pd(PPh$_3$)$_4$ (130.7 mg, 0.113 mmol) were added, the flask sealed with a septum, and the reaction was heated at 95° C. with stirring overnight. To the reaction was added additional stannane (735 mg), Pd(PPh$_3$)$_4$ (22.5 mg), and CuI (125 mg), reheated to 95° C. again overnight. The reaction was cooled to room temperature, concentrated in vacuo, and the residue was dissolved in EtOAc, filtered through Celite, washed pad with EtOAc, the filtrate was then concentrated. The residue was purified by flash chromatography (Teledyne ISCO CombiFlash Rf, gradient of 0% to 15% using solvent A/B=CH$_2$Cl$_2$/MeOH over 20 column volumes, RediSep SiO$_2$ 40 g, loaded as DCM solution). Obtained 322 mg dark yellow solid. LCMS showed a mixture of product isomers. Residue was dissolved in 5 mL DMF, repurified on reverse phase ISCO (gradient of 0% to 100% using solvent A/B=Water w/0.1% TFA to CH$_3$CN w/0.1% TFA over 20 column volumes, C18-100 g Gold). Fractions containing product were collected and partially concentrated. The aqueous phase was made basic with sat. NaHCO$_3$, extracted with EtOAc (3×50 mL), the combined organic phases were washed with brine, dried over sodium sulfate, filtered, and concentrated. Obtained a mixture of regiosomers (113.9 mg): HPLC: RT=0.74 min (Waters Acquity UPLC BEH C18 1.7 um 2.0×50 mm, CH$_3$CN/H$_2$O/0.05% TFA, 1 min gradient, wavelength=254 nm); MS (ES): m/z=514 [M+1]$^+$.

Step 2: Methyl 7-(1,4-dimethyl-1H-1,2,3-triazol-5-yl)-6-fluoro-5-((S)-phenyl(tetrahydro-2H-pyran-4-yl)methyl)-5H-pyrido[3,2-b]indole-3-carboxylate and methyl 7-(1,4-dimethyl-1H-1,2,3-triazol-5-yl)-8-fluoro-5-((S)-phenyl(tetrahydro-2H-pyran-4-yl)methyl)-5H-pyrido[3,2-b]indole-3-carboxylate To a stirred solution of a mixture of methyl 7-(1,4-dimethyl-1H-1,2,3-triazol-5-yl)-6-fluoro-5H-pyrido[3,2-b]indole-3-carboxylate and methyl 7-(1,4-dimethyl-1H-1,2,3-triazol-5-yl)-8-fluoro-5H-pyrido[3,2-b]indole-3-carboxylate (113.9 mg, 0.336 mmol) and (R)-phenyl(tetrahydro-2H-pyran-4-yl)methyl methanesulfonate (186.8 mg, 0.691 mmol) in DMF (3.3 mL) under N$_2$ was added Cs$_2$CO$_3$ (329.7 mg, 1.01 mmol), and the reaction was heated at 50° C. with stirring over 48 h. To the reaction was added additional mesylate (145.7 mg) and Cs$_2$CO$_3$ (338.4 mg), heated to 80° C. for 6 h. Reaction cooled to room temperature, diluted with EtOAc, washed with 10% LiCl (3×), sat. NaCl then dried over sodium sulfate, filtered, and concentrated in vacuo. The residue was purified by flash chromatography (Teledyne ISCO CombiFlash Rf, gradient of 0% to 100% using solvent A/B=CH$_2$Cl$_2$/acetone over 20 column volumes, RediSep SiO$_2$ 40 g, loaded as DCM solution). Obtained 145.6 mg yellow solid. The residue was dissolved in DMF (5 mL), was purified by Preparative HPLC (Luna 5u C18 (21.2×100 mm), H$_2$O/MeOH w/0.1% TFA, 10 min, 254 nm). LCMS of yellow solid showed a single peak with m/z consistent with product. Ratio of regioisomers unknown. $^1$H NMR of yellow solid suggests predominantly the 8-F regioisomer, small amount of 6-F isomer. Obtained the product (methyl 7-(1,4-dimethyl-1H-1,2,3-triazol-5-yl)-8-fluoro-5-((S)-phenyl(tetrahydro-2H-pyran-4-yl)methyl)-5H-pyrido[3,2-b]indole-3-carboxylate (48.8 mg, 28%)): HPLC: RT=0.96 min (Waters Acquity UPLC BEH C18 1.7 um 2.0×50 mm, CH$_3$CN/H$_2$O/0.05% TFA, 1 min gradient, wavelength=254 nm); MS (ES): m/z=514 [M+1]$^+$.

Step 3: 2-[7-(Dimethyl-1H-1,2,3-triazol-5-yl)-8-fluoro-5-[(S)-oxan-4-yl(phenyl)methyl]-5H-pyrido[3,2-b]indol-3-yl]propan-2-ol To a cold (−78° C.), stirred solution of methyl 7-(1,4-dimethyl-1H-1,2,3-triazol-5-yl)-8-fluoro-5-((S)-phenyl(tetrahydro-2H-pyran-4-yl)methyl)-5H-pyrido[3,2-b]indole-3-carboxylate (48.4 mg, 0.094 mmol) in THF (1.9 mL) under N$_2$ was added methylmagnesium bromide (3 M in Et$_2$O, 628 μl, 1.89 mmol), stirred for 15 min, then warmed to 0° C., and stirred an additional 45 min. The reaction was quenched with sat. NH$_4$Cl, diluted with EtOAc, the organic phase was separated, washed with sat. NaCl then dried over sodium sulfate, filtered, and concentrated. Dissolved in 2 mL DMF, purified via preparative LC/MS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-80% B over 20 minutes, then a 5-minute hold at 100% B; Flow: 20 mL/min. Obtained the product (25.9 mg, 54%): HPLC: RT=2.279 min (Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm); MS (ES): m/z=514 [M+1]$^+$; $^1$H NMR (500 MHz, DMSO-d$_6$) δ 8.69 (s, 1H), 8.41 (br s, 1H), 8.10 (d, J=9.42 Hz, 1H), 7.63 (br d, J=7.74 Hz, 2H), 7.28-7.37 (m, 2H), 7.20-7.27 (m, 1H), 5.82 (br d, J=11.44 Hz, 1H), 3.89 (br d, J=13.13 Hz, 2H), 3.73 (br d, J=8.75 Hz, 1H), 3.47 (br t, J=11.28 Hz, 1H), 3.25 (br t, J=11.28 Hz, 1H), 2.54 (s, 6H), 2.20 (br s, 3H), 1.68 (br d, J=12.79 Hz, 1H), 1.60 (s, 7H), 1.23-1.36 (m, 1H), 0.98 (br d, J=12.79 Hz, 1H).

Example 20

2-[7-(Dimethyl-1H-1,2,3-triazol-5-yl)-6-fluoro-5-[(S)-oxan-4-yl(phenyl)methyl]-5H-pyrido[3,2-b]indol-3-yl]propan-2-ol

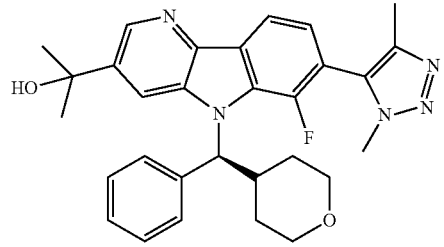 [SMILES: Cc1nnn(C)c1-c1ccc2c3ncc(C(C)(C)O)cc3n([C@H](c3ccccc3)C3CCOCC3)c2c1F]

Step 1: Methyl 7-bromo-6-fluoro-5H-pyrido[3,2-b]indole-3-carboxylate and methyl 7-bromo-8-fluoro-5H-pyrido[3,2-b]indole-3-carboxylate In a 100 mL RB flask was added a mixture of impure methyl 6-(4-bromo-3-fluorophenyl)-5-nitronicotinate (1.6671 g, 4.69 mmol) and 1,2-bis(diphenylphosphino) ethane (2.25 g, 5.65 mmol) in 1,2-dichlorobenzene (19 mL) and the flask was heated in a pre-heated heating block at 170° C. for 35 min, cooled to room temperature, then concentrated under high vacuum. The residue was dissolved in THF and a small amount of MeOH, SiO$_2$ (17 g) was added, concentrated then dried under vacuum. The material was then purified by flash chromatography (Teledyne ISCO CombiFlash Rf, gradient of 0% to 20% using solvent A/B=CH$_2$Cl$_2$/MeOH over 12 column volumes, RediSep SiO$_2$ 120 g). Obtained 3.66 g tan solid. The material was further purified by flash chromatography (Teledyne ISCO CombiFlash Rf, gradient of 0% to 100% using solvent A/B=hexane/EtOAc over 18 column volumes, RediSep GOLD SiO$_2$ 220 g). Obtained several clean fractions of first eluting isomer, and several fractions of a mixture of compounds. Clean material combined and set aside, and mixed fractions repurified by flash chromatography (Teledyne ISCO CombiFlash Rf, gradient of 0% to 50% using solvent A/B=hexanes/EtOAc over 20 column volumes, RediSep SiO$_2$ 120 g). Fractions of the first eluting isomer were combined with those obtained above. $^1$H NMR showed this to be the 6-F isomer (methyl 7-bromo-6-fluoro-5H-pyrido[3,2-b]indole-3-carboxylate). Obtained the 6-F isomer (190.1 mg, 13%): HPLC: RT=0.91 min (Waters Acquity UPLC BEH C18 1.7 um 2.0×50 mm, MeOH/H$_2$O/0.1% TFA, 1 min gradient, wavelength=254 nm); MS (ES): m/z=323/325 $^{79}$Br/$^{81}$Br [M+1]$^+$; $^1$H NMR (500 MHz, DMSO-d$_6$) δ 9.07 (d, J=1.83 Hz, 1H), 8.37 (d, J=1.83 Hz, 1H), 8.03 (d, J=8.39 Hz, 1H), 7.52 (dd, J=5.95, 8.39 Hz, 1H), 3.95 (s, 3H).

The 8-F isomer (methyl 7-bromo-8-fluoro-5H-pyrido[3,2-b]indole-3-carboxylate) was also obtained (301.5 mg, 20%): $^1$H NMR showed this to be a mixture of primarily 8-F isomer along with small amounts of other biproducts. HPLC: RT=0.90 min (Waters Acquity UPLC BEH C18 1.7 um 2.0×50 mm, MeOH/H$_2$O/0.1% TFA, 1 min gradient, wavelength=254 nm); MS (ES): m/z=323/325 $^{79}$Br/$^{81}$Br [M+1]$^+$; $^1$H NMR (400 MHz, DMSO-d$_6$) δ=9.03 (d, J=2.0 Hz, 1H), 8.45 (d, J=2.0 Hz, 1H), 8.18 (d, J=8.6 Hz, 1H), 8.04 (d, J=5.7 Hz, 1H), 3.95 (s, 3H).

Step 2: (S)-Methyl 7-bromo-6-fluoro-5-(phenyl(tetrahydro-2H-pyran-4-yl)methyl)-5H-pyrido[3,2-b]indole-3-carboxylate To a cool (0° C.), stirred solution of methyl 7-bromo-6-fluoro-5H-pyrido[3,2-b]indole-3-carboxylate (94.3 mg, 0.292 mmol), (R)-phenyl(tetrahydro-2H-pyran-4-yl)methanol (113.4 mg, 0.590 mmol), and triphenylphosphine (152.7 mg, 0.582 mmol) in THF (6.0 mL) under N$_2$ was added DIAD (0.11 mL, 0.566 mmol) dropwise via syringe, stirred for 5 min, then removed from ice bath, and stirred overnight. The reaction mixture was concentrated in vacuo. The residue was purified by flash chromatography (Teledyne ISCO CombiFlash Rf, gradient of 0% to 100% using solvent A/B=CH$_2$Cl$_2$/EtOAc over 20 column volumes, RediSep SiO$_2$ 40 g, loaded as DCM solution). The still impure product was dissolved in EtOAc, washed with 1N HCl, water, brine, dried over sodium sulfate, filtered, and concentrated. The reaction mixture was dissolved in MeOH, and water was added until milky. The reaction mixture was heated until all dissolved and allowed to cool to room temperature overnight. The resulting solid was collected by filtration, washed with water and allowed to air dry. The product, (S)-methyl 7-bromo-6-fluoro-5-(phenyl(tetrahydro-2H-pyran-4-yl)methyl)-5H-pyrido[3,2-b]indole-3-carboxylate (97.2 mg, 67%) was obtained as a cream solid: HPLC: RT=1.18 min (Waters Acquity UPLC BEH C18 1.7 um 2.0×50 mm, CH$_3$CN/H$_2$O/0.05% TFA, 1 min gradient, wavelength=254 nm); MS (ES): m/z=497/499 $^{79}$Br/$^{81}$Br [M+1]$^+$.

Step 3: Methyl 7-(1,4-dimethyl-1H-1,2,3-triazol-5-yl)-6-fluoro-5-((S)-phenyl(tetrahydro-2H-pyran-4-yl)methyl)-5H-pyrido[3,2-b]indole-3-carboxylate To a 40 mL vial equipped with a stir bar under ambient atmosphere, was added (S)-methyl 7-bromo-6-fluoro-5-(phenyl(tetrahydro-2H-pyran-4-yl)methyl)-5H-pyrido[3,2-b]indole-3-carboxylate (63.5 mg, 0.128 mmol), 1,4-dimethyl-5-(tributylstannyl)-1H-1,2,3-triazole (70.4 mg, 0.182 mmol) in DMF (2.7 mL). Through the stirring solution was bubbled N$_2$ for 5 min, then while bubbling continued Pd(Ph$_3$P)$_4$ (17.4 mg, 0.015 mmol) and copper(I) iodide (13.4 mg, 0.070 mmol) were added, the vial capped, then heated to 95° C. with stirring overnight. The black reaction mixture was cooled to room temperature. To the reaction was added additional organotin (98.2 mg) in DMF (1.0 mL) and Et$_3$N (0.05 mL), N$_2$ was bubbled through the mixture for 5 min, then additional CuI (14.1 mg) and Pd(PPh$_3$)$_4$ (23.0 mg) were added, capped, and reheated to 95° C. with stirring overnight. The reaction was cooled to room temperature, diluted with EtOAc, filtered through Celite, washed with EtOAc and concentrated in vacuo. The residue was purified by flash chromatography (Teledyne ISCO CombiFlash Rf, gradient of 0% to 20% using solvent A/B=CH$_2$Cl$_2$/MeOH over 30 column volumes, RediSep SiO$_2$ 24 g, loaded as DCM solution). The product, methyl 7-(1,4-dimethyl-1H-1,2,3-triazol-5-yl)-6-fluoro-5-((S)-phenyl(tetrahydro-2H-pyran-4-yl)methyl)-5H-pyrido[3,2-b]indole-3-carboxylate (109.2 mg, >100%; O=PPh$_3$ contamination) was obtained as a pale yellow film: HPLC: RT=0.97 min (Waters Acquity UPLC BEH C18 1.7 um 2.0×50 mm, CH$_3$CN/H$_2$O/0.05% TFA, 1 min gradient, wavelength=254 nm); MS (ES): m/z=514 [M+1]$^+$.

Step 4: 2-[7-(Dimethyl-1H-1,2,3-triazol-5-yl)-6-fluoro-5-[(S)-oxan-4-yl(phenyl)methyl]-5H-pyrido[3,2-b]indol-3-yl]propan-2-ol To a cold (−78° C.), stirred solution of methyl 7-(1,4-dimethyl-1H-1,2,3-triazol-5-yl)-6-fluoro-5-((S)-phenyl(tetrahydro-2H-pyran-4-yl)methyl)-5H-pyrido[3,2-b]indole-3-carboxylate (65.7 mg, 0.128 mmol) in tetrahydrofuran (2560 µl) under N$_2$ was added methylmagnesium bromide (3M in Et$_2$O, 853 µl, 2.56 mmol), stirred for 10 min, then warmed in an ice bath and stirred an additional 20 min. The reaction was quenched with 4 mL sat. NH$_4$Cl, diluted with EtOAc, the organic phase was separated and concentrated. The residue was dissolved in DMF (2 mL), filtered through a 4 um membrane filter, and purified via preparative LC/MS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 0-100% B over 20 minutes, then a 0-minute hold at 100% B; Flow: 20 mL/min. Fractions containing the desired product were combined and dried via centrifugal evaporation. Obtained the product (7.2 mg, 11%): HPLC: RT=1.54 min (Waters Acquity UPLC BEH C18, 2.1×50 mm, 1.7-µm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm); MS (ES): m/z=514 [M+1]$^+$; $^1$H NMR (500 MHz, DMSO-d$_6$) δ 8.61 (br s, 1H), 8.17 (d, J=8.08 Hz, 1H), 7.55 (br s, 1H), 7.14-7.38 (m, 4H), 5.84 (br d, J=10.77 Hz, 1H), 3.85 (br d, J=10.10 Hz, 1H), 3.71 (br d, J=10.43 Hz, 1H), 3.46 (br t, J=11.28 Hz, 1H), 3.27 (br s, 1H), 2.54 (s, 3H), 2.21 (br s, 2H), 1.75 (br s, 1H), 1.51 (br s, 6H), 1.28 (br d, J=9.42 Hz, 1H), 1.00 (br d, J=11.78 Hz, 1H).

Example 21

2-[7-(Dimethyl-1H-1,2,3-triazol-5-yl)-8-fluoro-5-[(S)-(2-fluorophenyl)(oxan-4-yl)methyl]-5H-pyrido[3,2-b]indol-3-yl]propan-2-ol

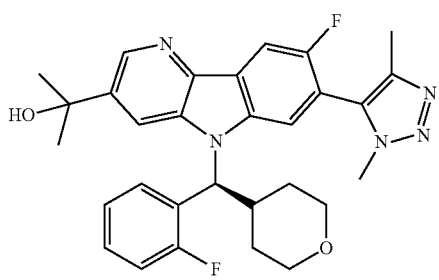 [SMILES: Cc1nnn(C)c1-c1cc2c(cc1F)c1ncc(C(C)(C)O)cc1n2[C@H](c1ccccc1F)C1CCOCC1]

Route 1

Step 1: (S)-Methyl 7-bromo-8-fluoro-5-((2-fluorophenyl)(tetrahydro-2H-pyran-4-yl)methyl)-5H-pyrido[3,2-b]indole-3-carboxylate To a cool (0° C.), stirred solution of methyl 7-bromo-8-fluoro-5H-pyrido[3,2-b]indole-3-carboxylate (101.4 mg, 0.314 mmol), (R)-(2-fluorophenyl)(tetrahydro-2H-pyran-4-yl)methanol (141.3 mg, 0.672 mmol), and triphenylphosphine (173.5 mg, 0.661 mmol) in THF (6.2 mL) under $N_2$ was added DIAD (0.12 mL, 0.617 mmol) dropwise via syringe, stirred for 5 min, then removed from ice bath and stirred for 3 h. The reaction mixture was concentrated in vacuo. The residue was dissolved in DCM, washed with water, brine, dried over magnesium sulfate, filtered, and concentrated. The residue was purified by flash chromatography (Teledyne ISCO CombiFlash Rf, gradient of 0% to 100% using solvent A/B=hexanes/EtOAc over 20 column volumes, RediSep $SiO_2$ 24 g, loaded as DCM solution). The product, (S)-methyl 7-bromo-8-fluoro-5-((2-fluorophenyl)(tetrahydro-2H-pyran-4-yl)methyl)-5H-pyrido[3,2-b]indole-3-carboxylate (83.0 mg, 51%) was obtained as a pale yellow solid: HPLC: RT=1.13 min (Waters Acquity UPLC BEH C18 1.7 um 2.0×50 mm, $CH_3CN/H_2O$/0.05% TFA, 1 min gradient, wavelength=254 nm); MS (ES): m/z=515/517 $^{79}Br/^{81}Br$ [M+1]$^+$.

Step 2: Methyl 7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indole-3-carboxylate To a 25 mL RB flask equipped with a stir bar under ambient atmosphere, was added (S)-methyl 7-bromo-8-fluoro-5-((2-fluorophenyl)(tetrahydro-2H-pyran-4-yl)methyl)-5H-pyrido[3,2-b]indole-3-carboxylate (66.1 mg, 0.128 mmol), 1,4-dimethyl-5-(tributylstannyl)-1H-1,2,3-triazole (104.5 mg, 0.271 mmol) in DMF (2.6 mL). Through the stirring solution was bubbled $N_2$ for 5 min, then while bubbling continued Pd(Ph$_3$P)$_4$ (17.9 mg, 0.015 mmol) and copper(I) iodide (19.6 mg, 0.103 mmol) were added, the vial capped, then heated to 95° C. with stirring overnight. The reaction was cooled to room temperature, diluted with EtOAc, filtered through Celite, washed with EtOAc and concentrated in vacuo. The residue was purified by flash chromatography (Teledyne ISCO CombiFlash Rf, gradient of 0% to 100% using solvent A/B=$CH_2Cl_2$/acetone over 20 column volumes, then changed to $CH_2Cl_2$: MeOH, added a gradient to 20% MeOH, then 60% then 100%, RediSep $SiO_2$ 24 g, loaded as DCM solution). The product, methyl 7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indole-3-carboxylate (19.9 mg, 29%) was obtained as a cream solid: HPLC: RT=0.97 min (Waters Acquity UPLC BEH C18 1.7 um 2.0×50 mm, $CH_3CN/H_2O$/0.05% TFA, 1 min gradient, wavelength=254 nm); MS (ES): m/z=532 [M+1]$^+$.

Step 3: Methyl 7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indole-3-carboxylate To a cold (−78° C.), stirred solution of methyl 7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indole-3-carboxylate (19.9 mg, 0.037 mmol) in tetrahydrofuran (1.0 mL) under $N_2$ was added methylmagnesium bromide (3.0M in $Et_2O$, 0.250 mL, 0.749 mmol), stirred for 15 min, then warmed to 0° C. and stirred an additional 15 min. The reaction mixture was quenched with 4 mL sat. $NH_4Cl$, warmed to room temperature, diluted with EtOAc, the organic phase was separated and concentrated. The residue was dissolved in 2 mL DMF, filtered through a 4µ membrane filter, then purified via preparative LC/MS with the following conditions: Column: Waters XBridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 10-100% B over 20 minutes, then a 5-minute hold at 100% B; Flow: 20 mL/min. Fractions containing the desired product were combined and dried via centrifugal evaporation. Obtained the product (5.1 mg, 25%): HPLC: RT=1.53 min (Waters Acquity UPLC BEH C18, 2.1×50 mm, 1.7-µm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm); MS (ES): m/z=532 [M+1]$^+$.

Route 2

Step 1: (5-(4-Bromo-2-fluorophenyl)-1,4-dimethyl-1H-1,2,3-triazole

A 100 mL round-bottomed flask was charged with 4-bromo-2-fluoro-1-iodobenzene (765.3 mg, 2.54 mmol), 1,4-dimethyl-5-(tributylstannyl)-1H-1,2,3-triazole (1.08 g, 2.80 mmol), and triethylamine (0.71 mL, 5.09 mmol) in DMF (25 mL), purged with $N_2$ by bubbling through solution over 5 min. To the mixture was added Pd(PPh$_3$)$_4$ (287.2 mg, 0.249 mmol) and copper(I) iodide (101.6 mg, 0.533 mmol), the flask was sealed with a septum then heated to 95° C. with stirring for 3.5 h. The reaction mixture was cooled to room temperature and then concentrated in vacuo. The residue was purified by flash chromatography (Teledyne ISCO CombiFlash Rf, gradient of 0% to 100% using solvent A/B=hexanes/EtOAc over 12 column volumes, RediSep $SiO_2$ 80 g, loaded as DCM solution). The product, 5-(4-bromo-2-fluorophenyl)-1,4-dimethyl-1H-1,2,3-triazole (316.4 mg, 46%) was obtained as a cream solid: HPLC:

RT=0.84 min (Waters Acquity UPLC BEH C18 1.7 um 2.0×50 mm, $CH_3CN/H_2O/0.05\%$ TFA, 1 min gradient, wavelength=254 nm); MS (ES): m/z=270/272 $^{79}Br/^{81}Br$ [M+1]$^+$; $^1H$ NMR (400 MHz, CDCl$_3$) δ 7.49-7.44 (m, 2H), 7.16 (dd, J=8.3 (H–H), 7.6 Hz (H–F), 1H), 3.92 (d, J=0.9 Hz, 3H), 2.29 (s, 3H).

Step 2: (4-(1,4-Dimethyl-1H-1,2,3-triazol-5-yl)-3-fluorophenyl)boronic acid

To a cold (−78° C.), stirred solution of 5-(4-bromo-2-fluorophenyl)-1,4-dimethyl-1H-1,2,3-triazole (583.7 mg, 2.16 mmol) in THF (22 mL) under $N_2$ was added n-BuLi (1.6M in hexane, 1.5 mL, 2.4 mmol), stirred for 20 min. To the reaction was added triisopropyl borate (0.62 mL, 2.67 mmol), stirred for 2 h, then allowed to warm to room temperature, and stirred for 2 h. The reaction was quenched with sat. $NH_4Cl$ and 1M HCl, diluted with EtOAc, the organic phase was separated, washed with sat. NaCl then dried over magnesium sulfate, filtered, and concentrated. The product, (4-(1,4-dimethyl-1H-1,2,3-triazol-5-yl)-3-fluorophenyl)boronic acid (460.8 mg, 91%) was obtained as a pale yellow gum: HPLC: RT=0.59 min (Waters Acquity UPLC BEH C18 1.7 um 2.0×50 mm, $CH_3CN/H_2O/0.05\%$ TFA, 1 min gradient, wavelength=254 nm); MS (ES): m/z=236 [M+1]$^+$.

Step 3: Methyl 6-(4-(1,4-dimethyl-1H-1,2,3-triazol-5-yl)-3-fluorophenyl)-5-nitronicotinate To a stirred solution of methyl 6-bromo-5-nitronicotinate (248.6 mg, 0.952 mmol), (4-(1,4-dimethyl-1H-1,2,3-triazol-5-yl)-3-fluorophenyl)boronic acid (260.6 mg, 1.11 mmol), and PdCl$_2$(dppf) (42.2 mg, 0.058 mmol) in THF (9.3 mL) was added tripotassium phosphate (3M in $H_2O$, 0.93 mL, 2.79 mmol), purged with $N_2$ (vacuum/$N_2$×3) and the reaction was heated at 75° C. with stirring for 2 h. The reaction was cooled to room temperature, diluted with EtOAc, dried over magnesium sulfate, filtered, and concentrated. The residue was purified by flash chromatography (Teledyne ISCO CombiFlash Rf, gradient of 0% to 60% using solvent A/B=hexanes/EtOAc over 15 column volumes, RediSep SiO$_2$ 40 g). Obtained the product (methyl 6-(4-(1,4-dimethyl-1H-1,2,3-triazol-5-yl)-3-fluorophenyl)-5-nitronicotinate (130 mg, 37%)): HPLC: RT=0.83 min (Waters Acquity UPLC BEH C18 1.7 um 2.0×50 mm, $CH_3CN/H_2O/0.05\%$ TFA, 1 min gradient, wavelength=254 nm); MS (ES): m/z=372 [M+1]$^+$; $^1H$ NMR (400 MHz, CDCl$_3$) δ 9.45 (d, J=1.83 Hz, 1H), 8.80 (d, J=1.83 Hz, 1H), 7.57 (dd, J=1.59, 10.03 Hz, 1H), 7.50 (dd, J=1.71, 7.95 Hz, 1H), 7.37-7.44 (m, 1H), 4.07 (s, 3H), 3.99 (d, J=1.10 Hz, 3H), 2.34 (s, 3H).

Step 4 Methyl 7-(1,4-dimethyl-1H-1,2,3-triazol-5-yl)-6-fluoro-5H-pyrido[3,2-b]indole-3-carboxylate and methyl 7-(1,4-dimethyl-1H-1,2,3-triazol-5-yl)-8-fluoro-5H-pyrido[3,2-b]indole-3-carboxylate A 20 mL vial was charged with methyl 6-(4-(1,4-dimethyl-1H-1,2,3-triazol-5-yl)-3-fluorophenyl)-5-nitronicotinate (130 mg, 0.350 mmol) and DPPE (165.4 mg, 0.415 mmol) in 2,3-dichlorobenzene (3.5 mL) and the contents were heated at 170° C. with stirring for 15 min, then cooled to room temperature and concentrated. The residue was dissolved in THF, SiO$_2$ (2 g) was added, concentrated then dried under vacuum. The material was then purified by flash chromatography (Teledyne ISCO CombiFlash Rf, gradient of 0% to 20% using solvent A/B=$CH_2Cl_2$/MeOH over 20 column volumes, RediSep SiO$_2$ 40 g). A 1:1 mixture (by LCMS) of isomers (218.5 mg) was obtained as a tan solid: HPLC: RT=0.73/0.74 min (Waters Acquity UPLC BEH C18 1.7 um 2.0×50 mm, $CH_3CN/H_2O/0.05\%$ TFA, 1 min gradient, wavelength=254 nm); MS (ES): m/z=372 [M+1]$^+$.

Step 5 Methyl 7-(1,4-dimethyl-1H-1,2,3-triazol-5-yl)-6-fluoro-5-((S)-(2-fluorophenyl)(tetrahydro-2H-pyran-4-yl)methyl)-5H-pyrido[3,2-b]indole-3-carboxylate compound with methyl 7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indole-3-carboxylate To a stirred solution of the 1:1 mixture of 6-F and 8-F-isomers (119 mg, 0.350 mmol) and (R)-(2-fluorophenyl)(tetrahydro-2H-pyran-4-yl)methyl methanesulfonate (148.9 mg, 0.516 mmol) in DMF (3.5 mL) under $N_2$ was added $Cs_2CO_3$ (231.9 mg, 0.712 mmol), and the reaction was heated at 60° C. with stirring overnight. After cooling to room temperature, additional mesylate (176 mg) was added as a solution in DMF (1 mL), then reheated for an additional 48 h. The mixture was concentrated. The residue was dissolved in EtOAc, washed with $H_2O$, sat. NaCl then dried over magnesium sulfate, filtered, and concentrated in vacuo. The material was purified by SFC (Chiral OJ-H 25×3 cm ID, 5 μm on a Berger SFC MGII instrument; flow rate of 85.0 mL/min; Mobile Phase: 85/15 $CO_2$/MeOH; detector wavelength: 220 nm; sample prep and inj. volume: 3000 μl of 51 mg dissolved in 7 mL MeOH w/ACN). Obtained methyl 7-(1,4-dimethyl-1H-1,2,3-triazol-5-yl)-6-fluoro-5-((S)-(2-fluorophenyl)(tetrahydro-2H-pyran-4-yl)methyl)-5H-pyrido[3,2-b]indole-3-carboxylate (12.6 mg, 6.8%): HPLC: RT=0.95 min (Waters Acquity UPLC BEH C18 1.7 um 2.0×50 mm, $CH_3CN/H_2O/0.05\%$ TFA, 1 min gradient, wavelength=254 nm); MS (ES): m/z=532 [M+1]$^+$; $^1H$ NMR (500 MHz, DMSO-d$_6$, 100° C.) δ 9.08 (d, J=1.68 Hz, 1H), 8.69 (br s, 1H), 8.26 (d, J=8.09 Hz, 1H), 7.97-8.04 (m, 1H), 7.38 (dd, J=5.80, 7.93 Hz, 2H), 7.30-7.35 (m, 1H), 7.08 (br dd, J=8.77, 10.45 Hz, 1H), 6.23 (br dd, J=3.43, 10.91 Hz, 1H), 3.98 (s, 4H), 3.86-3.96 (m, 5H), 3.75 (br dd, J=2.29, 11.60 Hz, 1H), 3.50-3.59 (m, 1H), 3.25-3.36 (m, 2H), 2.22 (s, 3H), 1.86 (br d, J=12.66 Hz, 1H), 1.54 (br d, J=10.83 Hz, 1H), 1.33-1.45 (m, 1H), 1.02 (br d, J=13.28 Hz, 1H).

Also obtained was methyl 7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indole-3-carboxylate (20.5 mg, 11%): $^1H$ NMR (500 MHz, DMSO-d$_6$, 100° C.) δ 9.06 (d, J=1.10 Hz, 1H), 8.23 (d, J=9.46 Hz, 2H), 7.26-7.44 (m, 2H), 7.03-7.17 (m, 1H), 6.17 (d, J=11.44 Hz, 1H), 3.81-4.02 (m, 7H), 3.69 (br d, J=8.80 Hz, 1H), 3.33-3.54 (m, 2H), 3.20 (br t, J=11.00 Hz, 1H), 2.18 (br s, 3H), 1.59-1.78 (m, 2H), 1.28-1.46 (m, 1H), 0.76 (br d, J=11.88 Hz, 1H).

Step 6: 2-[7-(Dimethyl-1H-1,2,3-triazol-5-yl)-8-fluoro-5-[(S)-(2-fluorophenyl)(oxan-4-yl)methyl]-5H-pyrido[3,2-b]indol-3-yl]propan-2-ol To a cold (−78° C.), stirred solution of methyl 7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indole-3-carboxylate (20.5 mg, 0.039 mmol) in tetrahydrofuran (1.0 mL) under $N_2$ was added methylmagnesium bromide (3.0M in Et$_2$O, 0.257 mL, 0.771 mmol), stirred for 25 min, warmed to 0° C. and stirred an additional 25 min. The reaction was quenched with 4 mL sat. $NH_4Cl$, warmed to room temperature, diluted with EtOAc, the organic phase was separated, dried over magnesium sulfate, filtered, and concentrated. The residue was purified by flash chromatography (Teledyne ISCO CombiFlash Rf, gradient of 0% to 100% using solvent A/B=CH$_2$Cl$_2$/acetone over 50 column volumes, RediSep SiO$_2$ 4 g, loaded as DCM solution). The product, 2-(7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indol-3-yl)propan-2-ol (17.2 mg, 81%) was obtained as a colorless solid: HPLC: RT=0.78 min (Waters Acquity UPLC BEH C18 1.7 um 2.0×50 mm, CH$_3$CN/H$_2$O/0.05% TFA, 1 min gradient, wavelength=254 nm); MS (ES): m/z=532 [M+1]$^+$; $^1$H NMR (500 MHz, DMSO-d$_6$) δ 8.69 (d, J=1.8 Hz, 1H), 8.25 (s, 1H), 8.11-8.07 (m, 1H), 8.06 (d, J=9.5 Hz, 2H), 7.98 (d, J=5.5 Hz, 1H), 7.39-7.31 (m, 1H), 7.30-7.25 (m, 1H), 7.10 (ddd, J=10.9, 8.1, 1.1 Hz, 1H), 5.96 (d, J=11.4 Hz, 1H), 5.08 (s, 1H), 3.90 (s, 4H), 3.74 (dd, J=11.4, 2.4 Hz, 1H), 3.51 (td, J=11.6, 2.2 Hz, 1H), 3.44-3.30 (m, 1H), 3.26 (td, J=11.7, 2.1 Hz, 1H), 2.21 (s, 3H), 1.73 (d, J=12.7 Hz, 1H), 1.60 (d, J=2.9 Hz, 7H), 1.43-1.31 (m, 1H), 0.94 (d, J=13.1 Hz, 1H).

Example 22

2-{8-Fluoro-5-[(S)-(2-fluorophenyl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol

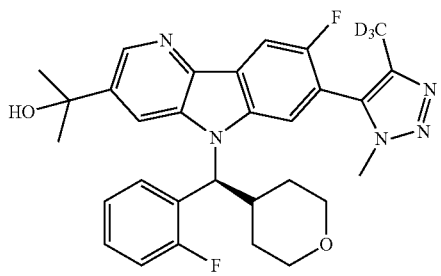 [SMILES: [2H]C([2H])([2H])c1nnn(C)c1-c1cc2c(cc1F)c1ncc(C(C)(C)O)cc1n2[C@H](c1ccccc1F)C1CCOCC1]

Step 1: (S)-3-Bromo-7-chloro-8-fluoro-5-((2-fluorophenyl)(tetrahydro-2H-pyran-4-yl)methyl)-5H-pyrido[3,2-b]indole To a stirred solution of 3-bromo-7-chloro-8-fluoro-5H-pyrido[3,2-b]indole (1.00 g, 3.34 mmol) and (R)-(2-fluorophenyl)(tetrahydro-2H-pyran-4-yl)methyl methanesulfonate (1.37 g, 4.75 mmol) in DMF (13.35 mL) under N$_2$ was added Cs$_2$CO$_3$ (3.25 g, 9.97 mmol), and the reaction was heated at 60° C. with stirring for 48 h. Cooled to room temperature, and concentrated in vacuo. The residue was dissolved in EtOAc, washed with H$_2$O, 10% LiCl (×3), sat. NaCl then dried over magnesium sulfate, filtered, and concentrated in vacuo. The residue was purified by flash chromatography (Teledyne ISCO CombiFlash Rf, gradient of 0% to 100% using solvent A/B=hexanes/EtOAc over 12 column volumes, RediSep SiO$_2$ 80 g, loaded as DCM solution). The product, (S)-3-bromo-7-chloro-8-fluoro-5-((2-fluorophenyl)(tetrahydro-2H-pyran-4-yl)methyl)-5H-pyrido[3,2-b]indole (1.20 g, 73%) was obtained as a colorless solid: HPLC: RT=1.18 min (Waters Acquity UPLC BEH C18 1.7 um 2.0×50 mm, CH$_3$CN/H$_2$O/0.05% TFA, 1 min gradient, wavelength=254 nm); MS (ES): m/z=491 [M+1]$^+$.

Step 2: (S)-1-(7-Chloro-8-fluoro-5-((2-fluorophenyl)(tetrahydro-2H-pyran-4-yl)methyl)-5H-pyrido[3,2-b]indol-3-yl)ethanone To a 40 mL I-Chem vial equipped with a stir bar under ambient atmosphere, was added (S)-3-bromo-7-chloro-8-fluoro-5-((2-fluorophenyl)(tetrahydro-2H-pyran-4-yl)methyl)-5H-pyrido[3,2-b]indole (199.2 mg, 0.405 mmol), tributyl(1-ethoxyvinyl)stannane (222.8 mg, 0.617 mmol), Pd(PPh$_3$)$_4$ (49.7 mg, 0.043 mmol) and copper(I) iodide (21.7 mg, 0.114 mmol). The vial was sealed with a PTFE-lined septum screw-cap, DMF (8.1 mL) was added, then the atmosphere purged with N$_2$ (vacuum/N$_2$×4). Et$_3$N (0.11 mL, 0.789 mmol) was added, and the reaction was then heated to 95° C. with stirring overnight. The reaction was cooled to room temperature. The reaction was diluted with EtOAc (150 mL), washed with 10% LiCl (3×50 mL), sat. NaCl then dried over magnesium sulfate, filtered, and concentrated in vacuo. The residue above was dissolved in THF (20 mL), 3M HCl (10 mL) was added and stirred for 2.5 h. The reaction mixture was neutralized with 1.5M K$_2$HPO$_4$, diluted with EtOAc, the organic phase separated, washed with sat. NaCl then dried over magnesium sulfate, filtered, and concentrated in vacuo. The residue was purified by flash chromatography (Teledyne ISCO CombiFlash Rf, gradient of 0% to 100% using solvent A/B=hexanes/EtOAc over 12 column volumes, RediSep SiO$_2$ 40 g, loaded as DCM solution). The product, (S)-1-(7-chloro-8-fluoro-5-((2-fluorophenyl)(tetrahydro-2H-pyran-4-yl)methyl)-5H-pyrido[3,2-b]indol-3-yl)ethanone (112.9 mg, 61%) was obtained as a tan solid: HPLC: RT=1.06 min (Waters Acquity UPLC BEH C18 1.7 um 2.0×50 mm, CH$_3$CN/H$_2$O/0.05% TFA, 1 min gradient, wavelength=254 nm); MS (ES): m/z=455 [M+1]$^+$; $^1$H NMR (400 MHz, CDCl$_3$) 9.12 (d, J=1.8 Hz, 1H), 8.54 (d, J=1.3 Hz, 1H), 8.12 (d, J=8.4 Hz, 1H), 7.79-7.75 (m, 1H), 7.74 (d, J=5.5 Hz, 1H), 7.10-7.01 (m, 1H), 5.67 (d, J=11.4 Hz, 1H), 4.06 (dd, J=12.1, 2.4 Hz, 1H), 3.90-3.80 (m, 1H), 3.54 (td, J=11.8, 2.1 Hz, 1H), 3.35 (td, J=11.9, 2.0 Hz, 1H), 3.24-3.07 (m, 1H), 2.77 (s, 3H), 1.88 (d, J=14.5 Hz, 1H), 1.43-1.29 (m, 2H), 0.98 (d, J=14.3 Hz, 1H).

Step 3: 1-{8-Fluoro-5-[(S)-(2-fluorophenyl)(oxan-4-yl)methyl]-7-[4-($^2$H$_3$)methyl-1-methyl-1H-1,2,3-triazol-5-yl]-5H-pyrido[3,2-b]indol-3-yl}ethan-1-one To a 25 mL RB flask equipped with a stir bar under ambient atmosphere, was added (S)-1-(7-chloro-8-fluoro-5-((2-fluorophenyl)(tetrahydro-2H-pyran-4-yl)methyl)-5H-pyrido[3,2-b]indol-3-yl)ethanone (89.9 mg, 0.198 mmol), 1-methyl-4-($^2$H$_3$)methyl-5-tributylstannyl-1H-1,2,3-triazole (155.2 mg, 0.399 mmol), Pd$_2$(dba)$_3$ (18.4 mg, 0.020 mmol), and Cs$_2$CO$_3$ (146.9 mg, 0.451 mmol). The flask was sealed with a septum, dioxane (4.0 mL) and tricyclohexylphosphine (30% in toluene, 44.2 mg, 0.047 mmol) were added, then the atmosphere purged with N$_2$ (vacuum/N$_2$×4). The reaction was then heated to 115° C. with stirring overnight. The reaction was cooled to room temperature, diluted with EtOAc, filtered through a 4u membrane filter, concentrated. The residue was purified by flash chromatography (Teledyne ISCO CombiFlash Rf, gradient of 0% to 100% using solvent A/B=CH$_2$Cl$_2$/acetone over 20 column volumes, RediSep SiO$_2$ 40 g, loaded as DCM solution). The product (29.8 mg, 29%) was obtained as a yellow film: HPLC: RT=0.91 min (Waters Acquity UPLC BEH C18 1.7 um 2.0×50 mm, CH₃CN/H₂O/0.05% TFA, 1 min gradient, wavelength=254 nm); MS (ES): m/z=519 [M+1]⁺.

Step 4: 2-{8-Fluoro-5-[(S)-(2-fluorophenyl)(oxan-4-yl)methyl]-7-[4-(²H₃)methyl-1-methyl-1H-1,2,3-triazol-5-yl]-5H-pyrido[3,2-b]indol-3-yl}propan-2-ol To a cold (−78° C.), stirred solution of 1-{8-Fluoro-5-[(S)-(2-fluorophenyl)(oxan-4-yl)methyl]-7-[4-(²H₃)methyl-1-methyl-1H-1,2,3-triazol-5-yl]-5H-pyrido[3,2-b]indol-3-yl}ethan-1-one (29.8 mg, 0.057 mmol) in tetrahydrofuran (1.2 mL) under N₂ was added methylmagnesium bromide (0.19 mL, 0.570 mmol), stirred for 15 min, warmed to 0° C., and stirred an additional 30 min. NH₄Cl (5 mL) was added, warmed to room temperature, diluted with EtOAc, washed with sat. NaCl then dried over magnesium sulfate, filtered, and concentrated in vacuo. The residue was purified by flash chromatography (Teledyne ISCO CombiFlash Rf, gradient of 0% to 100% using solvent A/B=CH₂Cl₂/acetone over 50 column volumes, RediSep SiO₂ 4 g, loaded as DCM solution). Fractions containing product were collected and concentrated. The residue was repurified on ISCO (Teledyne ISCO CombiFlash Rf, gradient of 0% to 20% using solvent A/B=CH₂Cl₂/MeOH over 30 column volumes, RediSep SiO₂ 12 g, loaded as DCM solution). The product (12.6 mg, 38%) was obtained as a colorless solid: HPLC: RT=1.060 min (Waters Acquity UPLC BEH C18 1.7 um 2.0×50 mm, CH₃CN/H₂O/0.1% TFA, 1.5 min gradient, wavelength=254 nm); MS (ES): m/z=535 [M+1]⁺; ¹H NMR (500 MHz, DMSO-d₆) δ 8.68 (br s, 1H), 8.19 (br s, 1H), 8.12 (br d, J=9.42 Hz, 1H), 7.93 (s, 1H), 7.27-7.38 (m, 2H), 7.06-7.13 (m, 1H), 6.02 (br d, J=11.44 Hz, 1H), 3.88 (br d, J=8.75 Hz, 3H), 3.70 (br d, J=8.08 Hz, 1H), 3.16-3.27 (m, 1H), 2.54 (s, 6H), 1.71 (br d, J=11.78 Hz, 1H), 1.57 (br s, 7H), 1.27-1.41 (m, 1H), 1.19-1.27 (m, 1H), 0.79 (br d, J=12.12 Hz, 1H).

Examples 23 and 24

1-Cyclopropyl-1-[7-(dimethyl-1H-1,2,3-triazol-5-yl)-8-fluoro-5-[(S)-(2-fluorophenyl)(oxan-4-yl)methyl]-5H-pyrido[3,2-b]indol-3-yl]ethan-1-ol

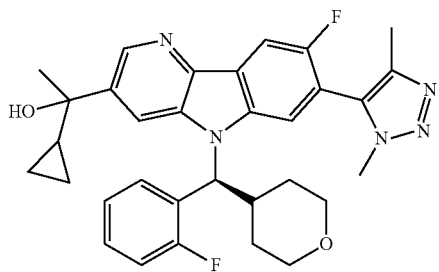

Diastereomer 1, Example 23

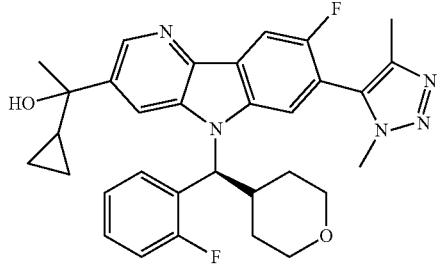

Diastereomer 2, Example 24

Step 1: 1-(7-(1,4-Dimethyl-1H-1,2,3-triazol-5-yl)-8-fluoro-5-((S)-(2-fluorophenyl)(tetrahydro-2H-pyran-4-yl)methyl)-5H-pyrido[3,2-b]indol-3-yl)ethanone To a 40 mL I-Chem vial equipped with a stir bar under ambient atmosphere, was added (S)-1-(7-chloro-8-fluoro-5-((2-fluorophenyl)(tetrahydro-2H-pyran-4-yl)methyl)-5H-pyrido[3,2-b]indol-3-yl)ethanone (174.8 mg, 0.384 mmol), 1,4-dimethyl-5-(tributylstannyl)-1H-1,2,3-triazole (305.1 mg, 0.790 mmol), Pd₂(dba)₃ (41.1 mg, 0.045 mmol), and Cs₂CO₃ (257.5 mg, 0.790 mmol). The vial was sealed with a PTFE-lined septum screw-cap, dioxane (3.8 mL) and tricyclohexylphosphine (30% in toluene, 75.7 mg, 0.081 mmol) were added, then the atmosphere purged with N₂ (vacuum/N₂×4). The reaction was then heated to 115° C. with stirring overnight. Cooled to room temperature, diluted with EtOAc, filtered through a 4u membrane filter, concentrated. The residue was purified by flash chromatography (Teledyne ISCO CombiFlash Rf, gradient of 0% to 100% using solvent A/B=CH₂Cl₂/EtOAc over 12 column volumes, RediSep SiO₂ 40 g, loaded as DCM solution). Fractions containing product were collected and concentrated. The residue was repurified by flash chromatography (Teledyne ISCO CombiFlash Rf, gradient of 0% to 100% using solvent A/B=CH₂Cl₂/acetone over 15 column volumes, RediSep SiO₂ 40 g, loaded as DCM solution). The product, 1-(7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indol-3-yl)ethanone (45.4 mg, 23%) was obtained as a tan solid: HPLC: RT=0.91 min (Waters Acquity UPLC BEH C18 1.7 um 2.0×50 mm, CH₃CN/H₂O/0.05% TFA, 1 min gradient, wavelength=254 nm); MS (ES): m/z=516 [M+1]⁺.

Step 2: 1-Cyclopropyl-1-[7-(dimethyl-1H-1,2,3-triazol-5-yl)-8-fluoro-5-[(S)-(2-fluorophenyl)(oxan-4-yl)methyl]-5H-pyrido[3,2-b]indol-3-yl]ethan-1-ol To a cold (−78° C.), stirred solution of 1-(7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indol-3-yl)ethanone (45.4 mg, 0.088 mmol) in tetrahydrofuran (1.8 mL) under N₂ was added cyclopropylmagnesium bromide (0.5M in THF, 1.8 mL, 0.90 mmol), stirred for 10 min, then warmed to 0° C., stirred an additional 35 min. To the reaction was added additional Grignard (1.8 mL) was added, stirred 40 min, then placed in −30° C. freezer overnight. The reaction was once again placed in a 0° C. bath, stirred for 10 min, at which time 4 mL sat. NH₄Cl was added, diluted with EtOAc, organic phase separated, washed with brine, dried over magnesium sulfate, filtered, and concentrated. The residue was dissolved in THF (2.0 mL), and cooled to −78° C. To the solution was added cyclopropylmagnesium bromide (0.5M in THF, 2.0 mL, 1.0 mmol), stirred for 15 min, placed in 0° C. bath, and stirred an additional 15 min. To the reaction was added sat. NH₄Cl, warmed to room temperature. The reaction was diluted with EtOAc, washed with sat. NaCl then dried over magnesium sulfate, filtered, and concentrated in vacuo. The residue was purified by flash chromatography (Teledyne ISCO CombiFlash Rf, gradient of 0% to 15% using solvent A/B=CH₂Cl₂/MeOH over 25 column volumes, RediSep SiO₂ 12 g, loaded as DCM solution). Fractions containing product were collected and concentrated. The residue was repurified by SFC (Column: OJ 25×3 cm ID, 5 μm on a Berger SFC MGII instrument; flow rate: 85.0 mL/min; mobile phase: 88/12 CO₂/(50/50

MeOH/ACN); detector wavelength: 314 nm; sample prep and inj. volume: 1500 μL of 35 mg dissolved in 5 mL MeOH/ACN).

Diastereomer 1 (1-cyclopropyl-1-(7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indol-3-yl)ethanol (3.0 mg, 6%)) was obtained as a colourless solid: HPLC: RT=1.140 min (Waters Acquity UPLC BEH C18 1.7 um 2.0×50 mm, CH$_3$CN/H$_2$O/0.1% TFA, 1.5 min gradient, wavelength=254 nm); MS (ES): m/z=558 [M+1]$^+$; $^1$H NMR (400 MHz, DMSO-d$_6$) δ 8.68 (s, 1H), 8.17 (br s, 2H), 8.09 (d, J=9.5 Hz, 1H), 7.40-7.25 (m, 2H), 7.15-7.06 (m, 1H), 6.03 (br d, J=11.2 Hz, 1H), 3.98-3.84 (m, 4H), 3.73 (br d, J=11.9 Hz, 1H), 3.48 (br t, J=11.2 Hz, 1H), 3.25-3.15 (m, 1H), 2.21 (br s, 3H), 1.78-1.68 (m, 1H), 1.58 (s, 3H), 1.37 (br d, J=12.3 Hz, 1H), 1.24 (s, 3H), 0.83 (br d, J=13.4 Hz, 2H), 0.56-0.33 (m, 3H), 0.23 (br s, 1H).

Diastereomer 2 (1-cyclopropyl-1-(7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indol-3-yl)ethanol (4.7 mg, 9%)) was obtained as a colourless solid: HPLC: RT=1.136 min (Waters Acquity UPLC BEH C18 1.7 um 2.0×50 mm, CH$_3$CN/H$_2$O/0.1% TFA, 1.5 min gradient, wavelength=254 nm); MS (ES): m/z=558 [M+1]$^+$; $^1$H NMR (400 MHz, DMSO-d$_6$) δ 8.70 (d, J=1.5 Hz, 1H), 8.28 (br s, 1H), 8.18 (br t, J=7.7 Hz, 1H), 8.09 (d, J=9.7 Hz, 1H), 7.41-7.25 (m, 2H), 7.16-7.06 (m, 1H), 6.02 (br d, J=11.7 Hz, 1H), 3.93 (br s, 2H), 3.87 (br s, 2H), 3.72 (br d, J=8.8 Hz, 1H), 3.49 (br t, J=10.9 Hz, 1H), 3.20 (br t, J=11.0 Hz, 1H), 2.21 (br s, 3H), 1.77-1.67 (m, 1H), 1.59 (br s, 4H), 1.41-1.26 (m, 3H), 1.24 (s, 1H), 0.90-0.74 (m, 2H), 0.56-0.47 (m, 1H), 0.46-0.32 (m, 2H), 0.32-0.21 (m, 1H).

Example 25

5-{8-Fluoro-5-[(S)-(2-fluorophenyl)(oxan-4-yl)methyl]-3-methanesulfonyl-5H-pyrido[3,2-b]indol-7-yl}-1,4-dimethyl-1H-1,2,3-triazole

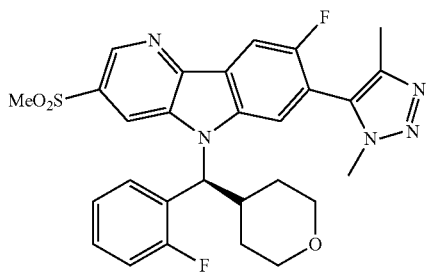 [SMILES: Cc1nnn(C)c1-c1cc2c(cc1F)c1ncc(S(C)(=O)=O)cc1n2[C@H](c1ccccc1F)C1CCOCC1]

Route 1

Step 1: 5-Bromo-2-(4-(1,4-dimethyl-1H-1,2,3-triazol-5-yl)-3-fluorophenyl)-3-nitropyridine To a stirred solution of 2,5-dibromo-3-nitropyridine (226 mg, 0.802 mmol), (4-(1,4-dimethyl-1H-1,2,3-triazol-5-yl)-3-fluorophenyl)boronic acid (282.6 mg, 1.20 mmol), and PdCl$_2$(dppf) (29.3 mg, 0.040 mmol) in THF (8.0 mL) was added tripotassium phosphate (3M in H$_2$O, 802 μl, 2.41 mmol), purged with N$_2$ (vacuum/N$_2$×3) and the reaction was heated at 75° C. with stirring for 1 h. The reaction was cooled to room temperature and concentrated. The residue was suspended in EtOAc, filtered through Celite, washed with EtOAc, concentrated. The residue was purified by flash chromatography (Teledyne ISCO CombiFlash Rf, gradient of 0% to 100% using solvent A/B=CH$_2$Cl$_2$/EtOAc over 15 column volumes, RediSep SiO$_2$ 40 g, loaded as DCM solution). Obtained the product (190 mg, 61%): HPLC: RT=0.91 min (Waters Acquity UPLC BEH C18 1.7 um 2.0×50 mm, CH$_3$CN/H$_2$O/0.1% TFA, 1.5 min gradient, wavelength=254 nm); MS (ES): m/z=392 [M+1]$^+$.

Step 2: 3-Bromo-7-(1,4-dimethyl-1H-1,2,3-triazol-5-yl)-6-fluoro-5H-pyrido[3,2-b]indole compound and 3-bromo-7-(1,4-dimethyl-1H-1,2,3-triazol-5-yl)-8-fluoro-5H-pyrido[3,2-b]indole A 50 mL round-bottomed flask was charged with 5-bromo-2-(4-(1,4-dimethyl-1H-1,2,3-triazol-5-yl)-3-fluorophenyl)-3-nitropyridine (190.7 mg, 0.486 mmol) and 1,2-bis(diphenylphosphino)ethane (241.9 mg, 0.607 mmol) in 1,2-dichlorobenzene (2.0 mL), then heated at 170° C. with stirring for 25 min. Cooled to room temperature, applied directly to an ISCO column and was purified by flash chromatography (Teledyne ISCO CombiFlash Rf, gradient of 0% to 100% using solvent A/B=CH$_2$Cl$_2$/EtOAc over 15 column volumes, RediSep SiO$_2$ 40 g). Obtained the 6-F isomer (3-bromo-7-(1,4-dimethyl-1H-1,2,3-triazol-5-yl)-6-fluoro-5H-pyrido[3,2-b]indole (45.7 mg, 26%): HPLC: RT=0.83 min (Waters Acquity UPLC BEH C18 1.7 um 2.0×50 mm, CH$_3$CN/H$_2$O/0.05% TFA, 1 min gradient, wavelength=254 nm); MS (ES): m/z=360/362 $^{79}$Br/$^{81}$Br [M+1]$^+$; $^1$H NMR (400 MHz, DMSO-d$_6$) δ 8.64 (d, J=2.0 Hz, 1H), 8.18 (d, J=2.0 Hz, 1H), 8.15 (d, J=8.1 Hz, 1H), 3.94 (s, 3H), 2.23 (s, 3H).

Also obtained the 8-F isomer (3-bromo-7-(1,4-dimethyl-1H-1,2,3-triazol-5-yl)-8-fluoro-5H-pyrido[3,2-b]indole (25.2 mg, 14%)): HPLC: RT=0.85 min (Waters Acquity UPLC BEH C18 1.7 um 2.0×50 mm, CH$_3$CN/H$_2$O/0.05% TFA, 1 min gradient, wavelength=254 nm); MS (ES): m/z=360/362 $^{79}$Br/$^{81}$Br [M+1]$^+$; $^1$H NMR (400 MHz, DMSO-d$_6$) δ 8.59 (d, J=2.0 Hz, 1H), 8.24 (d, J=2.2 Hz, 1H), 8.15 (d, J=9.7 Hz, 1H), 7.72 (d, J=5.9 Hz, 1H), 3.92 (s, 3H), 2.22 (s, 3H).

Step 3: 3-Bromo-7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indole To a cool (0° C.), stirred solution of 3-bromo-7-(1,4-dimethyl-1H-1,2,3-triazol-5-yl)-8-fluoro-5H-pyrido[3,2-b]indole (25.2 mg, 0.070 mmol), (R)-(2-fluorophenyl)(tetrahydro-2H-pyran-4-yl)methanol (32.6 mg, 0.155 mmol), and triphenylphosphine (39.3 mg, 0.150 mmol) in THF (1.4 mL) under N$_2$ was added DIAD (0.03 mL, 0.154 mmol) dropwise via syringe, stirred for 5 min, then removed from ice bath and stirred for an additional 2 h. Concentrated in vacuo. The residue was purified by flash chromatography (Teledyne ISCO CombiFlash Rf, gradient of 0% to 100% using solvent A/B=CH$_2$Cl$_2$/EtOAc over 30 column volumes, RediSep SiO$_2$ 12 g, loaded as DCM solution). Obtained the product (3-bromo-7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indole (24.3 mg, 63%)): HPLC: RT=1.07 min (Waters Acquity UPLC BEH C18 1.7 um 2.0×50 mm, CH$_3$CN/H$_2$O/0.05% TFA, 1 min gradient, wavelength=254 nm); MS (ES): m/z=552/554 $^{79}$Br/$^{81}$Br [M+1]$^+$.

Step 4: 5-{8-Fluoro-5-[(S)-(2-fluorophenyl)(oxan-4-yl)methyl]-3-methanesulfonyl-5H-pyrido[3,2-b]indol-7-yl}-1,4-dimethyl-1H-1,2,3-triazole A vial, fitted with a Teflon coated septum, containing 3-bromo-7-(1,4-dimethyl-1H-1,2,3-triazol-5-yl)-8-fluoro-5-((S)-(2-fluorophenyl)(tetrahydro-2H-pyran-4-yl)methyl)-5H-pyrido[3,2-b]indole (24.3 mg, 0.044 mmol), sodium methanesulfinate (19.2 mg, 0.188 mmol), copper(I) iodide (6.8 mg, 0.036 mmol), L-proline (5.1 mg, 0.044 mmol), and cesium carbonate (8.9 mg, 0.027 mmol) in DMSO (1.5 mL) was vacuum purged with nitrogen (3×), wrapped in foil to protect from light, and warmed to 100° C. for 7 h. Cooled to room temperature, AcOH (0.1 mL) was added, filtered through a 4μ membrane filter, and purified via preparative LC/MS with the following conditions: Column: Waters XBridge C18, 19×250 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 23-63% B over 25 minutes, then a 5-minute hold at 100% B; Flow: 20 mL/min. Fractions containing the desired product were combined and dried via centrifugal evaporation. Obtained the product (4.8 mg, 19%): HPLC: RT=1.56 min (Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm); MS (ES): m/z=552 [M+1]$^+$; $^1$H NMR (500 MHz, DMSO-d$_6$) δ 9.00 (s, 1H), 8.29 (d, J=9.42 Hz, 1H), 8.24 (br s, 1H), 7.27-7.41 (m, 2H), 7.10 (br t, J=9.42 Hz, 1H), 6.17 (br d, J=11.44 Hz, 1H), 3.88 (s, 3H), 3.70 (br d, J=8.41 Hz, 1H), 3.43 (br s, 1H), 3.21 (br t, J=11.44 Hz, 1H), 2.54 (s, 2H), 2.06-2.26 (m, 2H), 1.68-1.76 (m, 1H), 1.63 (br d, J=11.11 Hz, 1H), 1.39 (br d, J=9.42 Hz, 1H), 0.77 (br d, J=12.12 Hz, 1H).

Route 2

Step 1: (S)-7-Chloro-8-fluoro-5-((2-fluorophenyl)(tetrahydro-2H-pyran-4-yl)methyl)-3-(methylsulfonyl)-5H-pyrido[3,2-b]indole To a 40 mL vial equipped with a stir bar under ambient atmosphere, was added (S)-3-bromo-7-chloro-8-fluoro-5-((2-fluorophenyl)(tetrahydro-2H-pyran-4-yl)methyl)-5H-pyrido[3,2-b]indole (200.2 mg, 0.407 mmol), sodium methanesulfinate (63.8 mg, 0.625 mmol), copper(I) iodide (56.1 mg, 0.295 mmol), L-proline (54.5 mg, 0.473 mmol), and Cs$_2$CO$_3$ (96.5 mg, 0.296 mmol). The vial was sealed with a septum, DMSO (4.1 mL) was added, then the atmosphere purged with N$_2$ (vacuum/N$_2$×4). The reaction was then heated to 100° C. with stirring for 3 h. Cooled to room temperature. The reaction was diluted with Et$_2$O (100 mL), washed with H$_2$O (2×50 mL), sat. NaCl. The aqueous was extracted with EtOAc, combined with Et$_2$O phase, then dried over magnesium sulfate, filtered, and concentrated in vacuo. The residue was purified by flash chromatography (Teledyne ISCO CombiFlash Rf, gradient of 0% to 100% using solvent A/B=hexanes/EtOAc over 15 column volumes, RediSep SiO$_2$ 40 g, loaded as DCM solution). The product, (S)-7-chloro-8-fluoro-5-((2-fluorophenyl)(tetrahydro-2H-pyran-4-yl)methyl)-3-(methylsulfonyl)-5H-pyrido[3,2-b]indole (172.9 mg, 87%) was obtained as a cream solid: HPLC: RT=1.03 min (Waters Acquity UPLC BEH C18 1.7 um 2.0×50 mm, CH$_3$CN/H$_2$O/0.05% TFA, 1 min gradient, wavelength=254 nm); MS (ES): m/z=491/493 $^{35}$Cl/$^{37}$Cl [M+1]$^+$.

Step 2: 5-{8-Fluoro-5-[(S)-(2-fluorophenyl)(oxan-4-yl)methyl]-3-methanesulfonyl-5H-pyrido[3,2-b]indol-7-yl}-1,4-dimethyl-1H-1,2,3-triazole To a 40 mL I-Chem vial equipped with a stir bar under ambient atmosphere, was added (S)-7-chloro-8-fluoro-5-((2-fluorophenyl)(tetrahydro-2H-pyran-4-yl)methyl)-3-(methylsulfonyl)-5H-pyrido[3,2-b]indole (58.9 mg, 0.120 mmol), 1,4-dimethyl-5-(tributylstannyl)-1H-1,2,3-triazole (98.1 mg, 0.254 mmol), Pd$_2$(dba)$_3$ (11.2 mg, 0.012 mmol), and Cs$_2$CO$_3$ (80.0 mg, 0.246 mmol). The vial was sealed with a PTFE-lined septum screw-cap, dioxane (2.4 mL) and tricyclohexylphosphine (30% in toluene, 26 mg, 0.028 mmol) were added, then the atmosphere purged with N$_2$ (vacuum/N$_2$×4). The reaction was then heated to 115° C. with stirring overnight. Cooled to room temperature, diluted with EtOAc, filtered through a 4 μm membrane filter, concentrated. The residue was purified by flash chromatography (Teledyne ISCO CombiFlash Rf, gradient of 0% to 100% using solvent A/B=CH$_2$Cl$_2$/acetone over 30 column volumes, RediSep SiO$_2$ 24 g, loaded as DCM solution). Fractions containing product were collected and concentrated. The residue was repurified by flash chromatography (Teledyne ISCO CombiFlash Rf, gradient of 0% to 20% using solvent A/B=CH$_2$Cl$_2$/MeOH over 30 column volumes, RediSep SiO$_2$ 12 g, loaded as DCM solution). Fractions containing product were combined and concentrated. The material was then purified by preparative HPLC (SunFire C-18 19×150 mm, H$_2$O/MeCN w/0.5 mM NH$_4$OAc, 8 min, 254 nm). The product, 7-(1,4-dimethyl-1H-1,2,3-triazol-5-yl)-8-fluoro-5-((S)-(2-fluorophenyl)(tetrahydro-2H-pyran-4-yl)methyl)-3-(methylsulfonyl)-5H-pyrido[3,2-b]indole (17.2 mg, 26%) was obtained as a colourless solid: HPLC: RT=0.87 min (Waters Acquity UPLC BEH C18 1.7 um 2.0×50 mm, CH$_3$CN/H$_2$O/0.05% TFA, 1 min gradient, wavelength=254 nm); MS (ES): m/z=552 [M+1]$^+$; $^1$H NMR (400 MHz, DMSO-d$_6$) δ 9.01 (d, J=1.54 Hz, 1H), 8.20-8.32 (m, 2H), 7.27-7.41 (m, 2H), 7.05-7.18 (m, 1H), 6.19 (d, J=11.44 Hz, 1H), 3.85-3.96 (m, 3H), 3.71 (br dd, J=2.64, 11.44 Hz, 1H), 3.44 (s, 4H), 3.22 (br t, J=11.11 Hz, 1H), 2.18 (br s, 2H), 1.56-1.79 (m, 2H), 1.35-1.49 (m, 1H), 0.79 (br d, J=11.66 Hz, 1H).

Example 26

5-{3-Methanesulfonyl-5-[(S)-oxan-4-yl(phenyl)methyl]-5H-pyrido[3,2-b]indol-7-yl}-1,4-dimethyl-1H-1,2,3-triazole

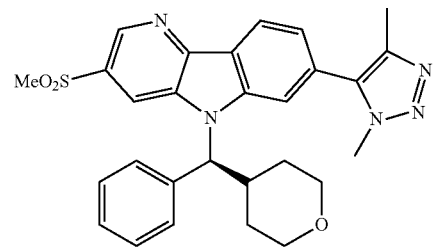 [SMILES: Cc1nnn(C)c1-c1ccc2c3ncc(S(C)(=O)=O)cc3n([C@H](c3ccccc3)C3CCOCC3)c2c1]

Step 1: tert-Butyl (4-(5-bromo-3-nitropyridin-2-yl)phenyl)carbamate

To a stirred solution of tert-butyl (4-(4,4,5,5-tetramethyl-1,3,2-dioxaborolan-2-yl)phenyl)carbamate (1.14 g, 3.57 mmol), 2,5-dibromo-3-nitropyridine (1.00 g, 3.55 mmol), and $PdCl_2$(dppf) (29.6 mg, 0.040 mmol) in tetrahydrofuran (36 mL) at room temperature was added tripotassium phosphate (3M in $H_2O$, 3.6 mL, 10.8 mmol), purged with $N_2$ (vacuum/$N_2$×3), and the reaction was heated at 75° C. with stirring for 48 h. The reaction was cooled to room temperature, concentrated in vacuo, dissolved in DCM, washed with water, the organic phase was separated, dried over magnesium sulfate, filtered, and concentrated. The residue was purified by flash chromatography (Teledyne ISCO CombiFlash Rf, gradient of 0% to 100% using solvent A/B=hexanes/EtOAc over 12 column volumes, RediSep $SiO_2$ 80 g, loaded as DCM solution). The product, tert-butyl (4-(5-bromo-3-nitropyridin-2-yl)phenyl)carbamate (980.8 mg, 70%) was obtained as a yellow solid: HPLC: RT=1.07 min (Waters Acquity UPLC BEH C18 1.7 um 2.0×50 mm, $CH_3CN/H_2O$/0.05% TFA, 1 min gradient, wavelength=254 nm); MS (ES): m/z=394/396 $^{79}Br/^{81}Br$ $[M+1]^+$; $^1H$ NMR (400 MHz, $CDCl_3$) 8.88 (d, J=2.0 Hz, 1H), 8.24 (d, J=2.0 Hz, 1H), 7.55-7.45 (m, 4H), 6.60 (s, 1H), 1.54 (s, 9H).

Step 2: tert-Butyl (4-(5-(methylsulfonyl)-3-nitropyridin-2-yl)phenyl)carbamate To a 40 mL I-Chem vial equipped with a stir bar under ambient atmosphere, was added tert-butyl (4-(5-bromo-3-nitropyridin-2-yl)phenyl)carbamate (501.3 mg, 1.27 mmol), sodium methanesulfinate (585.7 mg, 5.74 mmol), copper(I) iodide (146.8 mg, 0.771 mmol), L-proline (147.1 mg, 1.28 mmol), and $Cs_2CO_3$ (277.3 mg, 0.851 mmol). The vial was sealed with a PTFE-lined septum screw-cap, DMSO (12.7 mL) was added, then the atmosphere purged with $N_2$ (vacuum/$N_2$×4). The reaction was then heated to 100° C. with stirring for 2.5 h. The reaction was cooled to room temperature. The reaction was diluted with $Et_2O$, washed with $H_2O$ (2×100 mL), sat. NaCl then dried over magnesium sulfate, filtered, and concentrated in vacuo. The product, tert-butyl (4-(5-(methylsulfonyl)-3-nitropyridin-2-yl)phenyl)carbamate (390.1 mg, 78% yield) was obtained as a yellow solid: HPLC: RT=0.94 min (Waters Acquity UPLC BEH C18 1.7 um 2.0×50 mm, $CH_3CN/H_2O$/0.05% TFA, 1 min gradient, wavelength=254 nm); MS (ES): m/z=394 $[M+1]^+$; $^1H$ NMR (400 MHz, $CDCl_3$) 9.28 (d, J=2.0 Hz, 1H), 8.57 (d, J=2.0 Hz, 1H), 7.65-7.59 (m, 2H), 7.55-7.49 (m, 2H), 6.66 (s, 1H), 3.22 (s, 3H), 1.55 (s, 9H).

Step 3: 4-(5-(Methylsulfonyl)-3-nitropyridin-2-yl)aniline

To a stirred suspension of tert-butyl (4-(5-(methylsulfonyl)-3-nitropyridin-2-yl)phenyl)carbamate (390.1 mg, 0.992 mmol) in dioxane (2.5 mL) was added HCl (4M in dioxane, 2.5 mL, 10.0 mmol), and the mixture was stirred at room temperature overnight. Reaction diluted with $Et_2O$, the resulting solid was collected by filtration, washed with $Et_2O$, air dry. The product, 4-(5-(methylsulfonyl)-3-nitropyridin-2-yl)aniline, HCl (318.4 mg, 97%) was obtained as a dark yellow solid: HPLC: RT=0.65 min (Waters Acquity UPLC BEH C18 1.7 um 2.0×50 mm, $CH_3CN/H_2O$/0.05% TFA, 1 min gradient, wavelength=254 nm); MS (ES): m/z=294 $[M+1]^+$.

Material was partitioned between DCM and sat. $NaHCO_3$ to generate the free base, the organic phase was separated and dried over magnesium sulfate, filtered, and concentrated. The free base (259.0 mg, 89%) was obtained as a dark yellow solid.

Step 4: 2-(4-Bromophenyl)-5-(methylsulfonyl)-3-nitropyridine

A stirred solution of copper(II) bromide (323.2 mg, 1.45 mmol) in acetonitrile (3.8 mL) was heated to 60° C. To the warm (60° C.), stirred solution was added tert-butyl nitrite (0.17 mL, 1.43 mmol), then a solution of 4-(5-(methylsulfonyl)-3-nitropyridin-2-yl)aniline (259.0 mg, 0.883 mmol) in acetonitrile (3.0 mL) was added dropwise over 5 min, with concomitant evolution of gas, and stirred for 35 min. Concentrated in vacuo. The residue was dissolved in EtOAc, washed with 9:1 sat. $NH_4Cl$: conc $NH_4OH$, sat. NaCl then dried over magnesium sulfate, filtered, and concentrated in vacuo. The product, 2-(4-bromophenyl)-5-(methylsulfonyl)-3-nitropyridine (319.0 mg, 100% yield) was obtained as a tan solid: HPLC: RT=0.94 min (Waters Acquity UPLC BEH C18 1.7 um 2.0×50 mm, $CH_3CN/H_2O$/0.05% TFA, 1 min gradient, wavelength=254 nm); MS (ES): m/z=357/359 $^{79}Br/^{81}Br$ $[M+1]^+$.

Step 5: 7-Bromo-3-(methylsulfonyl)-5H-pyrido[3,2-b]indole

A 100 mL round-bottomed flask was charged with 2-(4-bromophenyl)-5-(methylsulfonyl)-3-nitropyridine (319.0 mg, 0.893 mmol) and DPPE (470.8 mg, 1.18 mmol) in 2,3-dichlorobenzene (3.6 mL) and the contents were heated at 170° C. with stirring 35 min. The reaction was cooled to room temperature and concentrated in vacuo. The residue was suspended in DCM and the resulting solid removed by filtration. From 83.2 mg of a tan solid was obtained. The filtrate was concentrated, the residue was dissolved in THF, $SiO_2$ (6 g) was added, concentrated then dried under vacuum. The material was then purified by flash chromatography (Teledyne ISCO CombiFlash Rf, gradient of 0% to 100% using solvent A/B=$CH_2Cl_2$/acetone over 15 column volumes, RediSep $SiO_2$ 40 g). Obtained an additional 67.6 mg product, combined with solid isolated above. The product, 7-bromo-3-(methylsulfonyl)-5H-pyrido[3,2-b]indole (150.8 mg, 52%) was obtained as a brown solid: HPLC: RT=0.81 min (Waters Acquity UPLC BEH C18 1.7 um 2.0×50 mm, $CH_3CN/H_2O$/0.05% TFA, 1 min gradient, wavelength=254 nm); MS (ES): m/z=324/326 $^{79}Br/^{81}Br$ $[M+1]^+$.

Step 6: (S)-7-Bromo-3-(methylsulfonyl)-5-(phenyl(tetrahydro-2H-pyran-4-yl)methyl)-5H-pyrido[3,2-b]indole To a cool (0° C.), stirred solution of 7-bromo-3-(methylsulfonyl)-5H-pyrido[3,2-b]indole (83.2 mg, 0.256 mmol), (R)-phenyl(tetrahydro-2H-pyran-4-yl)methanol (100.1 mg, 0.521 mmol), and triphenylphosphine (145.7 mg, 0.556 mmol) in THF (5.1 mL) under $N_2$ was added DIAD (0.10 mL, 0.514 mmol) dropwise via syringe, stirred for 5 min, then removed from ice bath and stirred overnight. Concentrated in vacuo, the residue was dissolved in DCM, washed with 1N HCl, brine, dried over magnesium sulfate, filtered, and concentrated. The residue was purified by flash chromatography (Teledyne ISCO CombiFlash Rf, gradient of 0% to 100% using solvent A/B=$CH_2Cl_2$/acetone over 15 column volumes, RediSep SiO$_2$ 24 g, loaded as DCM solution). Fractions containing product were collected and concentrated. The product, (S)-7-bromo-3-(methylsulfonyl)-5-(phenyl(tetrahydro-2H-pyran-4-yl)methyl)-5H-pyrido[3,2-b]indole (145.3 mg, >100%) was obtained as a pale yellow solid: HPLC: RT=1.02 min (Waters Acquity UPLC BEH C18 1.7 um 2.0×50 mm, CH$_3$CN/H$_2$O/0.05% TFA, 1 min gradient, wavelength=254 nm); MS (ES): m/z=499/501 $^{79}$Br/$^{81}$Br [M+1]$^+$.

Step 7: 5-{3-Methanesulfonyl-5-[(S)-oxan-4-yl(phenyl)methyl]-5H-pyrido[3,2-b]indol-7-yl}-1,4-dimethyl-1H-1,2,3-triazole To a 40 mL vial equipped with a stir bar under ambient atmosphere, was added (S)-7-bromo-3-(methylsulfonyl)-5-(phenyl(tetrahydro-2H-pyran-4-yl)methyl)-5H-pyrido[3,2-b]indole (65.3 mg, 0.131 mmol), 1,4-dimethyl-5-(tributylstannyl)-1H-1,2,3-triazole (127.3 mg, 0.330 mmol) in DMF (2.0 mL). Through the stirring solution was bubbled N$_2$ for 5 min, then while bubbling continued Pd(Ph$_3$P)$_4$ (30.6 mg, 0.026 mmol) and copper(I) iodide (24.4 mg, 0.128 mmol) were added, the vial capped, then heated to 95° C. with stirring overnight. Reaction cooled to room temperature and filtered through a 4μ membrane filter. The crude material was purified via preparative LC/MS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-55% B over 25 minutes, then a 5-minute hold at 55% B; Flow: 20 mL/min. Fractions containing the desired product were combined and dried via centrifugal evaporation. Obtained the product (3.4 mg, 5%): HPLC: RT=1.51 min (Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm); MS (ES): m/z=515 [M+1]$^+$; $^1$H NMR (500 MHz, DMSO-d$_6$) δ 9.00 (br s, 1H), 8.44 (br d, J=8.08 Hz, 1H), 7.66 (br d, J=7.74 Hz, 2H), 7.45 (br d, J=8.08 Hz, 1H), 7.29-7.36 (m, 1H), 7.22-7.29 (m, 1H), 5.99 (br d, J=11.11 Hz, 1H), 3.97 (br s, 1H), 3.84-3.93 (m, 1H), 3.70 (br d, J=10.10 Hz, 1H), 3.39-3.55 (m, 3H), 3.24 (br t, J=11.44 Hz, 1H), 2.54 (s, 1H), 2.26 (br s, 2H), 1.74 (br d, J=13.13 Hz, 1H), 1.53-1.66 (m, 1H), 1.27-1.41 (m, 1H), 0.90 (br d, J=12.12 Hz, 1H).

Example 27

5-{3-Methanesulfonyl-5-[(S)-oxan-4-yl(phenyl)methyl]-5H-pyrido[3,2-b]indol-7-yl}-4-($^2$H$_3$)methyl-1-methyl-1H-1,2,3-triazole

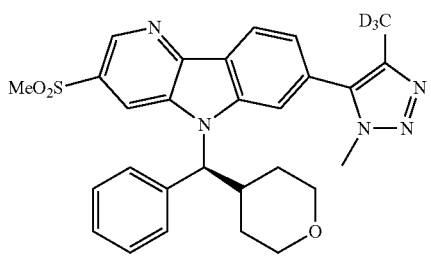 [SMILES: [2H]C([2H])([2H])c1nnn(C)c1-c1ccc2c3ncc(S(C)(=O)=O)cc3n([C@H](c3ccccc3)C3CCOCC3)c2c1]

To a 25 mL RB flask equipped with a stir bar under ambient atmosphere, was added (S)-7-bromo-3-(methylsulfonyl)-5-(phenyl(tetrahydro-2H-pyran-4-yl)methyl)-5H-pyrido[3,2-b]indole (85.1 mg, 0.170 mmol), 1-methyl-4-($^2$H$_3$)methyl-5-tributylstannyl-1H-1,2,3-triazole (165.7 mg, 0.359 mmol) in DMF (3.4 mL). Through the stirring solution was bubbled N$_2$ for 5 min, then while bubbling continued Pd(Ph$_3$P)$_4$ (26.6 mg, 0.023 mmol) and copper(I) iodide (25.8 mg, 0.135 mmol) were added, the flask capped with a septum, then heated to 95° C. with stirring overnight. Reaction cooled to room temperature. To the solution was added TBAF (1M in THF, 1.7 mL, 1.70 mmol). The mixture was filtered through a 4μ membrane filter, concentrated. The residue was dissolved in EtOAc, washed with H$_2$O, sat. NaCl then dried over magnesium sulfate, filtered, and concentrated in vacuo. The residue was dissolved in DMF (2 mL), filtered through a 4μ membrane filter, and purified via preparative LC/MS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 minutes, then a 5-minute hold at 100% B; Flow: 20 mL/min. Fractions containing the desired product were combined and dried via centrifugal evaporation. Obtained the product (5.9 mg, 6%): HPLC: RT=1.520 min (Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm); MS (ES): m/z=519 [M+1]$^+$; $^1$H NMR (500 MHz, DMSO-d$_6$) δ 9.00 (s, 1H), 8.44 (d, J=8.08 Hz, 1H), 7.67 (br d, J=7.41 Hz, 2H), 7.45 (br d, J=8.08 Hz, 1H), 7.32-7.38 (m, 2H), 7.23-7.29 (m, 1H), 6.00 (br d, J=11.44 Hz, 1H), 3.98 (br s, 1H), 3.84-3.93 (m, 1H), 3.70 (br d, J=10.77 Hz, 1H), 3.47 (br d, J=14.47 Hz, 1H), 3.24 (br t, J=11.95 Hz, 1H), 3.09-3.18 (m, 2H), 2.54 (s, 2H), 1.74 (br d, J=11.78 Hz, 1H), 1.51-1.66 (m, 3H), 1.31 (td, J=7.53, 14.89 Hz, 3H), 0.92 (br t, J=7.24 Hz, 4H).

Example 28

5-{8-Fluoro-5-[(S)-(2-fluorophenyl)(oxan-4-yl)methyl]-3-methanesulfonyl-5H-pyrido[3,2-b]indol-7-yl}-4-($^2$H$_3$)methyl-1-methyl-1H-1,2,3-triazole

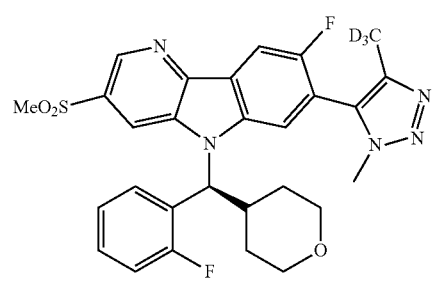 [SMILES: [2H]C([2H])([2H])c1nnn(C)c1-c1cc2c(cc1F)c1ncc(S(C)(=O)=O)cc1n2[C@H](c1ccccc1F)C1CCOCC1]

To a 25 mL RB flask equipped with a stir bar under ambient atmosphere, was added (S)-7-chloro-8-fluoro-5-((2-fluorophenyl)(tetrahydro-2H-pyran-4-yl)methyl)-3-(methylsulfonyl)-5H-pyrido[3,2-b]indole (107.6 mg, 0.219 mmol), 1-methyl-4-($^2$H$_3$)methyl-5-tributylstannyl-1H-1,2,3-triazole (178.3 mg, 0.458 mmol), Pd$_2$(dba)$_3$ (25.3 mg, 0.028 mmol), and Cs$_2$CO$_3$ (151.3 mg, 0.464 mmol). The flask was sealed with a septum, dioxane (2.2 mL) and tricyclohexylphosphine (30% in toluene, 52.0 mg, 0.056 mmol) were added, then the atmosphere purged with N$_2$ (vacuum/N$_2$×4). The reaction was then heated to 115° C. with stirring overnight. The reaction was cooled to room temperature. Next the reaction mixture was diluted with EtOAc, filtered through a 4µ membrane filter and concentrated. The residue was purified by flash chromatography (Teledyne ISCO CombiFlash Rf, gradient of 0% to 50% using solvent A/B=CH$_2$Cl$_2$/acetone over 10 column volumes, RediSep SiO$_2$ 40 g, loaded as DCM solution). Fractions containing product were collected and concentrated. The residue was repurified by flash chromatography (Teledyne ISCO CombiFlash Rf, gradient of 0% to 20% using solvent A/B=CH$_2$Cl$_2$/MeOH over 30 column volumes, RediSep SiO$_2$ 24 g, loaded as DCM solution). Fractions containing product were collected and concentrated. The mixture was diluted with 2 mL CH$_3$CN, then the mixture was purified by Preparative HPLC (SunFire C-18 19×150 mm, H$_2$O/MeCN w/0.5 mM NH$_4$OAc, 8 min, 254 nm). The product (24.5 mg, 20%) was obtained as a colorless solid: HPLC: RT=0.86 min (Waters Acquity UPLC BEH C18 1.7 um 2.0×50 mm, CH$_3$CN/H$_2$O/0.05% TFA, 1 min gradient, wavelength=254 nm); MS (ES): m/z=555 [M+1]$^+$; $^1$H NMR (400 MHz, DMSO-d$_6$) δ 9.01 (d, J=1.54 Hz, 1H), 8.21-8.33 (m, 2H), 7.26-7.43 (m, 2H), 7.12 (ddd, J=1.43, 7.87, 10.73 Hz, 1H), 6.19 (d, J=11.44 Hz, 1H), 3.84-3.96 (m, 3H), 3.66-3.77 (m, 1H), 3.46-3.54 (m, 2H), 3.22 (br t, J=10.89 Hz, 1H), 1.59-1.79 (m, 2H), 1.42 (dq, J=4.40, 12.32 Hz, 1H), 0.79 (br d, J=11.88 Hz, 1H).

Example 29

7-(Dimethyl-1H-1,2,3-triazol-5-yl)-5-[(S)-(2-fluorophenyl)(oxan-4-yl)methyl]-5H-pyrido[3,2-b]indole-3-carboxylic acid

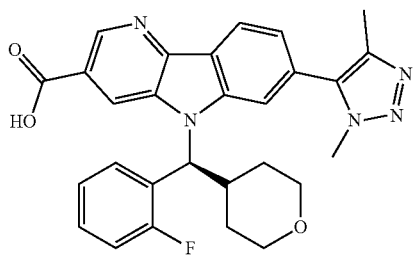 [SMILES: Cc1nnn(C)c1-c1ccc2c3ncc(C(=O)O)cc3n([C@H](c3ccccc3F)C3CCOCC3)c2c1]

To a cool (0° C.), stirred solution of (S)-methyl 7-(1,4-dimethyl-1H-1,2,3-triazol-5-yl)-5-((2-fluorophenyl)(tetrahydro-2H-pyran-4-yl)methyl)-5H-pyrido[3,2-b]indole-3-carboxylate (283 mg, 0.551 mmol) in THF (5.5 mL) was added NaOH (5M, 1.0 mL, 5.0 mmol), the reaction was allowed to warm to room temperature as bath warmed, and stirred overnight. The reaction mixture was diluted with water, neutralized with 1N HCl and diluted with EtOAc. The organic phase was separated, washed with sat. NaCl then dried over sodium sulfate, filtered, and concentrated in vacuo. The product, (S)-7-(1,4-dimethyl-1H-1,2,3-triazol-5-yl)-5-((2-fluorophenyl)(tetrahydro-2H-pyran-4-yl)methyl)-5H-pyrido[3,2-b]indole-3-carboxylic acid (265.9 mg, 97%) was obtained as a cream solid: HPLC: RT=0.77 min (Waters Acquity UPLC BEH C18 1.7 um 2.0×50 mm, CH$_3$CN/H$_2$O/0.05% TFA, 1 min gradient, wavelength=254 nm); MS (ES): m/z=500 [M+1]$^+$.

A portion (21.9 mg) was further purified by preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 0-50% B over 20 minutes, then a 5-minute hold at 100% B; Flow: 20 mL/min. Fractions containing the desired product were combined and dried via centrifugal evaporation. Obtained the product (6.7 mg, 30%): HPLC: RT=0.95 min (Waters Acquity UPLC BEH C18, 2.1×50 mm, 1.7-µm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm); MS (ES): m/z=500 [M+1]$^+$. $^1$H NMR (500 MHz, DMSO-d$_6$) δ 9.04 (br s, 1H), 8.38 (d, J=8.08 Hz, 1H), 8.22 (br s, 1H), 7.25-7.48 (m, 3H), 7.10 (br t, J=9.26 Hz, 1H), 6.15 (br d, J=11.44 Hz, 1H), 3.98 (br s, 2H), 3.81-3.92 (m, 1H), 3.68 (br d, J=11.44 Hz, 1H), 3.19 (br t, J=11.95 Hz, 1H), 2.26 (br s, 2H), 1.58-1.80 (m, 2H), 1.33 (br d, J=11.44 Hz, 1H), 0.73 (br d, J=11.44 Hz, 1H).

Examples 30 and 31

2-{8-Fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol

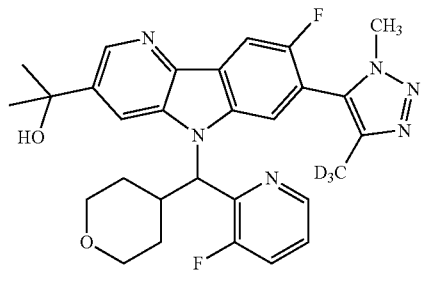

Enantiomer A, Example 30

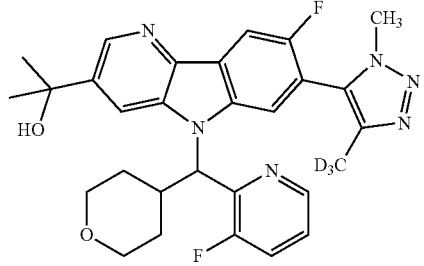

Enantiomer B, Example 31

Step 1: 4-($^2$H$_3$)Methyl-1-((trimethylsilyl)methyl)-1H-1,2,3-triazole

A solution of sodium ascorbate (344 mg, 1.74 mmol) in water (2.2 mL) was added to a stirred solution of trimethyl ($^2$H$_3$-prop-1-yn-1-yl)silane (prepared according to PCT Int. Appl., 2007112352, 4 Oct. 2007, 200 mg, 1.74 mmol) and (azidomethyl)trimethylsilane (294 mg, 1.91 mmol) in t-BuOH (4.3 mL) at ambient temperature. Copper(II) sulfate pentahydrate (87.0 mg, 0.347 mmol) in water (2.2 mL) was subsequently added in a drop wise fashion. The reaction was stirred at ambient temperature for 16 h before it was diluted with water (10 mL) and ethyl acetate (20 mL). The two layers were separated, and the aqueous layer was washed with additional ethyl acetate (2×20 mL). The combined organics were dried over sodium sulfate. The solids were removed by filtration and the volatiles removed under reduced pressure. The crude material was purified using silica gel column chromatography with a gradient of ethyl acetate in hexanes (0-60%). 4-($^2H_3$)Methyl-1-((trimethylsilyl)methyl)-1H-1,2,3-triazole (125 mg, 0.725 mmol, 42%) was isolated as a colorless oil. $^1$H NMR (500 MHz, CDCl$_3$) 7.16 (br. s., 1H), 3.89 (s, 2H), 0.15 (s, 9H); LC/MS (M+H)= 173.2; LC/MS RT=1.20 min (Column: Phenomenex Luna 30×2.0 mm 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: 4-($^2H_3$)Methyl-1-methyl-1H-1,2,3-triazole

TBAF (60.9 mL, 60.9 mmol) was added drop wise to a stirred solution of 4-($^2H_3$)methyl-1-((trimethylsilyl)methyl)-1H-1,2,3-triazole (8.75 g, 50.8 mmol) and water (1.83 mL, 102 mmol) in THF (203 mL) at 0° C. The reaction was stirred at that temperature for 1 h before it was removed from the cold bath and allowed to warm to ambient temperature. The reaction mixture was stirred at ambient temperature for 16 h. The volatiles were removed from the aqueous layer under reduced pressure. The resulting oil was purified using silica gel column chromatography with a gradient of methanol in ethyl acetate (0-20%). 1-Methyl-4-($^2H_3$)methyl-1H-1,2,3-triazole (4.67 g, 46.6 mmol, 92%) was isolated as a yellow oil. $^1$H NMR (500 MHz, DMSO-d$_6$) δ 7.76 (s, 1H), 3.98 (s, 3H); LC/MS (M+H)=101.2; LC/MS RT=0.57 min (Column: Waters Aquity BEH C18 2.1×50 mm 1.7u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min).

Step 3: 4-($^2H_3$)Methyl-1-methyl-5-(tributylstannyl)-1H-1,2,3-triazole n-BuLi (2.5 M in hexanes, 9.59 mL, 24.0 mmol) was added drop wise to a stirred solution of 1-methyl-4-($^2H_3$)methyl-1H-1,2,3-triazole (2.00 g, 20.0 mmol) in THF (49.9 mL) at −78° C. under N$_2$ (g). A white precipitate formed upon addition. The reaction was stirred at that temperature for 30 min before tributyltin chloride (5.96 mL, 22.0 mmol) was added drop wise. The reaction was stirred for an additional 10 min before the cold bath was removed, and the reaction was allowed to warm to ambient temperature over 30 min. The reaction mixture was quenched with saturated aqueous ammonium chloride (20 mL) and diluted with 10% aqueous LiCl (20 mL). The layers were separated, and the aqueous layer extracted with diethyl ether (3×30 mL). The combined organics were dried over sodium sulfate. The solids were removed by filtration and the volatiles removed under reduced pressure. The crude material was purified using silica gel column chromatography with a gradient of ethyl acetate in hexanes (0-50%). 1-Methyl-5-(tributylstannyl)-4-($^2H_3$)methyl-1H-1,2,3-triazole (6.02 g, 15.5 mmol, 77%) was isolated as a colorless oil. $^1$H NMR (500 MHz, DMSO-d$_6$) δ 3.97 (s, 3H), 1.62-1.39 (m, 6H), 1.35-1.25 (m, 6H), 1.24-1.10 (m, 6H), 0.91-0.83 (m, 9H).

Step 4: 5-Bromo-2-(4-chloro-3-fluorophenyl)-3-nitropyridine

A 24/40-3 neck 500 mL round bottom flask was charged with 2,5-dibromo-3-nitropyridine (12.1 g, 42.9 mmol) and 4-chloro-3-fluorophenylboronic acid (7.48 g, 42.9 mmol). The mixture was diluted with THF (150 mL) and aqueous tribasic potassium phosphate (2.0 M, 42.9 mL, 86.0 mmol). PdCl$_2$(dppf) (0.314 g, 0.43 mmol) was added, and the flask was sealed and degassed using sonication and ultra pure argon for 5 min. The mixture was heated to 65° C. After 2 h, the mixture was concentrated under reduced pressure, diluted with ethyl acetate and water, and filtered through Celite. The contents of the vial were transferred into a separatory funnel, and the organics were washed with brine (3×), dried with magnesium sulfate, concentrated under reduced pressure, and purified by silica gel column chromatography (120 g ISCO RediSep Rf, loaded in/with: DCM and dried, fraction size: 18 mL 16×150 mm, and eluted with dichloromethane in hexanes, 0-50%). Only fractions containing pure mono-coupled product were collected and set aside. The remaining impure fractions were collected, concentrated under reduced pressure, and repurified by flash chromatography: (80 g ISCO RediSep Rf, loaded in/with: DCM and dried, initial waste: collected by threshold, fraction size: 18 mL 16×150 mm, and eluted with dichloromethane in hexanes, 0-50%). The fractions were combined to give 10.8 g (67%). $^1$H NMR (400 MHz, CDCl$_3$) 8.93 (d, J=2.0 Hz, 1H), 8.34 (d, J=2.0 Hz, 1H), 7.50 (dd, J=8.2, 7.4 Hz, 1H), 7.41 (dd, J=9.4, 2.1 Hz, 1H), 7.26-7.22 (m, 1H). Mass found 331 [M+H]$^+$.

Step 5: 3-Bromo-7-chloro-6-fluoro-5H-pyrido[3,2-b]indole & 3-bromo-7-chloro-8-fluoro-5H-pyrido[3,2-b]indole A 350 mL-wide neck pressure flask was charged with 5-bromo-2-(4-chloro-3-fluorophenyl)-3-nitropyridine (10.7 g, 32.5 mmol) and 1,2-bis(diphenylphosphino)ethane (19.4 g, 48.7 mmol). The mixture was suspended in 1,2-dichlorobenzene (65 mL). The flask was sealed and placed into an oil bath that was preheated to 160° C. After 30 min, the mixture was concentrated under reduced pressure. The resulting solids were diluted with DCM to give a tan solid, which was collected by filtration to give 3.2 g of the regioisomeric mixture. The supernatant was concentrated under reduced pressure and purified by flash chromatography: (80 g ISCO RediSep Rf, loaded in/with: DCM and dried, fraction size: 18 mL 16×150 mm, and eluted with dichloromethane in hexanes, 0-100%). The fractions were collected and combined with the product that was previously collected. NMR characterization revealed a 1.5:1 ratio of 8F:6F. The mixture was separated by chiral SFC: Chiralpak IB prep column, 30×250 mm, 5 μm. Mobile phase: 10% MeOH in CO$_2$, 150 bar. Temp: 35° C. Flow rate: 70 mL/min for 10 min. UV monitored at 316 nm. Regioisomer 1: 3-bromo-7-chloro-6-fluoro-5H-pyrido[3,2-b]indole (1.69 g, 5.64 mmol, 17%) was isolated as a white solid. $^1$H NMR (400 MHz, CDCl$_3$) 8.65 (d, J=1.8 Hz, 1H), 8.30 (br. s., 1H), 8.02 (d, J=8.5 Hz, 1H), 7.96 (d, J=2.0 Hz, 1H), 7.33 (dd, J=8.5, 6.3 Hz, 1H). SFC retention time: 15.4 min. Mass found 300 [M+H]$^+$. Regioisomer 2: 3-bromo-7-chloro-8-fluoro-5H-pyrido[3,2-b]indole (2.51 g, 8.38 mmol, 26%) was isolated as a white solid. $^1$FI NMR (400 MHz, CDCl$_3$)

8.62 (d, J=1.8 Hz, 1H), 8.06 (d, J=8.5 Hz, 2H), 7.91 (d, J=1.8 Hz, 1H), 7.53 (d, J=5.8 Hz, 1H). SFC retention time: 19.67 min. Mass found 300 [M+H]$^+$.

Step 6: 1-{7-Chloro-8-fluoro-5H-pyrido[3,2-b]indol-3-yl}ethan-1-one

3-Bromo-7-chloro-8-fluoro-5H-pyrido[3,2-b]indole (400 mg, 1.34 mmol), tributyl(1-ethoxyvinyl)tin (965 mg, 2.67 mmol), Pd(PPh$_3$)$_4$ (154 mg, 0.13 mmol), copper(I) iodide (50.9 mg, 0.27 mmol), and triethylamine (242 µL, 1.74 mmol) in DMF (6.8 mL) was degassed with N$_2$ (g) for 3 min. The reaction mixture was subsequently stirred at 100° C. for 16 h. LC/MS showed conversion to the enol ether. 1N Aqueous HCl (2 mL) was added, and the reaction mixture was stirred for 20 min. The reaction mixture was quenched with 1.5 M aqueous monobasic potassium phosphate (5 mL), and the layers were separated. The aqueous layer was extracted with ethyl acetate (3×10 mL). The combined organics were dried over sodium sulfate. The solids were removed by filtration and the volatiles removed under reduced pressure. The crude product was purified using silica gel column chromatography with ethyl acetate in hexanes (0-100%). 1-{7-Chloro-8-fluoro-5H-pyrido[3,2-b]indol-3-yl}ethan-1-one (225 mg, 0.86 mmol, 64% yield) was isolated. LC/MS (M+H)=263.20; LC/MS RT=1.338 min (Column: Phenomenex Luna 30×2.0 mm 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 7: 1-{8-Fluoro-7-[4-($^2$H$_3$)methyl-1-methyl-1H-1,2,3-triazol-5-yl]-5H-pyrido[3,2-b]indol-3-yl}ethan-1-one 1-(7-Chloro-8-fluoro-5H-pyrido[3,2-b]indol-3-yl)ethanone (225 mg, 0.86 mmol), 4-($^2$H$_3$)methyl-1-methyl-5-(tributylstannyl)-1H-1,2,3-triazole (667 mg, 1.71 mmol), Pd$_2$(dba)$_3$ (157 mg, 0.17 mmol), tricyclohexylphosphine (534 µL, 0.34 mmol, 20% wt in toluene), and cesium carbonate (558 mg, 1.71 mmol) in dioxane (8.6 mL) were degassed with N$_2$ (g) for 3 min. The reaction mixture was subsequently stirred at 115° C. for 16 h. 1N Aqueous HCl (2 mL) was added, and the reaction mixture was stirred for 20 min. The reaction mixture was quenched with 1.5 M aqueous monobasic potassium phosphate (5 mL), and the layers were separated. The aqueous layer was extracted with ethyl acetate (3×10 mL). The combined organics were dried over sodium sulfate. The solids were removed by filtration and the volatiles removed under reduced pressure. The crude product was purified using silica gel column chromatography with ethyl acetate in hexanes (0-100%) followed by methanol in ethyl acetate (0-20%). 1-{8-Fluoro-7-[4-($^2$H$_3$)methyl-1-methyl-1H-1,2,3-triazol-5-yl]-5H-pyrido[3,2-b]indol-3-yl}ethan-1-one (37.0 mg, 0.11 mmol, 13% yield) was isolated as a mixture with some unreacted starting material. LC/MS (M+H)=327.20; LC/MS RT=1.175 min (Column: Phenomenex Luna 30×2.0 mm 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min). The material was used in the next step without additional purification.

Step 8: (3-Fluoropyridin-2-yl)(oxan-4-yl)methanol

4-Bromooxane (3.17 g, 19.2 mmol) was added drop wise to a stirred suspension of magnesium (466 mg, 19.2 mmol) and one crystal of iodine in THF (26 mL) at ambient temperature. The reaction mixture was stirred for 30 min before it was cooled in an ice-water bath. 3-Fluoropicolinaldehyde (1.20 g, 9.59 mmol) was added drop wise. The reaction mixture was then stirred for 30 min. The reaction mixture was quenched with saturated aqueous ammonium chloride (40 mL) and diluted with ethyl acetate (100 mL) and water (30 mL). The product was extracted into the organic phase before the layers were separated. The aqueous layer was extracted with a second portion of ethyl acetate (50 mL), and the combined organics were dried over sodium sulfate. The volatiles were removed under reduced pressure. The crude reaction material was purified using silica gel column chromatography. (3-Fluoropyridin-2-yl)(oxan-4-yl)methanol (1.47 g, 6.96 mmol, 73% yield) was isolated as a colorless oil. $^1$H NMR (400 MHz, CDCl$_3$) 8.40-8.45 (m, 1H), 7.40-7.46 (m, 1H), 7.27-7.33 (m, 1H), 4.83-4.88 (m, 1H), 4.00 (td, J=2.14, 11.37 Hz, 2H), 3.36 (ddt, J=2.20, 9.23, 11.77 Hz, 2H), 1.90-2.03 (m, 1H), 1.65-1.78 (m, 1H), 1.57 (dq, J=4.65, 12.47 Hz, 1H), 1.39-1.49 (m, 2H).

Step 9: 1-{8-Fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}ethan-1-one Di-tert-butyl azodicarboxylate (59.9 mg, 0.26 mmol) in THF (1 mL) was added drop wise to a stirred solution of 1-{8-fluoro-7-[4-($^2$H$_3$)methyl-1-methyl-1H-1,2,3-triazol-5-yl]-5H-pyrido[3,2-b]indol-3-yl}ethan-1-one (36.0 mg, 0.11 mmol), (3-fluoropyridin-2-yl)(tetrahydro-2H-pyran-4-yl)methanol (55.0 mg, 0.26 mmol), triphenylphosphine (68.3 mg, 0.26 mmol), and Et$_3$N (36 µL, 0.26 mmol) in THF (1.1 mL) at 0° C. The reaction mixture was allowed to warm to ambient temperature over 10 min and stirred for an additional 16 h at that temperature. The desired product was observed by LC (LC RT=1.462 min, Column: Phenomenex Luna 30×2.0 mm 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min). The crude reaction was used without purification.

Step 10: 2-{8-Fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol Methylmagnesium bromide (259 µL, 0.78 mmol, 3 M) was added to a stirred solution of 1-{8-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}ethan-1-one (57.0 mg, 0.11 mmol) in THF (1.1 mL) under N$_2$ (g) at −20° C. The reaction mixture was stirred at that temperature for 2 h. The reaction mixture was then quenched with saturated aqueous ammonium chloride (8 mL) and diluted with ethyl acetate (20 mL) while still at −20° C. The mixture was removed from the cold bath and allowed to warm to ambient temperature. The layers were separated, and the aqueous phase was extracted with a second portion of ethyl acetate (20 mL). The combined organics were dried over sodium sulfate. The solids were removed by filtration and the volatiles removed under reduced pressure. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10 mM ammonium acetate; Gradient: 15-55% B over 15 min, then a 7-min hold at 100% B; Flow: 20 mL/min. Fractions containing the desired product were combined and dried via centrifugal evaporation to afford racemic 2-{8-fluoro-5-[(3-fluoropyridin-2-yl)(oxan-4-yl)methyl]-7-[4-($^2$H$_3$)methyl-1-methyl-1H-1,2,3-triazol-5-yl}-5H-pyrido[3,2-b]indol-3-yl] propan-2-ol. Enantiomers A and B were separated using chiral preparative HPLC (Column: Chiralpak OD 21×250 mm 10u; Mobile Phase: 10% ethanol in heptane with 0.1% diethylamine; Flow: 15 mL/min). The first eluting enantiomer (21.10 min) was defined as Enantiomer A (2.2 mg, 4% yield), and the second eluting enantiomer (31 min) was defined as Enantiomer B (2.0 mg, 3% yield). $^1$H NMR (500 MHz, DMSO-d$_6$) δ 8.68 (br. s., 1H), 8.60 (d, J=4.40 Hz, 1H), 8.43 (br. s., 1H), 8.12 (d, J=9.54 Hz, 1H), 7.69 (t, J=8.80 Hz, 1H), 7.46-7.52 (m, 1H), 6.20 (d, J=10.27 Hz, 1H), 3.89-4.06 (m, 3H), 3.86 (d, J=11.37 Hz, 1H), 3.70 (d, J=9.90 Hz, 1H), 3.39-3.53 (m, 3H), 3.19 (t, J=11.37 Hz, 1H), 1.43-1.72 (m, 8H), 1.18-1.39 (m, 2H), 0.69 (d, J=12.47 Hz, 1H). LC/MS (M+H)=536.30; LC/MS RT=1.225 min (Column: Phenomenex Luna 30×2.0 mm 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Example 32

2-{8-Fluoro-7-[4-($^2$H$_3$)methyl-1-methyl-1H-1,2,3-triazol-5-yl]-5-[(S)-(oxan-4-yl)(phenyl)methyl]-5H-pyrido[3,2-b]indol-3-yl}propan-2-ol

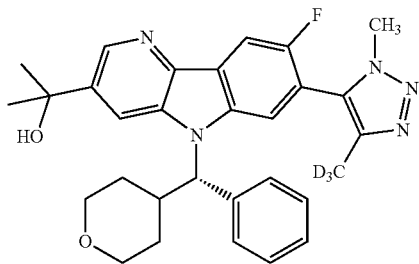 [SMILES: [2H]C([2H])([2H])c1nnn(C)c1-c1cc2c(cc1F)c1ncc(C(C)(C)O)cc1n2[C@H](c1ccccc1)C1CCOCC1]

Step 1: 3-Bromo-7-chloro-8-fluoro-5-[(S)-(oxan-4-yl)(phenyl)methyl]-5H-pyrido[3,2-b]indole Di-tert-butyl azodicarboxylate (308 mg, 1.36 mmol) in THF (1.0 mL) was added drop wise to a stirred solution of 3-bromo-7-chloro-8-fluoro-5H-pyrido[3,2-b]indole (200 mg, 0.67 mmol), (R)-phenyl(tetrahydro-2H-pyran-4-yl)methanol (257 mg, 1.34 mmol), triphenylphosphine (350 mg, 1.36 mmol), and Et$_3$N (186 μL, 1.36 mmol) in THF (6.7 mL) at 0° C. The reaction mixture was allowed to warm to ambient temperature over 10 min and stirred for an additional 16 h at that temperature. The crude reaction mixture was loaded onto a silica gel column and purified using ethyl acetate in hexanes (0-100%). 3-Bromo-7-chloro-8-fluoro-5-[(S)-(oxan-4-yl)(phenyl)methyl]-5H-pyrido[3,2-b]indole (353 mg, 0.75 mmol, >100% yield) was isolated as a colorless oil with a minor triphenylphosphine oxide contaminant. LC/MS (M+3H)=475.05; LC/MS RT=2.151 min (Column: Phenomenex Luna 30×2.0 mm 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min). The material was used without additional purification.

Step 2: 1-{7-Chloro-8-fluoro-5-[(S)-(oxan-4-yl)(phenyl)methyl]-5H-pyrido[3,2-b]indol-3-yl}ethan-1-one 3-Bromo-7-chloro-8-fluoro-5-[(S)-(oxan-4-yl)(phenyl)methyl]-5H-pyrido[3,2-b]indole (350 mg, 0.74 mmol), tributyl(1-ethoxyvinyl)tin (534 mg, 1.48 mmol), Pd(PPh$_3$)$_4$ (85.0 mg, 0.07 mmol), copper(I) iodide (28.1 mg, 0.15 mmol), and triethylamine (134 μL, 0.96 mmol) in DMF (3.7 mL) were degassed with N$_2$ (g) for 3 min. The reaction mixture was subsequently stirred at 100° C. for 16 h. LC/MS showed conversion to the enol ether. 1N Aqueous HCl (2 mL) was added, and the reaction mixture was stirred for 20 min. The reaction mixture was quenched with 1.5 M aqueous monobasic potassium phosphate (5 mL), and the layers were separated. The aqueous layer was extracted with ethyl acetate (3×10 mL). The combined organics were dried over sodium sulfate. The solids were removed by filtration and the volatiles removed under reduced pressure. The crude product was purified using silica gel column chromatography with ethyl acetate in hexanes (0-100%). 1-{7-Chloro-8-fluoro-5-[(S)-(oxan-4-yl)(phenyl)methyl]-5H-pyrido[3,2-b]indol-3-yl}ethan-1-one (165 mg, 0.38 mmol, 51% yield) was isolated. LC/MS (M+H)=437.15; LC/MS RT=1.851 min (Column: Phenomenex Luna 30×2.0 mm 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 3: 1-{8-Fluoro-7-[4-($^2$H$_3$)methyl-1-methyl-1H-1,2,3-triazol-5-yl]-5-[(S)-(oxan-4-yl)(phenyl)methyl]-5H-pyrido[3,2-b]indol-3-yl}ethan-1-one 1-{7-Chloro-8-fluoro-5-[(S)-(oxan-4-yl)(phenyl)methyl]-5H-pyrido[3,2-b]indol-3-yl}ethan-1-one (108 mg, 0.25 mmol), 4-($^2$H$_3$)methyl-1-methyl-5-(tributylstannyl)-1H-1,2,3-triazole (192 mg, 0.49 mmol), Pd$_2$(dba)$_3$ (45.3 mg, 0.05 mmol), tricyclohexylphosphine (154 μL, 0.10 mmol, 20% wt in toluene), and cesium carbonate (161 mg, 0.49 mmol) in dioxane (2.5 mL) were degassed with N$_2$ (g) for 3 min. The reaction mixture was subsequently stirred at 115° C. for 16 h. The crude reaction mixture was purified using silica gel column chromatography with ethyl acetate in hexanes (0-100%) followed by methanol in ethyl acetate (0-20%). 1-{8-Fluoro-7-[4-($^2$H$_3$)methyl-1-methyl-1H-1,2,3-triazol-5-yl]-5-[(S)-(oxan-4-yl)(phenyl)methyl]-5H-pyrido[3,2-b]indol-3-yl}ethan-1-one (124 mg, 0.25 mmol, 100% yield) was isolated as a mixture with some unreacted starting material. LC/MS (M+H)=501.20; LC/MS RT=1.551 min (Column: Phenomenex Luna 30×2.0 mm 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min). The material was used in the next step without additional purification.

Step 4: 2-{8-Fluoro-7-[4-($^2$H$_3$)methyl-1-methyl-1H-1,2,3-triazol-5-yl]-5-[(S)-(oxan-4-yl)(phenyl)methyl]-5H-pyrido[3,2-b]indol-3-yl}propan-2-ol Methylmagnesium bromide (248 μL, 0.74 mmol, 3 M) was added to a stirred solution of 1-{8-fluoro-7-[4-($^2$H$_3$)methyl-1-methyl-1H-1,2,3-triazol-5-yl]-5-[(S)-(oxan-4-yl)

(phenyl)methyl]-5H-pyrido[3,2-b]indol-3-yl}ethan-1-one (124 mg, 0.25 mmol) in THF (1.1 mL) under N$_2$ (g) at −20° C. The reaction mixture was stirred at that temperature for 1 h. The reaction mixture was then quenched with saturated aqueous ammonium chloride (8 mL) and diluted with ethyl acetate (20 mL) while still at −20° C. The mixture was removed from the cold bath and allowed to warm to ambient temperature. The layers were separated, and the aqueous phase was extracted with a second portion of ethyl acetate (20 mL). The combined organics were dried over sodium sulfate The solids were removed by filtration and the volatiles removed under reduced pressure. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10 mM ammonium acetate; Gradient: 50-100% B over 20 min, then a 5-min hold at 100% B; Flow: 20 mL/min. Fractions containing the desired product were combined and dried via centrifugal evaporation to afford 2-{8-fluoro-7-[4-($^2$H$_3$)methyl-1-methyl-1H-1,2,3-triazol-5-yl]-5-[(S)-(oxan-4-yl)(phenyl)methyl]-5H-pyrido[3,2-b]indol-3-yl}propan-2-ol (8.7 mg, 0.02 mmol, 7% yield). LC/MS (M+H)=517.30; LC/MS RT=1.269 min (Column: Phenomenex Luna 30×2.0 mm 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min). $^1$H NMR (500 MHz, DMSO-d$_6$) δ 8.70 (s, 1H), 8.42 (br. s., 1H), 8.04-8.21 (m, 2H), 7.64 (d, J=7.70 Hz, 2H), 7.29-7.38 (m, 2H), 7.21-7.28 (m, 1H), 5.83 (d, J=11.00 Hz, 1H), 3.84-3.99 (m, 4H), 3.74 (d, J=9.54 Hz, 1H), 3.48 (t, J=11.37 Hz, 1H), 3.30-3.43 (m, 1H), 3.26 (t, J=11.92 Hz, 1H), 1.69 (d, J=13.20 Hz, 1H), 1.50-1.64 (m, 7H), 1.24-1.37 (m, 1H), 0.99 (d, J=12.84 Hz, 1H).

Example 33

2-{8-Fluoro-7-[5-($^2$H$_3$)methyl-3-methyl-1,2-oxazol-4-yl]-5-[(S)-(oxan-4-yl)(phenyl)methyl]-5H-pyrido[3,2-b]indol-3-yl}propan-2-ol

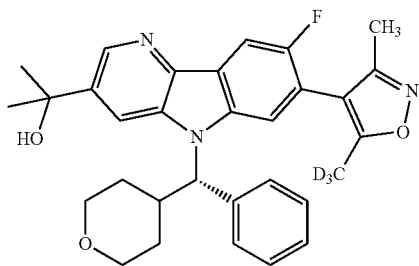 [SMILES: [2H]C([2H])([2H])c1onc(C)c1-c1cc2c(cc1F)c1ncc(C(C)(C)O)cc1n2[C@H](c1ccccc1)C1CCOCC1]

Step 1: 1-[7-(Dimethyl-1,2-oxazol-4-yl)-8-fluoro-5-[(S)-(oxan-4-yl)(phenyl)methyl]-5H-pyrido[3,2-b]indol-3-yl]ethan-1-one 1-{7-Chloro-8-fluoro-5-[(S)-(oxan-4-yl)(phenyl)methyl]-5H-pyrido[3,2-b]indol-3-yl}ethan-1-one (prepared in route to 2-{8-fluoro-7-[4-($^2$H$_3$)methyl-1-methyl-1H-1,2,3-triazol-5-yl]-5-[(S)-(oxan-4-yl)(phenyl)methyl]-5H-pyrido[3,2-b]indol-3-yl}propan-2-ol, 54.0 mg, 0.12 mmol), (3,5-dimethylisoxazol-4-yl)boronic acid (34.8 mg, 0.25 mmol), Pd$_2$(dba)$_3$ (22.6 mg, 0.03 mmol), tricyclohexylphosphine (77 μL, 0.05 mmol), and cesium carbonate (81.0 mg, 0.25 mmol) in dioxane (1.2 mL) was degassed with N$_2$ (g) for 3 min. The reaction mixture was subsequently stirred at 115° C. for 16 h. 1N Aqueous HCl (2 mL) was added, and the reaction mixture was stirred for 20 min. The reaction mixture was quenched with 1.5 M aqueous monobasic potassium phosphate (5 mL), and the layers were separated. The aqueous layer was extracted with ethyl acetate (3×10 mL). The combined organics were dried over sodium sulfate. The solids were removed by filtration and the volatiles removed under reduced pressure. The crude product was purified using silica gel column chromatography with ethyl acetate in hexanes (0-100%) followed by methanol in ethyl acetate (0-20%). 1-[7-(Dimethyl-1,2-oxazol-4-yl)-8-fluoro-5-[(S)-(oxan-4-yl)(phenyl)methyl]-5H-pyrido[3,2-b]indol-3-yl]ethan-1-one (61.0 mg, 0.12 mmol, 99% yield) was isolated as a mixture with some unreacted chloride starting material. LC/MS (M+H)=498.25; LC/MS RT=1.765 min (Column: Phenomenex Luna 30×2.0 mm 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min). The material was used without additional purification.

Step 2: 2-[7-(Dimethyl-1,2-oxazol-4-yl)-8-fluoro-5-[(S)-(oxan-4-yl)(phenyl)methyl]-5H-pyrido[3,2-b]indol-3-yl]propan-2-ol Methylmagnesium bromide (1.23 mL, 3.68 mmol, 3 M) was added to a stirred solution of 1-[7-(dimethyl-1,2-oxazol-4-yl)-8-fluoro-5-[(S)-(oxan-4-yl)(phenyl)methyl]-5H-pyrido[3,2-b]indol-3-yl]ethan-1-one (61.0 mg, 0.12 mmol) in THF (1.2 mL) under N$_2$ (g) at −20° C. The reaction mixture was stirred at that temperature for 1 h. The reaction mixture was then quenched with saturated aqueous ammonium chloride (8 mL) and diluted with ethyl acetate (20 mL) while still at −20° C. The mixture was removed from the cold bath and allowed to warm to ambient temperature. The layers were separated, and the aqueous phase was extracted with a second portion of ethyl acetate (20 mL). The combined organics were dried over sodium sulfate. The solids were removed by filtration and the volatiles removed under reduced pressure. Crude 2-[7-(dimethyl-1,2-oxazol-4-yl)-8-fluoro-5-[(S)-(oxan-4-yl)(phenyl)methyl]-5H-pyrido[3,2-b]indol-3-yl]propan-2-ol (24.9 mg, 40% yield) was used without purification. LC/MS (M+H)=514.25; LC/MS RT=1.412 min (Column: Phenomenex Luna 30×2.0 mm 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 3: 2-{8-Fluoro-7-[5-($^2$H$_3$)methyl-3-methyl-1,2-oxazol-4-yl]-5-[(S)-(oxan-4-yl)(phenyl)methyl]-5H-pyrido[3,2-b]indol-3-yl}propan-2-ol 2-[7-(Dimethyl-1,2-oxazol-4-yl)-8-fluoro-5-[(S)-(oxan-4-yl)(phenyl)methyl]-5H-pyrido[3,2-b]indol-3-yl]propan-2-ol (24.0 mg, 0.05 mmol) and sodium tert-butoxide (31.5 mg, 0.28 mmol) were stirred in CD$_3$OD (467 μL) at 80° C. for 16 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 30 min, then a 5-min hold at 100% B; Flow: 20 mL/min. Fractions containing the desired product were combined and dried via centrifugal evaporation to afford 2-{8-fluoro-7-[5-($^2$H$_3$)methyl-3-methyl-1,2-oxazol-4-yl]-5-[(S)-(oxan-4-yl)(phenyl)methyl]-5H-pyrido[3,2-b]indol-3-yl}propan-2-ol (1.4 mg, 6% yield). LC/MS (M+H)=517.35; LC/MS RT=1.400 min (Column: Phenomenex Luna 30×2.0 mm 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min). $^1$H NMR (500 MHz, DMSO-d$_6$) δ 8.67 (s, 1H), 8.39 (br. s., 1H), 7.84-8.08 (m, 2H), 7.64 (d, J=7.34 Hz, 2H), 7.28-7.39 (m, 2H), 7.20-7.28 (m, 1H), 5.81 (d, J=10.27 Hz, 1H), 3.84-3.94 (m, 1H), 3.68-3.78 (m, 1H), 3.49 (t, J=11.74 Hz, 1H), 3.19-3.44 (m, 2H), 2.31-2.39 (m, 1H), 2.21 (br. s., 3H), 1.51-1.73 (m, 7H), 1.19-1.37 (m, 1H), 0.98 (d, J=13.20 Hz, 1H).

Examples 34 & 35

2-{8-Fluoro-5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol

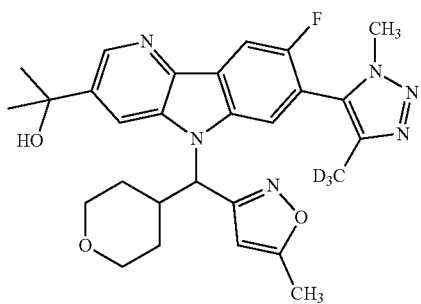

Enantiomer A, Example 34

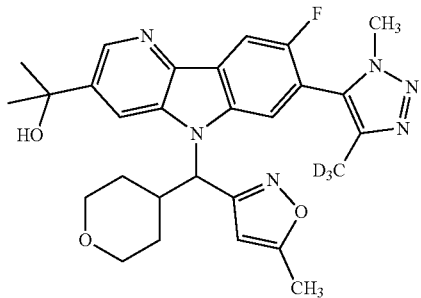

Enantiomer B, Example 35

Step 1: 3-({3-Bromo-7-chloro-8-fluoro-5H-pyrido[3,2-b]indol-5-yl}(oxan-4-yl)methyl)-5-methyl-1,2-oxazole Racemic 3-({3-bromo-7-chloro-8-fluoro-5H-pyrido[3,2-b]indol-5-yl}(oxan-4-yl)methyl)-5-methyl-1,2-oxazole (281 mg, 0.62 mmol, 100% yield, colorless oil) was prepared from 3-bromo-7-chloro-8-fluoro-5H-pyrido[3,2-b]indole (prepared in route to 2-{8-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol) and (5-methyl-1,2-oxazol-3-yl)(oxan-4-yl)methanol (prepared according to Step 8 in route to 2-{8-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol) according to Step 1 in route to 2-{8-fluoro-7-[4-($^2$H$_3$)methyl-1-methyl-1H-1,2,3-triazol-5-yl]-5-[(S)-(oxan-4-yl)(phenyl)methyl]-5H-pyrido[3,2-b]indol-3-yl}propan-2-ol. LC/MS (M+H)=450.00; LC/MS RT=2.343 min (Column: Phenomenex Luna 30×2.0 MM 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: 1-{7-Chloro-8-fluoro-5-[(5-methyl-1,2-oxazol-3-yl)(oxan-4-yl)methyl]-5H-pyrido[3,2-b]indol-3-yl}ethan-1-one Racemic 1-{7-chloro-8-fluoro-5-[(5-methyl-1,2-oxazol-3-yl)(oxan-4-yl)methyl]-5H-pyrido[3,2-b]indol-3-yl}ethan-1-one (98.0 mg, 0.22 mmol, 53% yield, mixture with vinyl ether minor contaminant) was prepared from 3-({3-bromo-7-chloro-8-fluoro-5H-pyrido[3,2-b]indol-5-yl}(oxan-4-yl)methyl)-5-methyl-1,2-oxazole according to Step 2 in route to 2-{8-fluoro-7-[4-($^2$H$_3$)methyl-1-methyl-1H-1,2,3-triazol-5-yl]-5-[(S)-(oxan-4-yl)(phenyl)methyl]-5H-pyrido[3,2-b]indol-3-yl}propan-2-ol. LC/MS (M+H)=442.15; LC/MS RT=1.766 min (Column: Phenomenex Luna 30×2.0 MM 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 3: 1-{8-Fluoro-5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}ethan-1-one Racemic 1-{8-fluoro-5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}ethan-1-one was prepared from 1-{7-chloro-8-fluoro-5-[(5-methyl-1,2-oxazol-3-yl)(oxan-4-yl)methyl]-5H-pyrido[3,2-b]indol-3-yl}ethan-1-one and 4-($^2$H$_3$)methyl-1-methyl-5-(tributylstannyl)-1H-1,2,3-triazole according to Step 3 in route to 2-{8-fluoro-7-[4-($^2$H$_3$)methyl-1-methyl-1H-1,2,3-triazol-5-yl]-5-[(S)-(oxan-4-yl)(phenyl)methyl]-5H-pyrido[3,2-b]indol-3-yl}propan-2-ol. LC/MS (M+H)=506.25; LC/MS RT=1.483 min (Column: Phenomenex Luna 30×2.0 MM 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 4: 2-{8-Fluoro-5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol Enantiomers A and B of 2-{8-fluoro-5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol were prepared according to Step 10 in route to 2-{8-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol. Enantiomers A and B were separated using chiral preparative HPLC (Column: Chiralcel OD 21×250 mm 10u; Mobile Phase: 10% ethanol in heptane with 0.1% diethylamine; Flow: 15 mL/min). The first eluting enantiomer (21.74 min) was defined as Enantiomer A (13.3 mg, 11% yield), and the second eluting enantiomer (26.31 min) was defined as Enantiomer B (12.3 mg, 11% yield). $^1$H NMR (500 MHz, DMSO-d$_6$) δ 8.72 (s, 1H), 8.36 (br. s., 1H), 8.15 (d, J=9.54 Hz, 1H), 8.04 (br. s., 1H), 6.28 (br. s., 1H), 5.99 (d, J=11.00 Hz, 1H), 5.40 (s, 1H), 3.96 (s, 3H), 3.90 (d, J=8.80 Hz, 1H), 3.69 (d, J=9.17 Hz, 1H), 3.41 (t, J=11.37 Hz, 1H), 3.17 (t, J=11.19 Hz, 2H), 2.32 (s, 3H), 1.88 (d, J=12.47 Hz, 1H), 1.53-1.69 (m, 7H), 1.18-1.30 (m, 1H), 0.82 (d, J=12.10 Hz, 1H). LC/MS (M+H)=522.25; LC/MS RT=1.259 min (Column: Phenomenex Luna 30×2.0 MM 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Examples 36-70

The compounds in Table 2 were prepared from commercially available starting materials or intermediates prepared according to analogous procedures described for 2-{8-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, 2-{8-fluoro-7-[4-($^2$H$_3$)methyl-1-methyl-1H-1,2,3-triazol-5-yl]-5-[(S)-(oxan-4-yl)(phenyl)methyl]-5H-pyrido[3,2-b]indol-3-yl}propan-2-ol, or 2-{8-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol:

TABLE 2

| Example | Structure | HPLC T$_R$ (min) | LC/MS (M + H) | HPLC Method |
|---|---|---|---|---|
| 36 Enantiomer A | 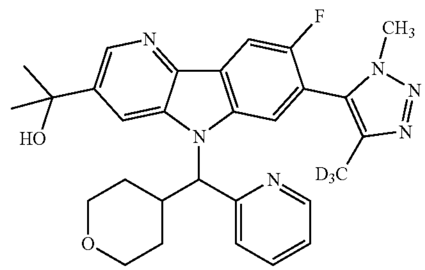 | 18.19 | 518.3 | A |
| 37 Enantiomer B | 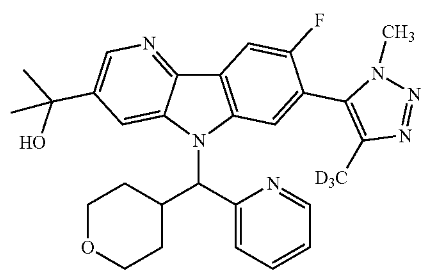 | 23.09 | 518.3 | A |
| 38 Enantiomer A | 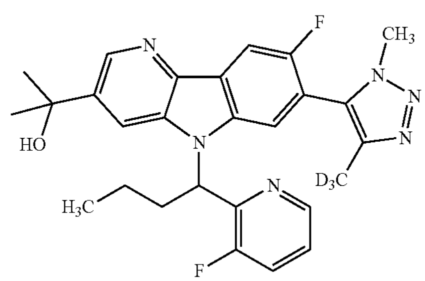 | 26.59 | 494.3 | B |
| 39 Enantiomer B | 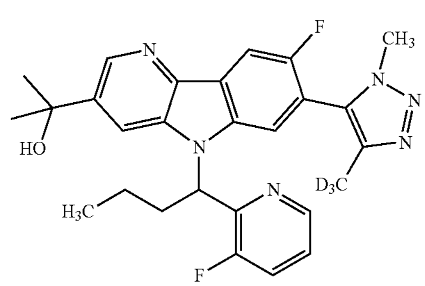 [SMILES: [2H]C([2H])([2H])c1nnn(C)c1-c1cc2c(cc1F)c1ncc(C(C)(C)O)cc1n2C(CCC)c1ncccc1F] | 31.48 | 494.3 | B |

TABLE 2-continued

| Example | Structure | HPLC T$_R$ (min) | LC/MS (M + H) | HPLC Method |
|---|---|---|---|---|
| 40 Enantiomer A | 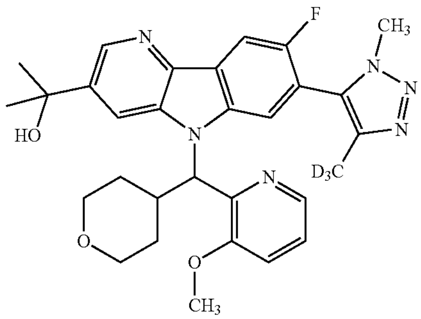 [SMILES: [2H]C([2H])([2H])c1nnn(C)c1-c1cc2c(cc1F)c1ncc(C(C)(C)O)cc1n2C(c1ncccc1OC)C1CCOCC1] | 18.15 | 548.3 | C |
| 41 Enantiomer B | 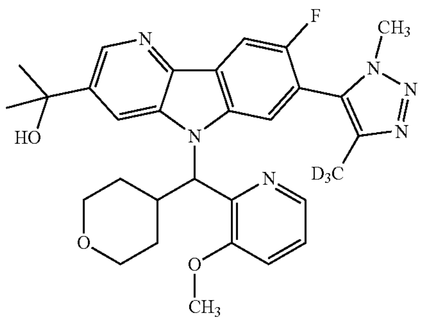 [SMILES: [2H]C([2H])([2H])c1nnn(C)c1-c1cc2c(cc1F)c1ncc(C(C)(C)O)cc1n2C(c1ncccc1OC)C1CCOCC1] | 35.79 | 548.3 | C |
| 42 Enantiomer A | 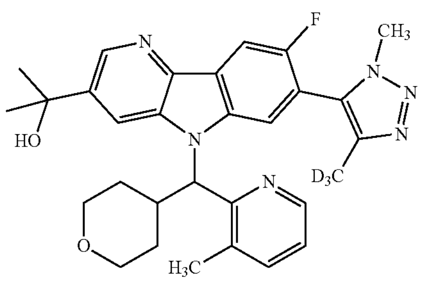 [SMILES: [2H]C([2H])([2H])c1nnn(C)c1-c1cc2c(cc1F)c1ncc(C(C)(C)O)cc1n2C(c1ncccc1C)C1CCOCC1] | 42.19 | 532.3 | B |
| 43 Enantiomer B | 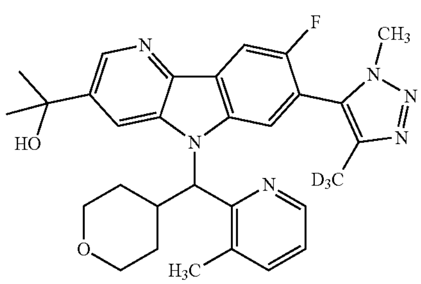 [SMILES: [2H]C([2H])([2H])c1nnn(C)c1-c1cc2c(cc1F)c1ncc(C(C)(C)O)cc1n2C(c1ncccc1C)C1CCOCC1] | 48.26 | 532.3 | B |
| 44 Enantiomer A | 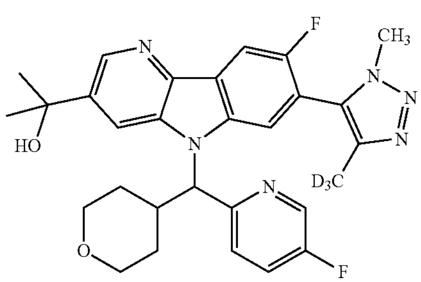 [SMILES: [2H]C([2H])([2H])c1nnn(C)c1-c1cc2c(cc1F)c1ncc(C(C)(C)O)cc1n2C(c1ccc(F)cn1)C1CCOCC1] | 18 | 536.4 | C |

TABLE 2-continued

| Example | Structure | HPLC $T_R$ (min) | LC/MS (M + H) | HPLC Method |
|---|---|---|---|---|
| 45 Enantiomer B | 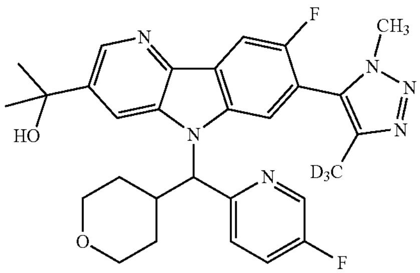 [SMILES: [2H]C([2H])([2H])c1nnn(C)c1-c1cc2c(cc1F)c1ncc(C(C)(C)O)cc1n2C(c1ccc(F)cn1)C1CCOCC1] | 39 | 536.4 | C |
| 46 Enantiomer A | 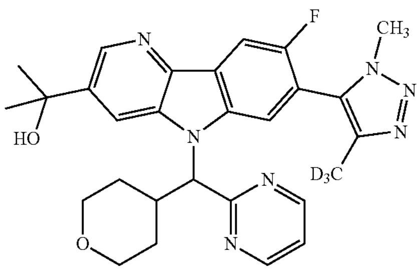 [SMILES: [2H]C([2H])([2H])c1nnn(C)c1-c1cc2c(cc1F)c1ncc(C(C)(C)O)cc1n2C(c1ncccn1)C1CCOCC1] | 18.77 | 519.3 | A |
| 47 Enantiomer B | 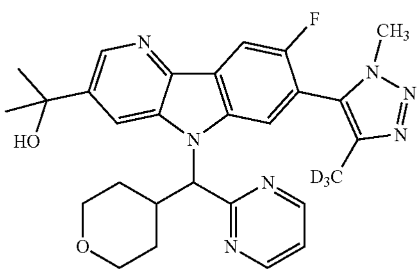 [SMILES: [2H]C([2H])([2H])c1nnn(C)c1-c1cc2c(cc1F)c1ncc(C(C)(C)O)cc1n2C(c1ncccn1)C1CCOCC1] | 24.55 | 519.3 | A |
| 48 Enantiomer A | 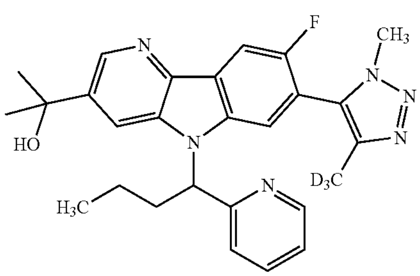 [SMILES: [2H]C([2H])([2H])c1nnn(C)c1-c1cc2c(cc1F)c1ncc(C(C)(C)O)cc1n2C(CCC)c1ccccn1] | 18.12 | 476.3 | D |
| 49 Enantiomer B | 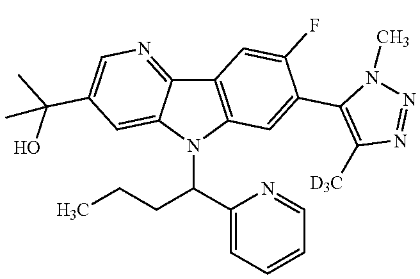 [SMILES: [2H]C([2H])([2H])c1nnn(C)c1-c1cc2c(cc1F)c1ncc(C(C)(C)O)cc1n2C(CCC)c1ccccn1] | 21.88 | 476.3 | D |

TABLE 2-continued

| Example | Structure | HPLC T$_R$ (min) | LC/MS (M + H) | HPLC Method |
|---|---|---|---|---|
| 50 Enantiomer A | 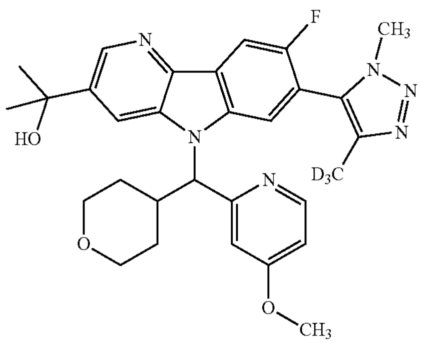 [SMILES: [2H]C([2H])([2H])c1nnn(C)c1-c1cc2c(cc1F)c1ncc(C(C)(C)O)cc1n2C(c1cc(OC)ccn1)C1CCOCC1] | 6.22 | 548.4 | E |
| 51 Enantiomer B | 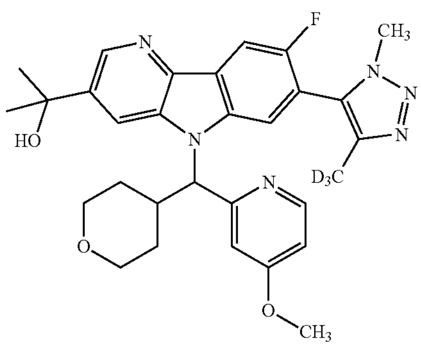 [SMILES: [2H]C([2H])([2H])c1nnn(C)c1-c1cc2c(cc1F)c1ncc(C(C)(C)O)cc1n2C(c1cc(OC)ccn1)C1CCOCC1] | 9.65 | 548.4 | E |
| 52 Enantiomer A | 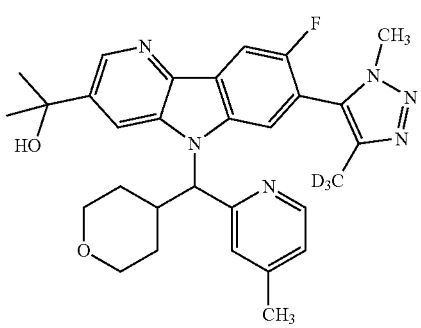 [SMILES: [2H]C([2H])([2H])c1nnn(C)c1-c1cc2c(cc1F)c1ncc(C(C)(C)O)cc1n2C(c1cc(C)ccn1)C1CCOCC1] | 7.50 | 532.4 | F |
| 53 Enantiomer B | 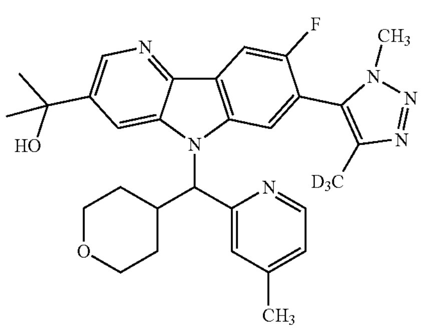 [SMILES: [2H]C([2H])([2H])c1nnn(C)c1-c1cc2c(cc1F)c1ncc(C(C)(C)O)cc1n2C(c1cc(C)ccn1)C1CCOCC1] | 9.72 | 532.4 | F |

TABLE 2-continued
| Example | Structure | HPLC T$_R$ (min) | LC/MS (M + H) | HPLC Method |
|---|---|---|---|---|
| 54 Enantiomer A | 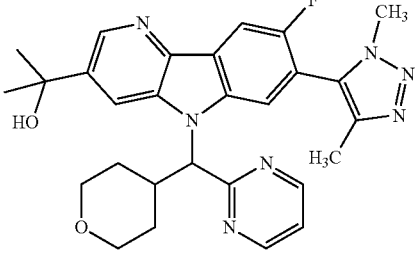 | 16.46 | 516.3 | G |
| 55 Enantiomer B | 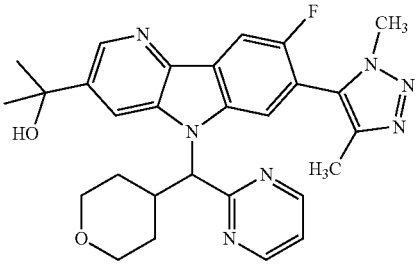 | 21.42 | 516.3 | G |
| 56 Enantiomer A | 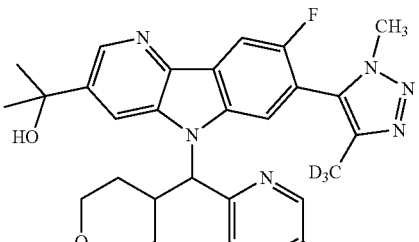 | 46 | 532.4 | B |
| 57 Enantiomer B | 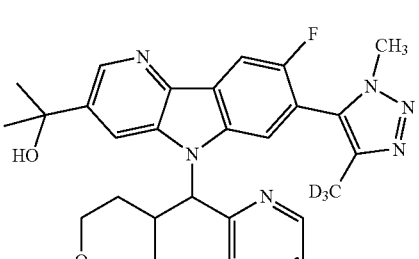 | 54 | 532.4 | B |
| 58 Enantiomer A | 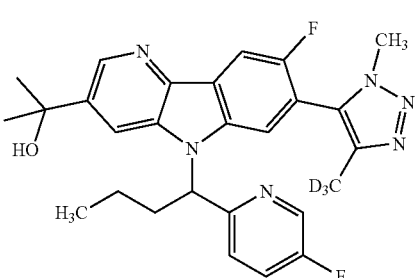 | 9.52 | 294.3 | G |

TABLE 2-continued
| Example | Structure | HPLC $T_R$ (min) | LC/MS (M + H) | HPLC Method |
|---|---|---|---|---|
| 59 Enantiomer B | 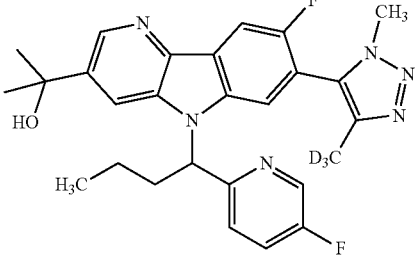 | 11.24 | 494.3 | G |
| 60 racemate | 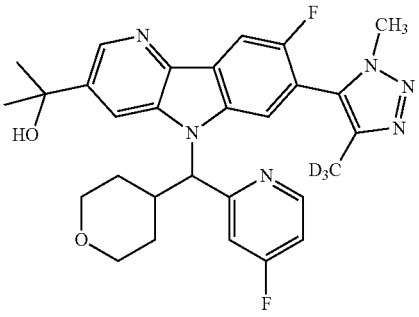 [SMILES: [2H]C([2H])([2H])c1nnn(C)c1-c1cc2c(cc1F)c1ncc(C(C)(C)O)cc1n2C(c1cc(F)ccn1)C1CCOCC1] | 2.79 | 536.6 | I |
| 61 racemate | 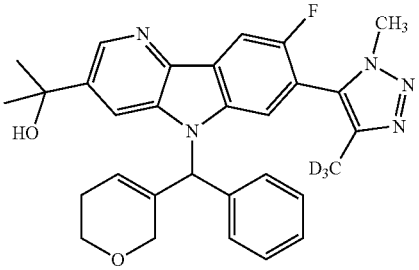 [SMILES: [2H]C([2H])([2H])c1nnn(C)c1-c1cc2c(cc1F)c1ncc(C(C)(C)O)cc1n2C(C1=CCCOC1)c1ccccc1] | 1.31 | 515.3 | J |
| 62 Enantiomer A | 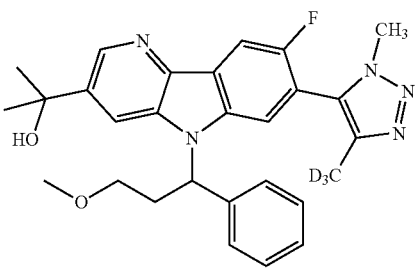 [SMILES: [2H]C([2H])([2H])c1nnn(C)c1-c1cc2c(cc1F)c1ncc(C(C)(C)O)cc1n2C(CCOC)c1ccccc1] | 8.96 | 491.30 | K |
| 63 Enantiomer A | 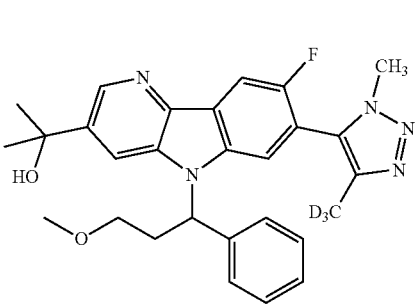 [SMILES: [2H]C([2H])([2H])c1nnn(C)c1-c1cc2c(cc1F)c1ncc(C(C)(C)O)cc1n2C(CCOC)c1ccccc1] | 12.62 | 491.30 | K |

TABLE 2-continued

| Example | Structure | HPLC T$_R$ (min) | LC/MS (M + H) | HPLC Method |
|---|---|---|---|---|
| 64 Enantiomer A | 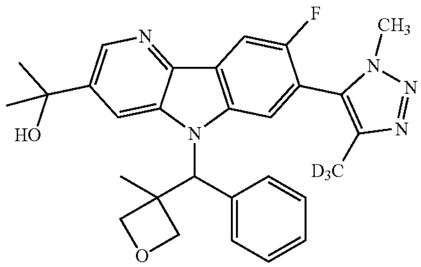 [SMILES: [2H]C([2H])([2H])c1nnn(C)c1-c1cc2c(cc1F)c1ncc(C(C)(C)O)cc1n2C(c1ccccc1)C1(C)COC1] | 19.59 | 503.2 | F |
| 65 Enantiomer A | 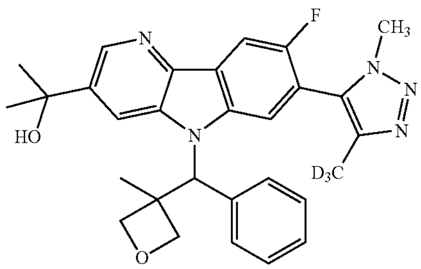 [SMILES: [2H]C([2H])([2H])c1nnn(C)c1-c1cc2c(cc1F)c1ncc(C(C)(C)O)cc1n2C(c1ccccc1)C1(C)COC1] | 24.35 | 503.2 | F |
| 66 racemate | 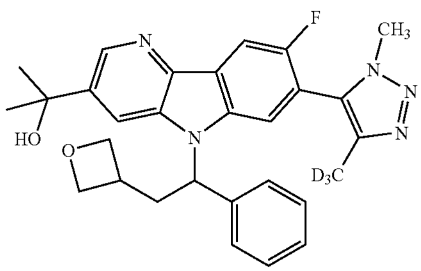 [SMILES: [2H]C([2H])([2H])c1nnn(C)c1-c1cc2c(cc1F)c1ncc(C(C)(C)O)cc1n2C(CC1COC1)c1ccccc1] | 1.22 | 503.2 | J |
| 67 Enantiomer A | 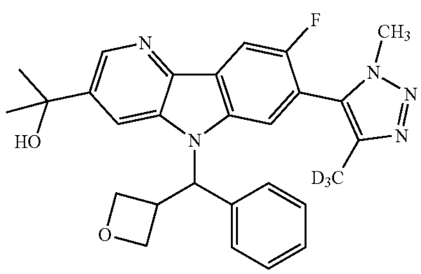 [SMILES: [2H]C([2H])([2H])c1nnn(C)c1-c1cc2c(cc1F)c1ncc(C(C)(C)O)cc1n2C(c1ccccc1)C1COC1] | 9.43 | 489.2 | E |
| 68 Enantiomer A | 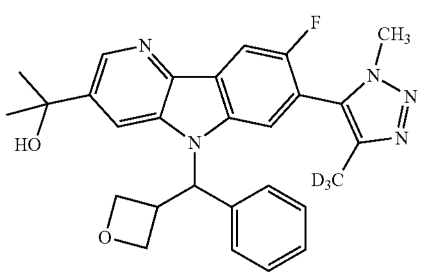 [SMILES: [2H]C([2H])([2H])c1nnn(C)c1-c1cc2c(cc1F)c1ncc(C(C)(C)O)cc1n2C(c1ccccc1)C1COC1] | 16.46 | 489.2 | E |

TABLE 2-continued

| Example | Structure | HPLC $T_R$ (min) | LC/MS (M + H) | HPLC Method |
|---|---|---|---|---|
| 69 Enantiomer A | 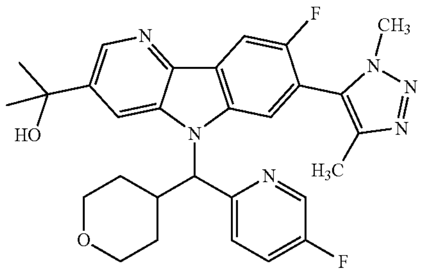 [SMILES: Cc1nnn(C)c1-c1cc2c(cc1F)c1ncc(C(C)(C)O)cc1n2C(c1ccc(F)cn1)C1CCOCC1] | 14.3 | 533.30 | L |
| 70 Enantiomer B | 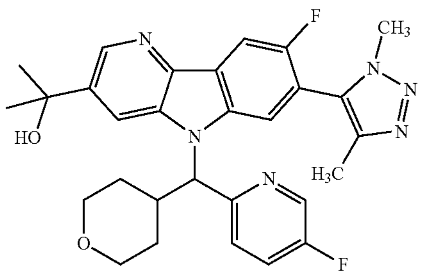 | 28.5 | 533.30 | L |

HPLC Conditions for Table 2: Method A: Column: Chiralcel OD 21×250 mm 10u; Mobile Phase A: 100% heptane; Mobile Phase B: 100% ethanol; Gradient: 12% B; Flow: 15 mL/min. Method B: Column: Chiralcel OD 21×250 mm 10u; Mobile Phase A: 100% heptane; Mobile Phase B: 100% ethanol; Gradient: 7% B; Flow: 15 mL/min. Method C: Column: Chiralcel OJ 21×250 mm 10u; Mobile Phase A: heptane with 0.1% diethylamine; Mobile Phase B: 100% ethanol; Gradient: 15% B; Flow: 15 mL/min. Method D: Column: Chiralpak AD 21×250 mm 5u; Mobile Phase A: 100% heptane; Mobile Phase B: 100% ethanol; Gradient: 10% B; Flow: 15 mL/min. Method E: Column: Chiralcel OD 21×250 mm 10u; Mobile Phase A: 100% heptane; Mobile Phase B: 100% ethanol; Gradient: 30% B; Flow: 15 mL/min. Method F: Column: Chiralcel OD 21×250 mm 10u; Mobile Phase A: 100% heptane; Mobile Phase B: 100% ethanol; Gradient: 20% B; Flow: 15 mL/min. Method G: Column: Chiralcel OD 21×250 mm 10u; Mobile Phase A: 100% heptane; Mobile Phase B: 100% ethanol; Gradient: 15% B; Flow: 15 mL/min. Method H: Column: Chiralpak AD-H 30×250 mm 5u; Mobile Phase: 10% MeOH in $CO_2$, 150 bar; Flow: 70 mL/min; Temperature: 35° C. Method I: Column: Phenomenex $C_{18\ 2}$×50 mm 3u; Mobile Phase A: 90% water and 10% acetonitrile with 0.1% TFA; Mobile Phase B: 10% water and 90% acetonitrile with 0.1% TFA; Gradient: 0-100% B over 4 min; Flow: 0.8 mL/min. Method J: Column: Phenomenex 2×30 mm 3u; Mobile Phase A: 90% water and 10% acetonitrile with 0.1% TFA; Mobile Phase B: 10% water and 90% acetonitrile with 0.1% TFA; Gradient: 0-100% B over 2 min; Flow: 1 mL/min. Method K: Column: Chiralpak AD 21×250 mm 5u; Mobile Phase A: 100% heptane; Mobile Phase B: 100% ethanol; Gradient: 20% B; Flow: 15 mL/min. Method L: Column: Chiralcel OJ 21×250 mm 10u; Mobile Phase A: 100% heptane; Mobile Phase B: 100% ethanol; Gradient: 18% B; Flow: 15 mL/min.

Examples 71 & 72

2-{5-[(3-Fluoropyridin-2-yl)(oxan-4-yl)methyl]-7-[4-($^2H_3$)methyl-1-methyl-1H-1,2,3-triazol-5-yl]-5H-pyrido[3,2-b]indol-3-yl}propan-2-ol

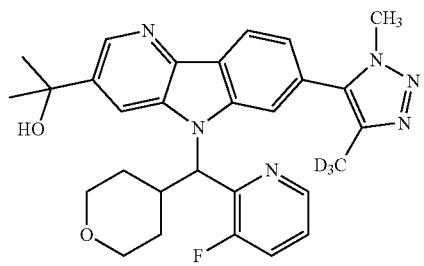

Enantiomer A, Example 71

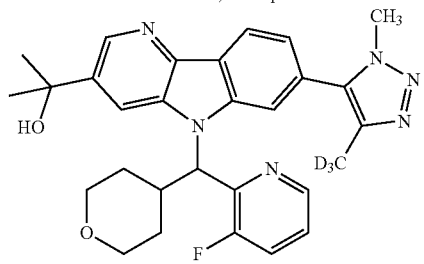

Enantiomer B, Example 72

Step 1: 5-Bromo-2-(4-chlorophenyl)-3-nitropyridine

Tripotassium phosphate (4.11 g, 19.4 mmol) was added to a stirred solution of (4-chlorophenyl)boronic acid (1.51 g, 9.7 mmol) and 2,5-dibromo-3-nitropyridine (3.00 g, 10.6 mmol) in THF (24 mL) and water (8 mL) at ambient temperature. The reaction mixture was degassed using $N_2$ (g) for 3 min before PdCl$_2$(dppf) (0.71 g, 0.97 mmol) was added in a single portion. The reaction mixture was subsequently heated to 80° C. for 16 h. The reaction mixture was diluted with water (10 mL) and ethyl acetate (20 mL), and the layers were separated. The aqueous layer was subsequently extracted with ethyl acetate (2×20 mL). The combined organics were dried over sodium sulfate. The solids were removed by filtration, the volatiles removed, and the crude material loaded onto a silica gel column. 5-Bromo-2-(4-chlorophenyl)-3-nitropyridine (2.15 g, 6.9 mmol, 71% yield) was purified using ethyl acetate in hexanes (0-30%). LC/MS (M+H)=313.00; LC/MS RT=1.895 min (Column: Phenomenex Luna 30×2.0 MM 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: 3-Bromo-7-chloro-5H-pyrido[3,2-b]indole

5-Bromo-2-(4-chlorophenyl)-3-nitropyridine (2.15 g, 6.9 mmol) and DPPE (3.42 g, 8.6 mmol) in 1,2-dichlorobenzene (23 mL) were heated to 170° C. under N$_2$ (g) for 16 h. The crude material was loaded directly onto a silica gel column, and the products were purified using ethyl acetate in hexanes (0-100%). 3-Bromo-7-chloro-5H-pyrido[3,2-b]indole (1.40 g, 5.0 mmol, 73% yield) was isolated as a yellow solid. LC/MS (M+H)=281.05; LC/MS RT=1.583 min (Column: Phenomenex Luna 30×2.0 MM 3u; Mobile Phase A: 10:90 acetonitrile:water with 0.1% TFA; Mobile Phase B: 90:10 acetonitrile: water with 0.1% TFA; Temperature: 40° C.; Gradient: 0-100% B over 2 min; Flow: 1 mL/min).

Step 3: 3-Bromo-7-chloro-5-((3-fluoropyridin-2-yl)(tetrahydro-2H-pyran-4-yl)methyl)-5H-pyrido[3,2-b]indole Racemic 3-bromo-7-chloro-5-((3-fluoropyridin-2-yl)(tetrahydro-2H-pyran-4-yl)methyl)-5H-pyrido[3,2-b]indole (229 mg, 0.48 mmol, 136% yield, colorless oil, isolated as a mixture with triphenylphosphine oxide impurity) was prepared from 3-bromo-7-chloro-5H-pyrido[3,2-b]indole and (3-fluoropyridin-2-yl)(oxan-4-yl)methanol according to Step 1 in route to 2-{8-fluoro-7-[4-($^2$H$_3$)methyl-1-methyl-1H-1,2,3-triazol-5-yl]-5-[(S)-(oxan-4-yl)(phenyl)methyl]-5H-pyrido[3,2-b]indol-3-yl}propan-2-ol. LC/MS (M+H)=474.05; LC/MS RT=2.085 min (Column: Phenomenex Luna 30×2.0 MM 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 4: 1-(7-Chloro-5-((3-fluoropyridin-2-yl)(tetrahydro-2H-pyran-4-yl)methyl)-5H-pyrido[3,2-b]indol-3-yl)ethanone Racemic 1-(7-chloro-5-((3-fluoropyridin-2-yl)(tetrahydro-2H-pyran-4-yl)methyl)-5H-pyrido[3,2-b]indol-3-yl)ethanone (107 mg, 0.25 mmol, 69% yield) was prepared from 3-bromo-7-chloro-5-((3-fluoropyridin-2-yl)(tetrahydro-2H-pyran-4-yl)methyl)-5H-pyrido[3,2-b]indole according to Step 2 in route to 2-{8-fluoro-7-[4-($^2$H$_3$)methyl-1-methyl-1H-1,2,3-triazol-5-yl]-5-[(S)-(oxan-4-yl)(phenyl)methyl]-5H-pyrido[3,2-b]indol-3-yl}propan-2-ol. LC/MS (M+H)=438.15; LC/MS RT=1.737 min (Column: Phenomenex Luna 30×2.0 MM 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 5: 1-{5-[(3-Fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}ethan-1-one Racemic 1-{5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}ethan-1-one was prepared from 1-(7-chloro-5-((3-fluoropyridin-2-yl)(tetrahydro-2H-pyran-4-yl)methyl)-5H-pyrido[3,2-b]indol-3-yl)ethanone and 4-($^2$H$_3$)methyl-1-methyl-5-(tributylstannyl)-1H-1,2,3-triazole (prepared in route to 2-{8-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol) according to Step 3 in route to 2-{8-fluoro-7-[4-($^2$H$_3$)methyl-1-methyl-1H-1,2,3-triazol-5-yl]-5-[(S)-(oxan-4-yl)(phenyl)methyl]-5H-pyrido[3,2-b]indol-3-yl}propan-2-ol. LC/MS RT=1.406 min (Column: Phenomenex Luna 30×2.0 MM 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 6: 2-{5-[(3-Fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol Enantiomers A and B of 2-{5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol were prepared according to Step 10 in route to 2-{8-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol. Enantiomers A and B were separated using chiral preparative HPLC (Column: Chiralcel OD 21×250 mm 10u; Mobile Phase: 15% ethanol in heptane with 0.1% diethylamine; Flow: 15 mL/min). The first eluting enantiomer (14.10 min) was defined as Enantiomer A (1.5 mg, 1% yield), and the second eluting enantiomer (20.05 min) was defined as Enantiomer B (1.3 mg, 1% yield). $^1$H NMR (500 MHz, DMSO-d$_6$) δ 8.66 (br. s., 1H), 8.61 (d, J=4.77 Hz, 1H), 8.41 (br. s., 1H), 8.30 (d, J=8.07 Hz, 1H), 7.69 (t, J=9.17 Hz, 1H), 7.49 (td, J=4.31, 8.25 Hz, 1H), 7.36 (d, J=8.07 Hz, 1H), 6.20 (br. s., 1H), 5.34 (br. s., 1H), 4.04 (br. s., 3H), 3.87 (d, J=8.44 Hz, 1H), 3.69 (d, J=10.64 Hz, 1H), 3.37-3.54 (m, 2H), 3.13-3.22 (m, 1H), 1.68-1.77 (m, 1H), 1.44-1.68 (m, 7H), 1.33 (d, J=10.27 Hz, 1H), 0.68 (d, J=11.74 Hz, 1H). LC/MS (M+H)=518.25; LC/MS RT=1.188 min (Column: Phenomenex Luna 30×2.0 MM 3u; Mobile Phase A: 10:90 acetonitrile:water with 0.1% TFA; Mobile Phase B: 90:10 acetonitrile: water with 0.1% TFA; Temperature: 40° C.; Gradient: 0-100% B over 2 min; Flow: 1 mL/min).

Examples 73 & 74

The compounds in Table 3 were prepared from commercially available starting materials or intermediates prepared according to analogous procedures described for 2-{5-[(3-Fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol:

TABLE 3

| Example | Structure | HPLC T$_R$ (min) | LC/MS (M + H) | HPLC Method |
|---|---|---|---|---|
| 73 Enantiomer A | 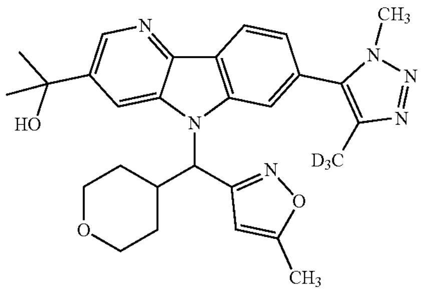 [SMILES: [2H]C([2H])([2H])c1nnn(C)c1-c1ccc2c3ncc(C(C)(C)O)cc3n(C(c3cc(C)on3)C3CCOCC3)c2c1] | 29 | 504.3 | A |
| 74 Enantiomer B | 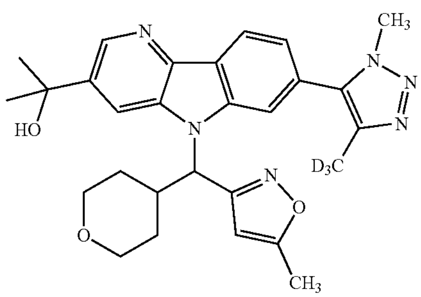 [SMILES: [2H]C([2H])([2H])c1nnn(C)c1-c1ccc2c3ncc(C(C)(C)O)cc3n(C(c3cc(C)on3)C3CCOCC3)c2c1] | 36 | 504.3 | A |

HPLC Conditions for Table 3: Method A: Column: Chiralcel OD 21×250 mm 10u; Mobile Phase A: heptanes with 0.1% diethylamine; Mobile Phase B: 100% ethanol; Gradient: 10% B; Flow: 15 mL/min.

Examples 75 & 76

2-{8-Chloro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol

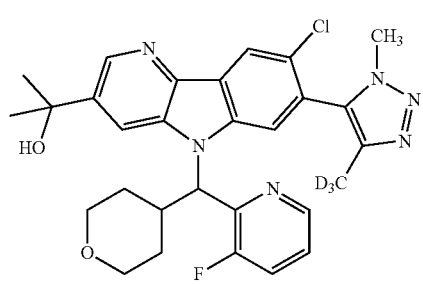

Enantiomer A, Example 75

-continued

Enantiomer B, Example 76

Step 1: 2-{8-Chloro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol Racemic 2-{5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol (22.0 mg, 43 μmol) and NCS (7.4 mg, 55 μmol) were stirred in DMF (213 μL) at 70° C. under N$_2$ (g) for 4 h. The crude material was purified via preparative LC/MS with the following conditions: Column: XBridge C18, 19×200 mm, 5-μm particles; Mobile Phase A: 5:95 acetonitrile: water with 10-mM ammonium acetate;

Mobile Phase B: 95:5 acetonitrile: water with 10 mM ammonium acetate; Gradient: 25-65% B over 15 min, then a 5-min hold at 100% B; Flow: 20 mL/min. Fractions containing the desired product were combined and dried via centrifugal evaporation to afford racemic 2-{8-chloro-5-[(3-fluoropyridin-2-yl)(oxan-4-yl)methyl]-7-[4-($^{2}H_3$)methyl-1-methyl-1H-1,2,3-triazol-5-yl]-5H-pyrido[3,2-b]indol-3-yl}propan-2-ol. Enantiomers A and B were separated using chiral preparative HPLC (Column: Chiralpak OD 21×250 mm 10u; Mobile Phase: 10% ethanol in heptane with 0.1% diethylamine; Flow: 15 mL/min). The first eluting enantiomer (19.17 min) was defined as Enantiomer A (2.7 mg, 12% yield), and the second eluting enantiomer (26 min) was defined as Enantiomer B (2.5 mg, 10% yield). $^{1}$H NMR (500 MHz, DMSO-$d_6$) δ 8.70 (br. s., 1H), 8.63-8.56 (m, 1H), 8.42 (br. s., 1H), 8.36 (d, J=2.6 Hz, 1H), 7.74-7.65 (m, 1H), 7.49 (dd, J=7.7, 3.7 Hz, 1H), 6.20 (d, J=10.3 Hz, 1H), 5.35 (br. s., 1H), 3.94-3.78 (m, 4H), 3.70 (d, J=10.3 Hz, 1H), 3.52-3.36 (m, 2H), 3.25-3.14 (m, 1H), 1.73-1.47 (m, 7H), 1.34 (d, J=8.8 Hz, 1H), 1.16 (t, J=7.3 Hz, 1H), 0.75-0.65 (m, 1H). LC/MS (M+H)=552.25; LC/MS RT=1.341 min (Column: Phenomenex Luna 30×2.0 MM 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Examples 77-83

The compounds in Table 4 were prepared from commercially available starting materials or intermediates prepared according to analogous procedures described for 2-{8-chloro-5-[(3-fluoropyridin-2-yl)(oxan-4-yl)methyl]-7-[4-($^{2}H_3$)methyl-1-methyl-1H-1,2,3-triazol-5-yl]-5H-pyrido[3,2-b]indol-3-yl}propan-2-ol:

TABLE 4

| Example | Structure | HPLC $T_R$ (min) | LC/MS (M + H) | HPLC Method |
|---|---|---|---|---|
| 77 | 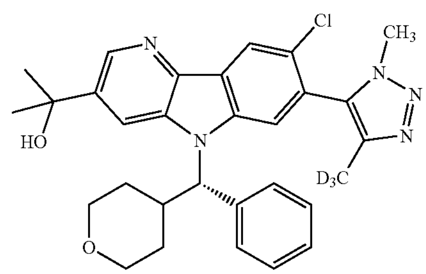 [SMILES: [2H]C([2H])([2H])c1nnn(C)c1-c1cc2c(cc1Cl)c1ncc(C(C)(C)O)cc1n2[C@H](c1ccccc1)C1CCOCC1] | 1.41 | 533.3 | A |
| 78 Enantiomer A | 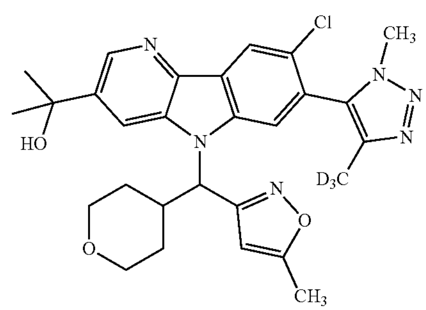 [SMILES: [2H]C([2H])([2H])c1nnn(C)c1-c1cc2c(cc1Cl)c1ncc(C(C)(C)O)cc1n2C(c1cc(C)on1)C1CCOCC1] | 16 | 538.3 | B |
| 79 Enantiomer B | 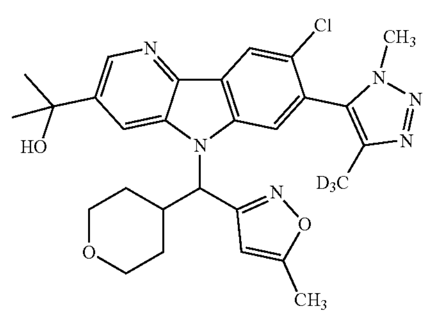 [SMILES: [2H]C([2H])([2H])c1nnn(C)c1-c1cc2c(cc1Cl)c1ncc(C(C)(C)O)cc1n2C(c1cc(C)on1)C1CCOCC1] | 27 | 538.3 | B |

TABLE 4-continued

| Example | Structure | HPLC T$_R$ (min) | LC/MS (M + H) | HPLC Method |
|---|---|---|---|---|
| 80 Enantiomer A | 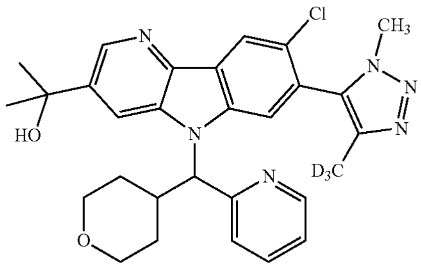 [SMILES: [2H]C([2H])([2H])c1nnn(C)c1-c1cc2c(cc1Cl)c1ncc(C(C)(C)O)cc1n2C(c1ccccn1)C1CCOCC1] | 17.28 | 534.3 | C |
| 81 Enantiomer B | 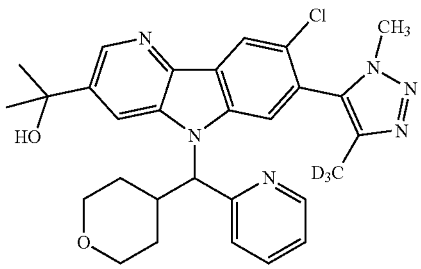 [SMILES: [2H]C([2H])([2H])c1nnn(C)c1-c1cc2c(cc1Cl)c1ncc(C(C)(C)O)cc1n2C(c1ccccn1)C1CCOCC1] | 23.8 | 534.3 | C |
| 82 Enantiomer A | 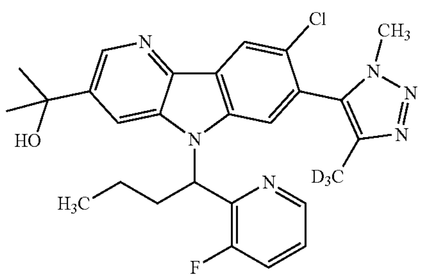 [SMILES: [2H]C([2H])([2H])c1nnn(C)c1-c1cc2c(cc1Cl)c1ncc(C(C)(C)O)cc1n2C(CCC)c1ncccc1F] | 6.50 | 510.2 | D |
| 83 Enantiomer B | 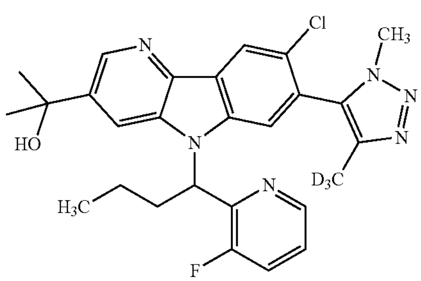 | 8.30 | 510.2 | D |

HPLC Conditions for Table 4: Method A: Column: Phenomenex Luna 30×2.0 MM 3u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min. Method B: Column: Chiralcel OJ 21×250 mm 10u; Mobile Phase A: heptane with 0.1% diethylamine; Mobile Phase B: 100% ethanol; Gradient: 15% B; Flow: 15 mL/min. Method C: Column: Chiralcel OD 21×250 mm 10u; Mobile Phase A: heptane with 0.1% diethylamine; Mobile Phase B: 100% ethanol; Gradient: 10% B; Flow: 15 mL/min. Method D: Column: Chiralpak AD-H 30×250 mm 5u; Mobile Phase: 15% MeOH in $CO_2$, 150 bar; Flow: 70 mL/min; Temperature: 35° C.

Examples 84 & 85

2-{6-Fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol

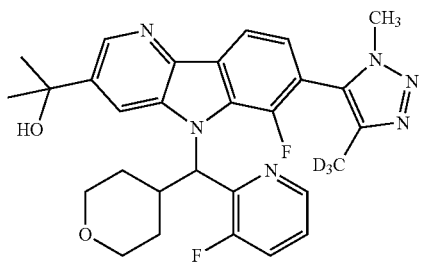

Enantiomer A, Example 84

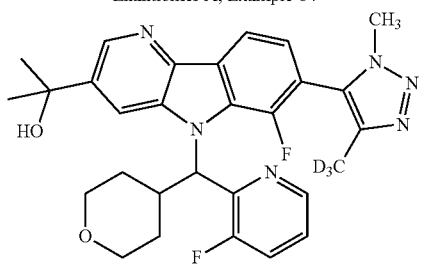

Enantiomer B, Example 85

Step 1: 2-{6-Fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol Racemic 2-{6-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol was prepared from 3-bromo-7-chloro-6-fluoro-5H-pyrido[3,2-b]indole according to the procedures described in route to 2-{8-fluoro-5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol. Enantiomers A and B were separated using chiral preparative HPLC (Column: Chiralpak AD 21×250 mm 10u; Mobile Phase: 20% ethanol in heptane; Flow: 15 mL/min). The first eluting enantiomer (9.98 min) was defined as Enantiomer A (1.1 mg, 2% yield), and the second eluting enantiomer (14 min) was defined as Enantiomer B (1.9 mg, 3% yield). $^1$H NMR (500 MHz, DMSO-d$_6$) δ 8.67 (br. s., 1H), 8.61 (br. s., 1H), 8.38 (br. s., 1H), 8.16 (d, J=8.1 Hz, 1H), 7.74-7.64 (m, 1H), 7.56-7.44 (m, 1H), 7.41-7.30 (m, 1H), 6.37-6.25 (m, 1H), 3.99 (br. s., 3H), 3.87 (d, J=13.6 Hz, 1H), 3.75 (d, J=11.0 Hz, 1H), 3.53-3.46 (m, 1H), 3.23 (t, J=11.7 Hz, 1H), 3.17 (d, J=4.4 Hz, 1H), 1.86-1.73 (m, 1H), 1.50 (d, J=9.5 Hz, 6H), 1.41-1.27 (m, 2H), 0.86 (d, J=13.2 Hz, 1H). LC/MS (M+H) =536.3; LC/MS RT=2.39 min (Column: Phenomenex Luna 50×2.0 MM 3u; Mobile Phase A: 10:90 acetonitrile:water with 0.1% TFA; Mobile Phase B: 90:10 acetonitrile: water with 0.1% TFA; Temperature: 40° C.; Gradient: 0-100% B over 4 min; Flow: 0.8 mL/min).

Evaluation of Biological Activity

Exemplary compounds were tested for inhibition of BRD2, BRD3, BRD4 and BRDT activity. Experimental procedures and results are provided below. Cloning, Expression, and Purification of Human Bromodomains for Thermal Shift Assays (TSA)

Recombinant DNA clones encoding bromodomains of human proteins were optimized for E. coli expression, chemically synthesized (GenScript, Piscataway N.J.), and inserted into a modified pET28 expression vector to construct tobacco vein mottling virus (TVMV) protease cleavable N-terminal hexahistidine fusions. The non-native amino acids (MGSSHHHHHHSSGETVRFQSM) (SEQ ID NO: 1) were immediately followed by bromodomain proteins with the amino acid residue sequences (followed by accessions referenced from and numbered according to the Uniprot Knowledgebase; Uniprot Consortium; www.uniprot.org) as follows:

CECR2(420-543), Q9BXF3-1; FALZ(2917-3037), Q12830-1; GCN5(731-837), Q92830-1; PCAF(715-831), Q92831-1; BRD2(24-472), P25440-1; BRD3(1-434), Q15059-1; BRD4(44-168), BRD4(333-460), BRD4(44-460), O60885-1; BRDT(1-383), Q58F21-1; BAZ1B(1340-1457), Q9UIG0-1; CREBBP(1081-1197), Q92793-1; EP300(1040-1161), Q09472-1; WDR9(1310-1430), Q9NSI6-1; ATAD2(981-1108), Q6PL18-1; BRD1(556-688), O95696-1; BRD7(129-236), Q9NPI1-1; BRD9(134-239), Q9H8M2-1; BRPF1(626-740), P55201-2; ATAD2B(952-1086), Q9ULI0-1; BAZ2B(2054-2168), Q9UIF8-1; 5P140L(400-580), Q9H930-4; 5P140(687-862), Q13342-1; TIF1(896-1014), O15164-1; TRIM28(619-805), Q13263-1; BRWD3(1295-1443), Q6R145-1; TAF1(1377-1503), TAF1(1501-1635), P21675-1; TAF1L(1402-1522), TAF1L(1523-1654), Q8IZX4-1; ASH1L(2433-2564), Q9NR48-1; PB1(43-156), PB1(178-291), PB1(388-494), PB1(645-766), PB1(773-917), Q86U86-1; SMARCA2(1367-1511), P51531-1; SMARCA2-2(1367-1493), P51531-2.

The recombinant vectors were transformed into E. coli BL21(DE3). The transformed cells were cultured in 1 L terrific broth in 2.5 L Thomson Ultra Yield shaker flasks at 37° C., 230 rpm and, at a cell density of OD600 nm=1.0, were induced with 0.5 mM IPTG and incubated in the shaker at 20° C. for 16-18 hours. The cell pellets were harvested by sedimentation and lysed by sonication in buffer containing 0.1 mg/ml lysozyme. Each sample was clarified by sedimentation, and the supernatant was loaded onto a HisTrap affinity column (GE Healthcare Life Sciences). The column was washed and then eluted with an imidazole gradient. The peak protein fractions containing the bromodomain protein were pooled, concentrated, and the protein was purified further by size exclusion chromatography on a Superdex 200 column (GE Healthcare Life Sciences) equilibrated with the final storage buffer (20 mM Tris-HCl pH 8.0, 200 mM NaCl, 5% glycerol, 2 mM DTT). The SEC peak fractions containing purified protein at 2-5 mg/ml were pooled, and the pool was divided into aliquots, flash frozen in liquid nitrogen, and store at −80° C.

Cloning, Expression, and Purification of Biotinylated Human Bromodomains for TR-FRET Assays Recombinant DNA clones encoding bromodomains of human BRD2, BRD3, BRD4 and BRDT were optimized for E. coli expression, chemically synthesized (GenScript, Piscataway N.J.), and inserted into a modified pET28 expression vector to construct tobacco vein mottling virus (TVMV) protease cleavable N-terminal hexahistidine fusions followed by a site specific biotinylation motif recognized by E. coli biotin ligase (BirA). The non-native amino acids (MGSSHHHHHHSSGETVRFQGLNDIFEAQKIEWHEDTGHM) (SEQ ID NO: 2) were immediately followed by bromodomain constructs of BRD4 with the amino acid residue sequences (followed by the BRD4 accession referenced from and numbered according to the Uniprot Knowledgebase; Uniprot Consortium; www.uniprot.org) as follows: BRD4(44-168), BRD4(333-460), BRD4 (44-460), BRD4(1-477), O60885-1.

Each of the recombinant vectors were co-transformed into *E. coli* BL21 STAR (DE3) together with a plasmid encoding BirA under chloramphenicol selection. The transformed cells were cultured at 37° C. in 2.5 L Thomson Ultra Yield shaker flasks containing 1 L M9-CAS medium (Teknova) supplemented with 40 µg/ml kanamycin, 35 µg/ml chloramphenicol, and 100 µM biotin. At a cell density corresponding to an OD600 nm=0.6, the cultures were induced with 0.5 mM IPTG and incubated in the shaker for an additional 20 hours at 20° C. The cell pellets were harvested by sedimentation and lysed by sonication in buffer containing 0.1 mg/ml lysozyme. Each sample was clarified by sedimentation, and the supernatant was loaded onto a HisTrap affinity column. The column was washed and then eluted with an imidazole gradient. The peak protein fractions containing the bromodomain protein were pooled and incubated for 18 hours at 4° C. with purified His-TVMV protease (1:15 mass ratio of TVMV:BRD4 protein). The sample was exchanged into low imidazole buffer and passed through a HisTrap column to capture the cleaved His-tag and His-TVMV enzyme. The protein in the HisTrap column flow through was further purified and exchanged into the final storage buffer (PBS pH 7.0, 5% Glycerol, 1 mM DTT) by size exclusion chromatography on a Superdex 200 column. To improve purity, the BRD4(1-477) and BRD4(44-460) proteins were subjected to an additional cation exchange chromatography purification step prior to size exclusion chromatography. Essentially quantitative mono-biotinylation (+226 Da) of each protein was confirmed by electrospray ionization mass spectrometry analysis on the final sample. The purified samples were divided into aliquots, flash frozen in liquid nitrogen, and stored at −80° C.

Time Resolved Fluorescence Resonance Energy Transfer (TR-FRET) Assay

The binding of compounds to bromodomain BRD4 (44-168), BRD4 (333-460), and BRD4 (1-477 or 44-460) was assessed using a time resolved fluorescent resonance energy transfer binding assay (1), that measures the binding of a fluorescently labeled probe molecule to the bromodomain protein. The bromodomain protein, fluorescent probe molecule (either a biotinylated histone peptide or a fluorescently labeled small molecule), and dose-responsed test compound are incubated together to reach thermodynamic equilibrium. In the absence of a test compound, the bromodomain and small molecule are bound, resulting in a high fluorescent signal. In the presence of a sufficient concentration of inhibitor, this intercation is disrupted resulting in a lost of fluorescent resonance energy transfer.

All assay components were dissolved in buffer composition 20 mM Hepes pH 7.5, 150 mM NaCl, 5 mM DTT, 0.005% Tween 20, and 100 ug/ml BSA for BRD4 (1-477 and 44-460). The final concentrations of the bromodomain proteins are 1.6 nM BRD4(44-168), 1 nM BRD4(333-460), and 1 nM BRD4(1-477 or 44-460), and the fluorescent probe molecule is 100 nM, 50 nM, and 7.5 nM respectively. All proteins were biotinylated. A streptavidin labeled with terbium cryptate (Cisbio SA-Tb) was used as detection, and pre-mixed with the bromodomain protein at a final concentration of 0.2 nM. In some instances for BRD4 (44-460), anti-His terbium cryptate was used as a detection. 7.5 nl of dose-responsed test compound or dmso vehicle (0.0375%) was pre-spotted in a black Corning 384 well plate and 10 ul each of bromodomain/detection reagent and fluorescent small molecule solution were added to the plate, and the reaction incubated for 60 min at room temperature. Plates were then read on EnVision plate reader, ($\lambda$ex=340 nm, acceptor $\lambda$Em=520 nm, and donor $\lambda$Em=615 nm, LANCE D400 mirror). Time resolved fluorescence intensity measurements were made at both emissions, and the ratio of acceptor/donor was calculated and used for data analysis. All data was normalized to 16 high vehicle wells and 8 low reference control wells, and then a four parameter curve fit was applied:

$$Y=a+((b-a)/(1+(10x/10c)d)$$

Where 'a' is the minimum, 'b' is the Hill slope, 'c' is the IC50, and 'd' is the maximum. Histone peptide: Purchased from GenScript H4K5K8K12K16
(SEQ ID NO: 3)
Biotin-AHA-SGRGK(Ac)GGK(Ac)GLGK(Ac)GGAK(Ac)RHRKV The fluorescently labeled small molecule used was a BRD4 inhibitor known in the art 1. F. Degorce, A. Card, S. Soh, E. Trinquet, G. P. Knapik and B. Xie, HTRF: A technology tailored for drug discovery a review of theoretical aspects and recent applications. Current Chemical Genomics (2009) 3, 22-32

Thermal Shift Assay

The effect of compound binding on the thermal stability of the bromodomains was measured using a BioRad CFX real time PCR instrument by monitoring the fluorescence enhancement of an external probe (SYPRO orange) as it binds preferentially to the unfolded protein. The unfolding reactions were carried out in a 384-well plate in a 4 uL volume with 2-8 uM of bromodomain protein, 1-2% (v/v) DMSO in buffer containing 10 mM Hepes, pH 7.4, 500 mM NaCl. SYPRO orange dye was added at a dilution of 1:500. Compound concentrations ranged from 1.6-100 uM. Unfolding reactions were monitored by first equilibrating the instrument at 25° C. for 2.4 sec, followed by ramping the temperature in 0.5° C. increments from 25 to 95° C. with 60 s equilibration prior to a read at each temperature. Excitation and emission filters for the SYPRO orange dye were set to FRET with the excitation range from 450-490 nm and the emission range from 560-580 nm. The midpoint temperature was determined by calculating the inflection point using the second derivative. The observed temperature shifts were recorded as the difference between the midpoint between a reference well containing protein with dmso but no ligand and a well containing protein with compound.

The thermal shift assay is a biophysical technique that compares the change in unfolding transition temperature of a protein obtained in the presence and absence of a ligand (1). Typically, a fluorescent dye is used to monitor the protein unfolding as the protein is heated. During the unfolding process, hydrophobic regions of the protein are exposed, resulting in an increase in the dye binding and an increase in fluorescence intensity. The midpoint of the protein unfolding transition is defined as the Tm. A ligand that binds to the protein causes an increase in the protein thermal stability, thus increasing the Tm, proportionally to both the ligand concentration and its binding affinity.

1. M. W. Pantoliano, E. C. Petrella, J. D. Kwasnoski, V. S. Lobanov, J. Myslik, E. Graf, T. Carver, E. Asel, B. A. Springer, P. Lane, F. R. Salemme, High-density miniaturized thermal shift assays as a general strategy for drug discovery. J. Biomol. Screen 6(2001) 429-440.

2. M. D. Cummings, M. A. Farnum, M. I. Nelen, Universal screening methods and application of ThermoFluor. J. Biomol. Screen 11 (2006) 854-863

MYC HCS Assay

Tumor cells in complete RPMI growth media (Gibco, 11875-085) supplemented with 10% FBS were harvested and plated into 384 black clear-bottom PDL cell culture plates in 30 ul media with 10,000 cells per well. After compound treatment at 37 C for 4 hrs, cells were fixed in 4% Formaldehyde at room temperature for 30 min and subsequently permeabilized. After washing and blocking, the plates were then incubated with anti-myc primary antibody 1:1000 (Cell Signaling Technology, 5605) at RT overnight. The following day, cells were washed and blocked before adding secondary antibody Alexa 488 Goat-anti Rabbit 1:2000 (Invitrogen, A11034) at RT in the dark for 1 hr. Cells were subsequently washed and scanned on the Cellomics ArrayScan with 10× objective lens.

MTS Cell Proliferation Assay

Tumor cells were plated at certain seeding densities in 384-well black clear bottom Matrix plates at 40 ul per well and incubated overnight at 37° C. in 5% $CO_2$ before assaying. On the next day, one set of cell plates (T0 plates) were used to determine time zero cell density, and 3-(4,5-dimethylthiazol-2-yl)-5-(3-carboxymethoxyphenyl)-2-(4-sulfophenyl)-2H-tetrazolium from the CellTiter 96 AQueous Non-Radioactive Cell proliferation Kit (Promega, G5440) was added at 4 µl/well into T0 plates followed by incubation at 37° C. in 5% $CO_2$ for three hours. Absorbance at 490 nm was measured on an Envision reader (Perkin Elmer, Boston, Mass.). On the same day, the remaining cell plates (T72 plates) were treated with compounds at 37° C. in 5% $CO_2$. After 72 hours, 4 ul MTS reagents were then added onto those cell plates. The plates were further incubated at 37° C. in 5% $CO_2$ for three hours and the absorbance values at A490 were measured on an Envision reader.

Human Tumor Xenograft Models in Mice

All rodents were obtained from Jackson Laboratory. (Bar Harbor, Me.), and maintained in an ammonia-free environment in a defined and pathogen-free colony. All mice were quarantined approximately 1 week prior to their use for tumor propagation and drug efficacy testing. Mice were fed food and water ad libitum. The animal care program of Bristol-Myers Squibb Pharmaceutical Research Institute is fully accredited by the American Association for Accreditation of Laboratory Animal Care (AAALAC). All experiments were performed in accordance with Bristol-Myers Squibb (BMS) animal test methods and guidelines.

Tumor xenografts were grown and maintained subcutaneously (SC) in NSG (NOD scid IL2 receptor gamma chain knockout) mice (Jackson Lab). Tumors were propagated as subcutaneous transplants using tumor fragments obtained from donor mice.

Preclinical Chemotherapy Trials

The required numbers of animals needed to detect a meaningful response were pooled at the start of the experiment and each was given bilateral subcutaneous implants of two tumor fragments (~20 mg) with a 13-gauge trocar. Tumors were allowed to grow to the pre-determined size window (tumors outside the range were excluded) and animals were evenly distributed to various treatment and control groups. There were typically 6-8 mice per treatment and control groups, consisting of 10-12 tumors. Treatment of each animal was based on individual body weight. Treated animals were checked daily for treatment related toxicity/mortality. Each group of animals was weighed before the initiation of treatment ($Wt_1$) and then again following the last treatment dose ($Wt_2$). The difference in body weight ($Wt_2-Wt_1$) provides a measure of treatment-related toxicity.

Tumor response was determined by measurement of tumors with a caliper twice a week, until the tumors reached a predetermined "target" size of 0.5 gm or 1 gm depending on the tumor type. Tumor weights (mg) were estimated from the formula:

$$\text{Tumor weight} = (\text{length} \times \text{width}^2) \div 2$$

Tumor response criteria are expressed in terms of tumor growth inhibition (% TGI). Tumor growth delay is defined as the difference in time (days) required for the treated tumors (T) to reach a predetermined target size compared to those of the control group (C). For this purpose, the tumor weight of a group is expressed as medium tumor weight (MTW).

Tumor growth inhibition is calculated as follows:

$$\% \text{ Tumor Growth Inhibition} = \frac{\left(1 - \frac{T_t}{T_0} * \frac{C_0}{C_t}\right)}{\left(1 - \frac{C_0}{C_t}\right)}$$

where,
$C_t$=Median control tumor size at end of treatment
$C_0$=Median control tumor size at treatment initiation
$T_t$=Median tumor size of treated group at end of treatment
$T_0$=Median tumor size of treated group at treatment initiation Activity is defined as the achievement of durable tumor growth inhibition of 50% or greater (i.e. TGI≥50%) for a period equivalent to at least 1 tumor volume doubling time and drug treatment must be for a period equivalent to at least 2 tumor volume doubling time.

Tumor response was also expressed in terms of tumor growth delay and expressed as log cell kill (LCK value), defined as the difference in time (days) required for the treated tumors (T) to reach a predetermined target size compared to those of the control group (C).

Whenever possible, antitumor activity was determined at a range of dose levels up to the maximum tolerated dose (MTD) which is defined as the dose level immediately below which excessive toxicity (i.e. more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses. Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at $P<0.05$.

Drug Administration

For administration of BET inhibitors to rodents, compounds were dissolved in 90% PEG300/10% TPGS/10% Ethanol. BET inhibitors were typically administered orally on a schedule of QD×7 or QD×10 (5 day-on-2 day-off), although other schedules had also been evaluated and shown to be efficacious The activity data shown below is based on the use of one of the FRET assays described. Compounds with an $IC_{50}$ less than 1500 nM are shown with (+), compounds with an $IC_{50}$ less than 5 nM are shown with (++) and those with an $IC_{50}$ less than 1 nM are shown with (+++).

| Example # | FRET BRD4 $IC_{50}$ (nM) |
|---|---|
| Example 1 | + |
| Example 2 | + |
| Example 3 | +++ |
| Example 4 | ++ |
| Example 5 | ++ |
| Example 6 | ++ |
| Example 7 | ++ |
| Example 8 | +++ |
| Example 9 | ++ |
| Example 10 | ++ |
| Example 11 | +++ |
| Example 12 | ++ |
| Example 13 | +++ |
| Example 14 | ++ |
| Example 15 | ++ |
| Example 16 | ++ |
| Example 17 | ++ |
| Example 18 | ++ |
| Example 19 | + |
| Example 20 | ++ |
| Example 21 | +++ |
| Example 22 | +++ |
| Example 23 | ++ |
| Example 24 | ++ |
| Example 25 | +++ |
| Example 26 | ++ |
| Example 27 | ++ |
| Example 28 | +++ |
| Example 29 | ++ |
| Example 30 | +++ |
| Example 31 | ++ |
| Example 32 | +++ |
| Example 33 | +++ |
| Example 34 | +++ |
| Example 35 | + |
| Example 36 | +++ |
| Example 37 | ++ |
| Example 38 | +++ |
| Example 39 | ++ |
| Example 40 | + |
| Example 41 | ++ |
| Example 42 | ++ |
| Example 43 | ++ |
| Example 44 | + |
| Example 45 | ++ |
| Example 46 | ++ |
| Example 47 | ++ |
| Example 48 | + |
| Example 49 | ++ |
| Example 50 | ++ |
| Example 51 | + |
| Example 52 | ++ |
| Example 53 | + |
| Example 54 | ++ |
| Example 55 | + |
| Example 56 | ++ |
| Example 57 | + |
| Example 58 | NA |
| Example 59 | ++ |
| Example 60 | ++ |
| Example 61 | ++ |
| Example 62 | + |
| Example 63 | ++ |
| Example 64 | ++ |
| Example 65 | + |
| Example 66 | +++ |
| Example 67 | ++ |
| Example 68 | + |
| Example 69 | + |
| Example 70 | ++ |
| Example 71 | +++ |
| Example 72 | +++ |
| Example 73 | ++ |
| Example 74 | + |
| Example 75 | + |
| Example 76 | + |
| Example 77 | + |
| Example 78 | + |
| Example 79 | + |
| Example 80 | + |
| Example 81 | + |
| Example 82 | + |
| Example 83 | ++ |
| Example 84 | ++ |
| Example 85 | ++ |

NA = Not available

What is claimed is:

1. A compound of formula (II)

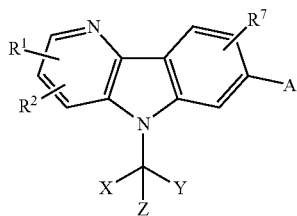

wherein:

A is

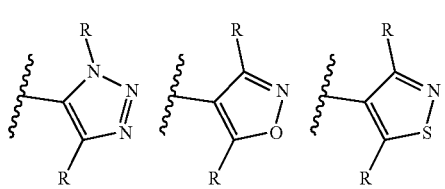

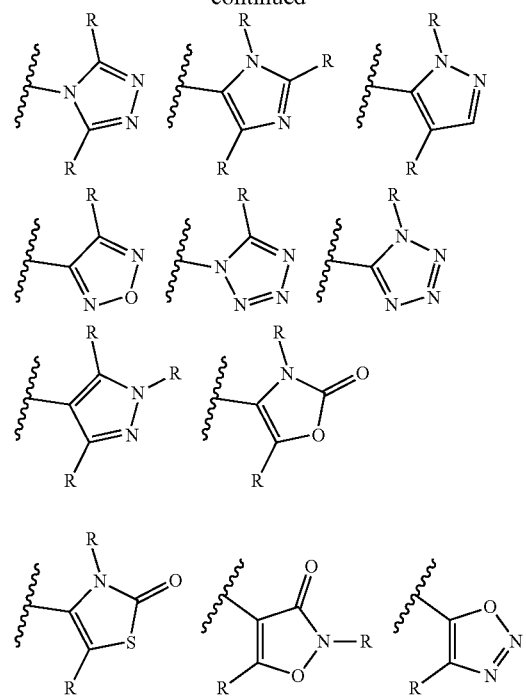

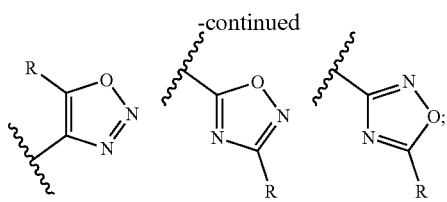

R is independently one or more hydrogen, CD$_3$, halogen, haloalkyl, hydroxyalkyl, CN, CF$_3$, CH$_2$F, CHF$_2$, optionally substituted (C$_1$-C$_6$)alkyl, optionally substituted (C$_1$-C$_6$)alkoxy, optionally substituted (C$_3$-C$_6$)cycloalkyl, —OR$^4$, —NR$^3$R$^4$, NR$^3$R$^4$(C$_1$-C$_6$)alkyl-, —NR$^6$OCOR$^3$, —NR$^6$COR$^3$, —NR$^6$CONR$^3$R$^4$;

X and Y are independently selected from optionally substituted (C$_1$-C$_6$)alkyl, optionally substituted (C$_3$-C$_8$)cycloalkyl, optionally substituted aryl, optionally substituted heteroaryl or optionally substituted heterocyclo;

Z is hydrogen, halogen, —OH, (C$_1$-C$_6$)alkyl or (C$_1$-C$_6$)alkoxy;

R$^1$ is hydrogen, halogen, —CN, —OR$^4$, —NR$^3$R$^4$, —CONR$^3$R$^4$, —COOH, —OCONR$^3$R$^4$, —NR$^6$OCOR$^3$, —NR$^6$CONR$^3$R$^4$, —NR$^6$SO$_2$NR$^3$R$^4$, —NR$^6$SO$_2$R$^4$, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkoxy, optionally substituted (C$_3$-C$_8$)cycloalkyl, optionally substituted (C$_3$-C$_8$)cycloalkyl (C$_1$-C$_6$)alkyl, optionally substituted (C$_3$-C$_8$)cycloalkyl-CO—, optionally substituted (C$_3$-C$_8$)cycloalkyl-SO$_2$—, optionally substituted aryl (C$_1$-C$_6$)alkoxy-, optionally substituted (C$_3$-C$_8$)cycloalkyl (C$_1$-C$_6$)alkoxy-, optionally substituted heterocyclyl-CO—, optionally substituted (C$_1$-C$_6$)alkyl-SO$_2$—, —NR$^6$SO$_2$-optionally substituted (C$_1$-C$_6$)alkyl, —R$^6$SO$_2$-optionally substituted heterocyclo, optionally substituted (C$_1$-C$_6$)alkyl-NR$^6$SO$_2$— or optionally substituted heterocyclo-NR$^6$SO$_2$—;

R$^2$ is hydrogen, halogen, —CN, OH, —CONR$^3$R$^4$, —NR$^6$COOR$^4$, —NR$^6$CONR$^3$R$^4$, —NR$^6$COR$^4$, —NR$^6$SO$_2$R$^5$, —SO$_2$NR$^3$R$^4$, —NR$^6$SO$_2$NR$^3$R$^4$, optionally substituted (C$_1$-C$_6$)alkyl, optionally substituted (C$_3$-C$_8$)cycloalkyl, optionally substituted (C$_1$-C$_6$) alkoxy, optionally substituted (C$_1$-C$_6$)alkyl-SO$_2$—, or optionally substituted aryl-SO$_2$—;

R$^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl(C$_1$-C$_6$)alkyl;

R$^4$ is hydrogen, optionally substituted (C$_1$-C$_6$)alkyl or optionally substituted (C$_3$-C$_8$)cycloalkyl;

R$^5$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl(C$_1$-C$_6$)alkyl;

R$^6$ is hydrogen or optionally substituted (C$_1$-C$_6$)alkyl;

R$^7$ is hydrogen, optionally substituted (C$_1$-C$_6$)alkyl, haloalkyl, —OR$^4$, CN, —CONH$_2$ or halogen;

or a pharmaceutically acceptable salt, tautomer or stereoisomer thereof.

2. A compound according to claim 1 of formula (II)

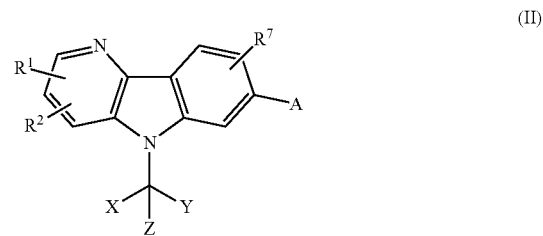

wherein:
A is

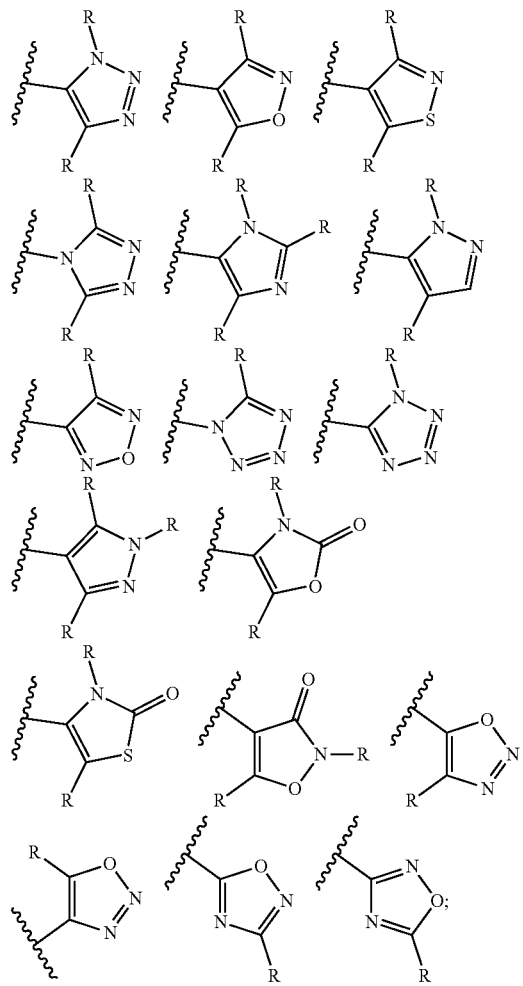

R is independently one or more hydrogen, CD₃, halogen, haloalkyl, hydroxyalkyl, CN, CF₃, CH₂F, CHF₂, optionally substituted (C₁-C₆)alkyl, optionally substituted (C₁-C₆)alkoxy, optionally substituted (C₃-C₆)cycloalkyl, —OR⁴, —NR³R⁴, NR³R⁴(C₁-C₆)alkyl-, —NR⁶OCOR³, —NR⁶COR³, —NR⁶CONR³R⁴;

X and Y are independently selected from optionally substituted (C₁-C₆)alkyl, optionally substituted (C₃-C₈)cycloalkyl, optionally substituted aryl, optionally substituted heteroaryl or optionally substituted heterocyclo;

Z is hydrogen, halogen, —OH, (C₁-C₆)alkyl or (C₁-C₆)alkoxy;

R¹ is hydrogen, halogen, —CN, —OR⁴, —NR³R⁴, —CONR³R⁴, —COOH, —OCONR³R⁴, —NR⁶OCOR³, —NR⁶CONR³R⁴, —NR⁶SO₂NR³R⁴, —NR⁶SO₂R⁴, optionally substituted (C₁-C₆)alkyl, optionally substituted (C₂-C₆)alkenyl, optionally substituted (C₂-C₆)alkynyl, optionally substituted (C₁-C₆)alkoxy, optionally substituted (C₃-C₈)cycloalkyl, optionally substituted (C₃-C₈)cycloalkyl (C₁-C₆)alkyl, optionally substituted (C₃-C₈)cycloalkyl-CO—, optionally substituted (C₃-C₈)cycloalkyl-SO₂—, optionally substituted aryl (C₁-C₆)alkoxy-, optionally substituted (C₃-C₈)cycloalkyl (C₁-C₆)alkoxy-, optionally substituted heterocyclyl-CO—, optionally substituted (C₁-C₆)alkyl-SO₂—, —NR⁶SO₂-optionally substituted (C₁-C₆)alkyl, —NR⁶SO₂-optionally substituted heterocyclo, optionally substituted (C₁-C₆)alkyl-NR⁶SO₂— or optionally substituted heterocyclo-NR⁶SO₂—;

R² is hydrogen, halogen, —CN, OH, optionally substituted (C₁-C₆)alkyl, optionally substituted (C₃-C₈)cycloalkyl, optionally substituted (C₁-C₆) alkoxy, optionally substituted (C₁-C₆)alkyl-SO₂—, or optionally substituted aryl-SO₂—;

R³ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl(C₁-C₆)alkyl;

R⁴ is hydrogen, optionally substituted (C₁-C₆)alkyl or optionally substituted (C₃-C₈)cycloalkyl;

R⁶ is hydrogen or optionally substituted (C₁-C₆)alkyl;

R⁷ is hydrogen, optionally substituted (C₁-C₆)alkyl, haloalkyl, —OR⁴, CN, —CONH₂ or halogen;

or a pharmaceutically acceptable salt, tautomer or stereoisomer thereof.

3. A compound according to claim 1 of the formula

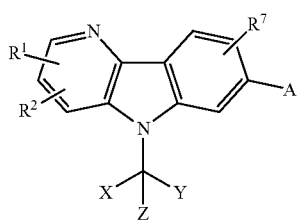

wherein
A is

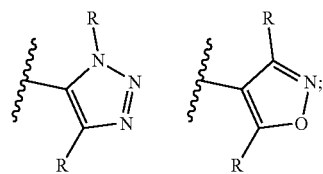

R is independently one or more hydrogen, CD₃, halogen, haloalkyl, hydroxyalkyl, CN, CF₃, CH₂F, CHF₂, optionally substituted (C₁-C₆)alkyl, optionally substituted (C₁-C₆)alkoxy, optionally substituted (C₃-C₆)cycloalkyl, —OR⁴, —NR³R⁴, NR³R⁴(C₁-C₆)alkyl-, —NR⁶OCOR³, —NR⁶COR³, —NR⁶CONR³R⁴;

X and Y are independently selected from optionally substituted (C₁-C₆)alkyl, optionally substituted (C₃-C₈)cycloalkyl, optionally substituted aryl, optionally substituted heteroaryl or optionally substituted heterocyclo;

Z is hydrogen, halogen, —OH, (C₁-C₆)alkyl or (C₁-C₆)alkoxy;

R¹ is hydrogen, halogen, —CN, —OR⁴, —NR³R⁴, —CONR³R⁴, —COOH, —OCONR³R⁴, —NR⁶OCOR³, —NR⁶CONR³R⁴, —NR⁶SO₂NR³R⁴, —NR⁶SO₂R⁴, optionally substituted (C₁-C₆)alkyl, optionally substituted (C₂-C₆)alkenyl, optionally substituted (C₂-C₆)alkynyl, optionally substituted (C₁-C₆)alkoxy, optionally substituted (C₃-C₈)cycloalkyl, optionally substituted (C₃-C₈)cycloalkyl (C₁-C₆)alkyl, optionally substituted (C₃-C₈)cycloalkyl-CO—, optionally substituted (C₃-C₈)cycloalkyl-SO₂—, optionally substituted aryl (C₁-C₆)alkoxy-, optionally substituted (C₃-C₈)cycloalkyl (C₁-C₆)alkoxy-, optionally substituted heterocyclyl-CO—, optionally substituted (C₁-C₆)alkyl-SO₂—, —NR⁶SO₂-optionally substituted (C₁-C₆)alkyl, —NR⁶SO₂-optionally substituted heterocyclo, optionally substituted (C₁-C₆)alkyl-NR⁶SO₂— or optionally substituted heterocyclo-NR⁶SO₂—;

R² is hydrogen, halogen, —CN, OH, optionally substituted (C₁-C₆)alkyl, optionally substituted (C₃-C₈)cycloalkyl, optionally substituted (C₁-C₆) alkoxy, optionally substituted (C₁-C₆)alkyl-SO₂—, or optionally substituted aryl-SO₂—;

R³ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl (C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl(C₁-C₆)alkyl;

R⁴ is hydrogen, optionally substituted (C₁-C₆)alkyl or optionally substituted (C₃-C₈)cycloalkyl;

R⁶ is hydrogen or optionally substituted (C₁-C₆)alkyl;

R⁷ is hydrogen, optionally substituted (C₁-C₆)alkyl, haloalkyl, —OR⁴, CN, —CONH₂ or halogen;

or a pharmaceutically acceptable salt, tautomer or stereoisomer thereof.

4. A compound according to claim 3 of the formula

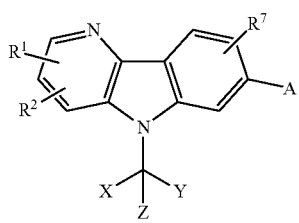

(I)

wherein:
A is

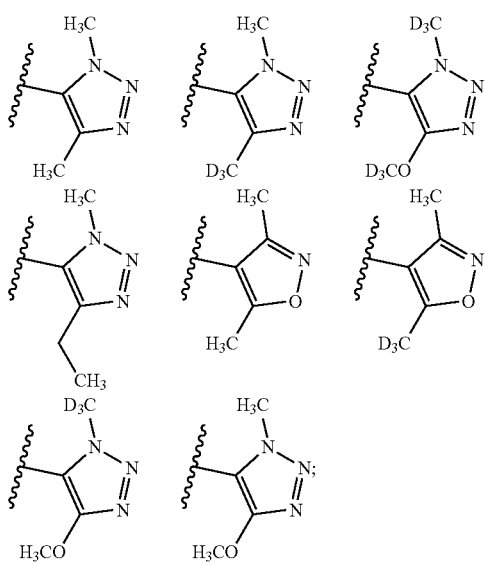

X and Y are independently selected from optionally substituted $(C_1-C_6)$alkyl, optionally substituted $(C_3-C_8)$cycloalkyl, optionally substituted aryl, optionally substituted heteroaryl or optionally substituted heterocyclo;

Z is hydrogen, halogen, —OH, $(C_1-C_6)$alkyl or $(C_1-C_6)$ alkoxy;

$R^1$ is, independently at each occurrence, one or more hydrogen, halogen, —CN, —$OR^4$, —$NR^3R^4$, —$CONR^3R^4$, —COOH, —$OCONR^3R^4$, —$NR^6OCOR^3$, —$NR^6CONR^3R^4$, —$NR^6SO_2NR^3R^4$, —$NR^6SO_2R^4$, optionally substituted $(C_1-C_6)$alkyl, optionally substituted $(C_2-C_6)$alkenyl, optionally substituted $(C_2-C_6)$alkynyl, optionally substituted $(C_1-C_6)$ alkoxy, optionally substituted $(C_3-C_8)$cycloalkyl, optionally substituted $(C_3-C_8)$cycloalkyl $(C_1-C_6)$alkyl, optionally substituted $(C_3-C_8)$cycloalkyl-CO—, optionally substituted $(C_3-C_8)$cycloalkyl-$SO_2$—, optionally substituted aryl $(C_1-C_6)$alkoxy-, optionally substituted $(C_3-C_8)$cycloalkyl $(C_1-C_6)$alkoxy-, optionally substituted heterocyclyl-CO—, optionally substituted $(C_1-C_6)$alkyl-$SO_2$—, —$NR^6SO_2$-optionally substituted $(C_1-C_6)$alkyl, —$NR^6SO_2$-optionally substituted heterocyclo, optionally substituted $(C_1-C_6)$alkyl-$NR^6SO_2$— or optionally substituted heterocyclo-$NR^6SO_2$—;

$R^2$ is hydrogen, halogen, —CN, OH, optionally substituted $(C_1-C_6)$alkyl, optionally substituted $(C_3-C_8)$cycloalkyl, optionally substituted $(C_1-C_6)$ alkoxy, optionally substituted $(C_1-C_6)$alkyl-$SO_2$—, or optionally substituted aryl-$SO_2$—;

$R^3$ is hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl $(C_1-C_6)$alkyl, optionally substituted aryloxy$(C_1-C_6)$ alkyl, optionally substituted $(C_1-C_6)$alkyl-$SO_2$—, optionally substituted heterocyclyl, optionally substituted heterocyclyl$(C_1-C_6)$alkyl, optionally substituted heteroaryl or optionally substituted heteroaryl$(C_1-C_6)$ alkyl;

$R^4$ is hydrogen, optionally substituted $(C_1-C_6)$alkyl or optionally substituted $(C_3-C_8)$cycloalkyl;

$R^6$ is hydrogen or optionally substituted $(C_1-C_6)$alkyl;

$R^7$ is hydrogen, optionally substituted $(C_1-C_6)$alkyl, haloalkyl, —$OR^4$, CN, —$CONH_2$ or halogen;

or a pharmaceutically acceptable salt, tautomer or stereoisomer thereof.

5. A compound selected from the following:
5-benzyl-7-(dimethyl-1,2-oxazol-4-yl)-2-methyl-5H-pyrido[3,2-b]indole-9-carboxamide,
4-{5-benzyl-2-methyl-5H-pyrido[3,2-b]indol-7-yl}-3,5-dimethyl-1,2-oxazole,
2-[7-(dimethyl-1H-1,2,3-triazol-5-yl)-5-[(S)-(4-fluorophenyl)(oxan-4-yl)methyl]-5H-pyrido[3,2-b]indol-3-yl]propan-2-ol,
2-[7-(dimethyl-1H-1,2,3-triazol-5-yl)-5-(1,1,1,7,7,7-hexafluoroheptan-4-yl)-5H-pyrido[3,2-b]indol-3-yl]propan-2-ol,
2-[7-(dimethyl-1H-1,2,3-triazol-5-yl)-5-(heptan-4-yl)-5H-pyrido[3,2-b]indol-3-yl]propan-2-ol,
2-[7-(dimethyl-1H-1,2,3-triazol-5-yl)-5-[4,4,4-trifluoro-1-(pyridin-2-yl)butyl]-5H-pyrido[3,2-b]indol-3-yl]propan-2-ol,
2-[7-(dimethyl-1H-1,2,3-triazol-5-yl)-5-[(S)-oxan-4-yl(phenyl)methyl]-5H-pyrido[3,2-b]indol-3-yl]propan-2-ol,
2-[7-(dimethyl-1H-1,2,3-triazol-5-yl)-5-[(S)-(2-fluorophenyl)(oxan-4-yl)methyl]-5H-pyrido[3,2-b]indol-3-yl]propan-2-ol,
2-[7-(dimethyl-1H-1,2,3-triazol-5-yl)-9-fluoro-5-(1,1,1,7,7,7-hexafluoroheptan-4-yl)-5H-pyrido[3,2-b]indol-3-yl]propan-2-ol,
2-[7-(dimethyl-1H-1,2,3-triazol-5-yl)-9-fluoro-5-[(S)-oxan-4-yl(phenyl)methyl]-5H-pyrido[3,2-b]indol-3-yl] propan-2-ol,
2-[9-chloro-7-(dimethyl-1H-1,2,3-triazol-5-yl)-5-(1,1,1,7,7,7-hexafluoroheptan-4-yl)-5H-pyrido[3,2-b]indol-3-yl]propan-2-ol,
2-[9-chloro-7-(dimethyl-1H-1,2,3-triazol-5-yl)-5-[(S)-oxan-4-yl(phenyl)methyl]-5H-pyrido[3,2-b]indol-3-yl] propan-2-ol,
2-[7-(dimethyl-1,2-oxazol-4-yl)-5-[(S)-oxan-4-yl(phenyl)methyl]-5H-pyrido[3,2-b]indol-3-yl]propan-2-ol,
2-[7-(dimethyl-1,2-oxazol-4-yl)-5-[(S)-(2-fluorophenyl)(oxan-4-yl)methyl]-5H-pyrido[3,2-b]indol-3-yl]propan-2-ol,
2-{7-[4-($^2H_3$)methyl-1-methyl-1H-1,2,3-triazol-5-yl]-5-[(S)-oxan-4-yl(phenyl)methyl]-5H-pyrido[3,2-b]indol-3-yl}propan-2-ol,
2-[7-(dimethyl-1,2-oxazol-4-yl)-6-fluoro-5-[(S)-oxan-4-yl(phenyl)methyl]-5H-pyrido[3,2-b]indol-3-yl]propan-2-ol, 2-[7-(dimethyl-1,2-oxazol-4-yl)-8-fluoro-5-[(S)-oxan-4-yl(phenyl)methyl]-5H-pyrido[3,2-b]indol-3-yl]propan-2-ol, 2-[7-(dimethyl-1H-1,2,3-triazol-5-yl)-8-fluoro-5-[(S)-oxan-4-yl(phenyl)methyl]-5H-pyrido[3,2-b]indol-3-yl]propan-2-ol, 2-[7-(dimethyl-1H-1,2,3-triazol-5-yl)-6-fluoro-5-[(S)-oxan-4-yl(phenyl)methyl]-5H-pyrido[3,2-b]indol-3-yl]propan-2-ol, 2-[7-(dimethyl-1H-1,2,3-triazol-5-yl)-8-fluoro-5-[(S)-(2-fluorophenyl)(oxan-4-yl)methyl]-5H-pyrido[3,2-b]indol-3-yl]propan-2-ol, 2-{8-fluoro-5-[(S)-(2-fluorophenyl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, 1-cyclopropyl-1-[7-(dimethyl-1H-1,2,3-triazol-5-yl)-8-fluoro-5-[(S)-(2-fluorophenyl)(oxan-4-yl)methyl]-5H-pyrido[3,2-b]indol-3-yl]ethan-1-ol, 5-{8-fluoro-5-[(S)-(2-fluorophenyl)(oxan-4-yl)methyl]-3-methanesulfonyl-5H-pyrido[3,2-b]indol-7-yl}-1,4-dimethyl-1H-1,2,3-triazole, 5-{3-methanesulfonyl-5-[(S)-oxan-4-yl(phenyl)methyl]-5H-pyrido[3,2-b]indol-7-yl}-1,4-dimethyl-1H-1,2,3-triazole, 5-{3-methanesulfonyl-5-[(S)-oxan-4-yl(phenyl)methyl]-5H-pyrido[3,2-b]indol-7-yl}-4-($^2$H$_3$)methyl-1-methyl-1H-1,2,3-triazole, 5-{8-fluoro-5-[(S)-(2-fluorophenyl)(oxan-4-yl)methyl]-3-methanesulfonyl-5H-pyrido[3,2-b]indol-7-yl}-4-($^2$H$_3$)methyl-1-methyl-1H-1,2,3-triazole, 7-(dimethyl-1H-1,2,3-triazol-5-yl)-5-[(S)-(2-fluorophenyl)(oxan-4-yl)methyl]-5H-pyrido[3,2-b]indole-3-carboxylic acid, 2-{8-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, 2-{8-fluoro-7-[4-($^2$H$_3$)methyl-1-methyl-1H-1,2,3-triazol-5-yl]-5-[(S)-oxan-4-yl(phenyl)methyl]-5H-pyrido[3,2-b]indol-3-yl}propan-2-ol, 2-{8-fluoro-7-[5-($^2$H$_3$)methyl-3-methyl-1,2-oxazol-4-yl]-5-[(S)-oxan-4-yl(phenyl)methyl]-5H-pyrido[3,2-b]indol-3-yl}propan-2-ol, 2-{8-fluoro-5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, 2-{8-fluoro-7-[4-($^2$H$_3$)methyl-1-methyl-1H-1,2,3-triazol-5-yl]-5-[oxan-4-yl(pyridin-2-yl)methyl]-5H-pyrido[3,2-b]indol-3-yl}propan-2-ol, 2-{8-fluoro-5-[1-(3-fluoropyridin-2-yl)butyl]-7-[4-($^2$H$_3$)methyl-1-methyl-1H-1,2,3-triazol-5-yl]-5H-pyrido[3,2-b]indol-3-yl}propan-2-ol, 2-{8-fluoro-5-[(3-methoxypyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, 2-{8-fluoro-7-[4-($^2$H$_3$)methyl-1-methyl-1H-1,2,3-triazol-5-yl]-5-[(3-methylpyridin-2-yl)(oxan-4-yl)methyl]-5H-pyrido[3,2-b]indol-3-yl}propan-2-ol, 2-{8-fluoro-5-[(5-fluoropyridin-2-yl)(oxan-4-yl)methyl]-7-[4-(methyl-1-methyl-1H-1,2,3-triazol-5-yl]-5H-pyrido[3,2-b]indol-3-yl}propan-2-ol, 2-{8-fluoro-7-[4-($^2$H$_3$)methyl-1-methyl-1H-1,2,3-triazol-5-yl]-5-[oxan-4-yl(pyrimidin-2-yl)methyl]-5H-pyrido[3,2-b]indol-3-yl}propan-2-ol, 2-{8-fluoro-7-[4-($^2$H$_3$)methyl-1-methyl-1H-1,2,3-triazol-5-yl]-5-[1-(pyridin-2-yl)butyl]-5H-pyrido[3,2-b]indol-3-yl}propan-2-ol, 2-{8-fluoro-5-[(4-methoxypyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, 2-{8-fluoro-7-[4-($^2$H$_3$)methyl-1-methyl-1H-1,2,3-triazol-5-yl]-5-[(4-methylpyridin-2-yl)(oxan-4-yl)methyl]-5H-pyrido[3,2-b]indol-3-yl}propan-2-ol, 2-[7-(dimethyl-1H-1,2,3-triazol-5-yl)-8-fluoro-5-[oxan-4-yl(pyrimidin-2-yl)methyl]-5H-pyrido[3,2-b]indol-3-yl]propan-2-ol, 2-{8-fluoro-7-[4-($^2$H$_3$)methyl-1-methyl-1H-1,2,3-triazol-5-yl]-5-[(5-methylpyridin-2-yl)(oxan-4-yl)methyl]-5H-pyrido[3,2-b]indol-3-yl}propan-2-ol, 2-{8-fluoro-5-[1-(5-fluoropyridin-2-yl)butyl]-7-[4-($^2$H$_3$)methyl-1-methyl-1H-1,2,3-triazol-5-yl]-5H-pyrido[3,2-b]indol-3-yl}propan-2-ol, 2-{8-fluoro-5-[(4-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, 2-{5-[5,6-dihydro-2H-pyran-3-yl(phenyl)methyl]-8-fluoro-7-[4-($^2$H$_3$)methyl-1-methyl-1H-1,2,3-triazol-5-yl]-5H-pyrido[3,2-b]indol-3-yl}propan-2-ol, 2-[8-fluoro-5-(3-methoxy-1-phenylpropyl)-7-[4-($^2$H$_3$)methyl-1-methyl-1H-1,2,3-triazol-5-yl]-5H-pyrido[3,2-b]indol-3-yl]propan-2-ol, 2-{8-fluoro-7-[4-($^2$H$_3$)methyl-1-methyl-1H-1,2,3-triazol-5-yl]-5-[(3-methyloxetan-3-yl)(phenyl)methyl]-5H-pyrido[3,2-b]indol-3-yl}propan-2-ol, 2-{8-fluoro-7-[4-($^2$H$_3$)methyl-1-methyl-1H-1,2,3-triazol-5-yl]-5-[2-(oxetan-3-yl)-1-phenylethyl]-5H-pyrido[3,2-b]indol-3-yl}propan-2-ol, 2-{8-fluoro-7-[4-($^2$H$_3$)methyl-1-methyl-1H-1,2,3-triazol-5-yl]-5-[oxetan-3-yl(phenyl)methyl]-5H-pyrido[3,2-b]indol-3-yl}propan-2-ol, 2-[7-(dimethyl-1H-1,2,3-triazol-5-yl)-8-fluoro-5-[(5-fluoropyridin-2-yl)(oxan-4-yl)methyl]-5H-pyrido[3,2-b]indol-3-yl]propan-2-ol, 2-{5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, 2-{5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, 2-{8-chloro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, 2-{8-chloro-7-[4-($^2$H$_3$)methyl-1-methyl-1H-1,2,3-triazol-5-yl]-5-[(S)-oxan-4-yl(phenyl)methyl]-5H-pyrido[3,2-b]indol-3-yl}propan-2-ol, 2-{8-chloro-5-[(5-methyl-1,2-oxazol-3-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, 2-{8-chloro-7-[4-($^2$H$_3$)methyl-1-methyl-1H-1,2,3-triazol-5-yl]-5-[oxan-4-yl(pyridin-2-yl)methyl]-5H-pyrido[3,2-b]indol-3-yl}propan-2-ol, 2-{8-chloro-5-[1-(3-fluoropyridin-2-yl)butyl]-7-[4-($^2$H$_3$)methyl-1-methyl-1H-1,2,3-triazol-5-yl]-5H-pyrido[3,2-b]indol-3-yl}propan-2-ol, 2-{6-fluoro-5-[(3-fluoropyridin-2-yl)(oxan-4-yl)methyl]-7-[4-($^2$H$_3$)methyl-1-methyl-1H-1,2,3-triazol-5-yl]-5H-pyrido[3,2-b]indol-3-yl}propan-2-ol, or a pharmaceutically acceptable salt, tautomer or stereoisomer thereof.

6. A pharmaceutical composition which comprises a compound according to claim 1 or a pharmaceutically acceptable salt thereof and one or more pharmaceutically acceptable carriers, diluents or excipients.

7. A combination pharmaceutical product comprising a compound according to claim 1 or a pharmaceutically acceptable salt thereof together with one or more other therapeutically active agents.

* * * * *